(12) United States Patent
Yang et al.

(10) Patent No.: US 8,206,960 B1
(45) Date of Patent: *Jun. 26, 2012

(54) ENDOGLUCANASES

(75) Inventors: Jie Yang, Foster City, CA (US); Andrew Shaw, Foster City, CA (US); Ish Kumar Dhawan, Foster City, CA (US); Onorato Campopiano, Hayward, CA (US); Kripa Rao, San Mateo, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/323,724

(22) Filed: Dec. 12, 2011

Related U.S. Application Data

(63) Continuation of application No. 12/751,985, filed on Mar. 31, 2010, now Pat. No. 8,088,608.

(60) Provisional application No. 61/165,312, filed on Mar. 31, 2009.

(51) Int. Cl.
 *C12N 9/00* (2006.01)
(52) U.S. Cl. ........................................................ 435/183
(58) Field of Classification Search .................. None
 See application file for complete search history.

(56) References Cited

U.S. PATENT DOCUMENTS

| | | | |
|---|---|---|---|
| 6,117,679 | A | 9/2000 | Stemmer |
| 6,376,246 | B1 | 4/2002 | Crameri et al. |
| 6,586,182 | B1 | 7/2003 | Patten et al. |
| 7,807,419 | B2 | 10/2010 | Hennessey et al. |
| 2008/0220990 | A1 | 9/2008 | Fox |
| 2009/0019608 | A1 | 1/2009 | Lopez de Leon et al. |
| 2009/0035826 | A1 | 2/2009 | Tolan et al. |
| 2009/0312196 | A1 | 12/2009 | Colbeck et al. |

FOREIGN PATENT DOCUMENTS

WO   WO 99/31255   *  6/1999

OTHER PUBLICATIONS

Roche et al., "Particle Concentration and Yield Stress of Biomass Slurries During Enzymatic Hydrolysis at High-Solids Loadings," *Biotechnology and Bioengineering*, 104(2): 290-300 (Oct. 1, 2009).
Sulzenbacher et al., "The Crystal Structure of a 2-Fluorocellotriosyl Complex of the Streptomyces Lividans Endoglucanase CelB2 at 1.2A Resolution," *Biochemistry: American Chemical Society*, 38: 4826-4833. (1999).

* cited by examiner

*Primary Examiner* — Suzanne M Noakes
(74) *Attorney, Agent, or Firm* — Kilpatrick Townsend & Stockton LLP

(57) ABSTRACT

The present invention relates to variant endoglucanases and particularly endoglucanases having improved properties over wild-type endoglucanase.

22 Claims, 7 Drawing Sheets

FIGURE 1A

Amino acid sequence of the Catalytic Domain of wild-type *Streptomyces avermitilis* endoglucanase (native SavO-EG catalytic domain) (SEQ ID NO:1).

DTSICEPFGSTTIQGRYVVQNNRWGTSEAQCITATDSGFRITQADGSVPTNGAPKSYPSVY
NGCHYTNCSPGTSLPAQLSTVSSAPTSISYSYVSNAMYDAAYDIWLDPTPRTDGVNRTEIM
VWFNKVGSVQPVGSQVGTATVAGRQWQVWSGNNGSNDVLSFVAPSAITSWSFDVMDFVRQA
VSRGLAQNSWYLTSVQAGFEPWQNGAGLAVTSFSSTVNT

FIGURE 1B

Amino acid sequence of the Catalytic Domain of wild-type *Streptomyces avermitilis* endoglucanase including the amino-terminal spacer (CDX-SavOCat) (SEQ ID NO: 2)

DTSMDTSICEPFGSTTIQGRYVVQNNRWGTSEAQCITATDSGFRITQADGSVPTNGAPKSY
PSVYNGCHYTNCSPGTSLPAQLSTVSSAPTSISYSYVSNAMYDAAYDIWLDPTPRTDGVNR
TEIMVWFNKVGSVQPVGSQVGTATVAGRQWQVWSGNNGSNDVLSFVAPSAITSWSFDVMDF
VRQAVSRGLAQNSWYLTSVQAGFEPWQNGAGLAVTSFSSTVNT

FIGURE 1C

Wild-type *Streptomyces avermitilis* endoglucanase (SavO EG) (GenBank accession NP_821730) – The signal peptide is underlined and the linker and CBD are underlined and in bold (SEQ ID NO: 3)

<u>MRPSPPHARSARGLFGALLTALVSLAALLTTASVAQA</u>DTSICEPFGSTTIQGRYVVQNNRW
GTSEAQCITATDSGFRITQADGSVPTNGAPKSYPSVYNGCHYTNCSPGTSLPAQLSTVSSA
PTSISYSYVSNAMYDAAYDIWLDPTPRTDGVNRTEIMVWFNKVGSVQPVGSQVGTATVAGR
QWQVWSGNNGSNDVLSFVAPSAITSWSFDVMDFVRQAVSRGLAQNSWYLTSVQAGFEPWQN
GAGLAVTSFSSTVNT**<u>GGGNPGDPGSPTACKVAYATNVWQGGFTADVTVTNTGSSPVNGWKL
AFTLPAGQQITSSWSAGVSPSSGAVTASSLAYNAQIATGGRVSFGFQGSYSGTFAAPAGFS
LNGAACTTA</u>**

FIGURE 2A

SEQ ID NO: 4 comprising the codon optimized Streptomyces avermitilis endoglucanase polynucleotide which includes the catalytic domain represented by nucleic acids 1-666, a linker and cellulose binding domain (CBM) represented by nucleic acids 667-1017. The linker and CBM are in bold and underlined.

GATACTTCTATTTGTGAACCATTTGGATCTACTACAATCCAAGGACGCTATGTAGTACAGA
ATAATCGTTGGGGCACAAGTGAAGCTCAATGTATAACAGCAACCGATTCAGGATTCCGCAT
TACCCAAGCGGATGGTTCTGTACCAACGAATGGTGCTCCTAAATCTTATCCAAGTGTCTAT
AACGGATGTCATTATACAAATTGCTCTCCTGGGACGTCGCTTCCAGCCCAATTATCAACAG
TTTCATCTGCTCCAACATCTATTAGTTATTCTTACGTGTCAAATGCCATGTATGATGCCGC
GTACGACATTTGGTTAGATCCAACACCGCGCACAGATGGTGTAAATCGAACAGAAATCATG
GTGTGGTTTAATAAAGTAGGCAGCGTGCAGCCAGTAGGATCTCAAGTAGGTACGGCTACGG
TGGCAGGCCGACAATGGCAGGTTTGGTCAGGAAATAACGGATCTAATGATGTGCTTAGTTT
CGTAGCTCCAAGTGCCATTACTTCATGGTCTTTTGATGTAATGGACTTTGTTCGTCAAGCC
GTTAGTCGCGGATTAGCTCAAAACTCTTGGTATTTGACATCTGTCCAAGCTGGATTTGAAC
CGTGGCAGAATGGCGCTGGACTAGCAGTAACTTCTTTTTCGTCTACGGTAAACACT<u>GGAGG</u>
<u>CGGCAATCCAGGAGATCCGGGATCTCCTACTGCTTGCAAAGTTGCTTATGCAACGAATGTT</u>
<u>TGGCAAGGTGGATTTACGGCTGACGTAACTGTAACGAATACAGGGTCCTCACCTGTCAATG</u>
<u>GATGGAAACTTGCTTTTACGTTACCAGCAGGCCAACAAATTACTTCGTCTTGGTCAGCAGG</u>
<u>AGTATCTCCGTCATCTGGAGCAGTGACAGCTTCTAGCCTTGCATACAATGCACAAATTGCA</u>
<u>ACCGGGGGACGTGTATCATTTGGATTTCAAGGTAGTTATTCTGGCACATTTGCAGCACCTG</u>
<u>CAGGTTTTTCTTTAAATGGGGCTGCTTGCACAACGGCATGA</u>

FIGURE 2B

SEQ ID NO: 5 comprising an N-terminal spacer (bases 1-12, described in Example 1) plus the codon optimized full-length *Streptomyces avermitilis* endoglucanase polynucleotide. The N-terminal spacer plus the catalytic domain are represented by nucleic acids 1-678. The linker and cellulose binding domain (CBM) are represented by nucleic acids 679-1029. The N-terminal spacer sequence is italicized and underlined. The linker and CBM are in bold and underlined.

*GATACTAGTATG*GATACTTCTATTTGTGAACCATTTGGATCTACTACAATCCAAGGACGCT
ATGTAGTACAGAATAATCGTTGGGGCACAAGTGAAGCTCAATGTATAACAGCAACCGATTC
AGGATTCCGCATTACCCAAGCGGATGGTTCTGTACCAACGAATGGTGCTCCTAAATCTTAT
CCAAGTGTCTATAACGGATGTCATTATACAAATTGCTCTCCTGGGACGTCGCTTCCAGCCC
AATTATCAACAGTTTCATCTGCTCCAACATCTATTAGTTATTCTTACGTGTCAAATGCCAT
GTATGATGCCGCGTACGACATTTGGTTAGATCCAACACCGCGCACAGATGGTGTAAATCGA
ACAGAAATCATGGTGTGGTTTAATAAAGTAGGCAGCGTGCAGCCAGTAGGATCTAAGTAG
GTACGGCTACGGTGGCAGGCCGACAATGGCAGGTTTGGTCAGGAAATAACGGATCTAATGA
TGTGCTTAGTTTCGTAGCTCCAAGTGCCATTACTTCATGGTCTTTTGATGTAATGGACTTT
GTTCGTCAAGCCGTTAGTCGCGGATTAGCTCAAAACTCTTGGTATTTGACATCTGTCCAAG
CTGGATTTGAACCGTGGCAGAATGGCGCTGGACTAGCAGTAACTTCTTTTTCGTCTACGGT
AAACACTGGAGGCGGCAATCCAGGAGATCCGGGATCTCCTACTGCTTGCAAAGTTGCTTAT
GCAACGAATGTTTGGCAAGGTGGATTTACGGCTGACGTAACTGTAACGAATACAGGGTCCT
CACCTGTCAATGGATGGAAACTTGCTTTTACGTTACCAGCAGGCCAACAAATTACTTCGTC
TTGGTCAGCAGGAGTATCTCCGTCATCTGGAGCAGTGACAGCTTCTAGCCTTGCATACAAT
GCACAAATTGCAACCGGGGGACGTGTATCATTTGGATTTCAAGGTAGTTATTCTGGCACAT
TTGCAGCACCTGCAGGTTTTTCTTTAAATGGGGCTGCTTGCACAACGGCATGA

SEQUENCE LISTING

```
<160> NUMBER OF SEQ ID NOS: 16

<210> SEQ ID NO 1
<211> LENGTH: 222
<212> TYPE: PRT
<213> ORGANISM: Artificial Sequence
<220> FEATURE:
<223> OTHER INFORMATION: synthetic wild-type Streptomyces avermitilis
      endogluganase catalytic domain

<400> SEQUENCE: 1

Asp Thr Ser Ile Cys Glu Pro Phe Gly Ser Thr Thr Ile Gln Gly Arg
1               5                   10                  15
```

-continued

```
Tyr Val Val Gln Asn Asn Arg Trp Gly Thr Ser Glu Ala Gln Cys Ile
             20                  25                  30

Thr Ala Thr Asp Ser Gly Phe Arg Ile Thr Gln Ala Asp Gly Ser Val
         35                  40                  45

Pro Thr Asn Gly Ala Pro Lys Ser Tyr Pro Ser Val Tyr Asn Gly Cys
 50                  55                  60

His Tyr Thr Asn Cys Ser Pro Gly Thr Ser Leu Pro Ala Gln Leu Ser
 65                  70                  75                  80

Thr Val Ser Ser Ala Pro Thr Ser Ile Ser Tyr Ser Val Ser Asn
                 85                  90                  95

Ala Met Tyr Asp Ala Ala Tyr Asp Ile Trp Leu Asp Pro Thr Pro Arg
             100                 105                 110

Thr Asp Gly Val Asn Arg Thr Glu Ile Met Val Trp Phe Asn Lys Val
         115                 120                 125

Gly Ser Val Gln Pro Val Gly Ser Gln Val Gly Thr Ala Thr Val Ala
130                 135                 140

Gly Arg Gln Trp Gln Val Trp Ser Gly Asn Asn Gly Ser Asn Asp Val
145                 150                 155                 160

Leu Ser Phe Val Ala Pro Ser Ala Ile Thr Ser Trp Ser Phe Asp Val
             165                 170                 175

Met Asp Phe Val Arg Gln Ala Val Ser Arg Gly Leu Ala Gln Asn Ser
         180                 185                 190

Trp Tyr Leu Thr Ser Val Gln Ala Gly Phe Glu Pro Trp Gln Asn Gly
     195                 200                 205

Ala Gly Leu Ala Val Thr Ser Phe Ser Ser Thr Val Asn Thr
210                 215                 220

<210> SEQ ID NO 2
<211> LENGTH: 226
<212> TYPE: PRT
<213> ORGANISM: Artificial Sequence
<220> FEATURE:
<223> OTHER INFORMATION: synthetic wild-type Streptomyces avermitilis
      endogluganase catalytic domain with N-terminal DTSM
      spacer

<400> SEQUENCE: 2

Asp Thr Ser Met Asp Thr Ser Ile Cys Glu Pro Phe Gly Ser Thr Thr
 1               5                  10                  15

Ile Gln Gly Arg Tyr Val Val Gln Asn Asn Arg Trp Gly Thr Ser Glu
             20                  25                  30

Ala Gln Cys Ile Thr Ala Thr Asp Ser Gly Phe Arg Ile Thr Gln Ala
         35                  40                  45

Asp Gly Ser Val Pro Thr Asn Gly Ala Pro Lys Ser Tyr Pro Ser Val
 50                  55                  60

Tyr Asn Gly Cys His Tyr Thr Asn Cys Ser Pro Gly Thr Ser Leu Pro
 65                  70                  75                  80

Ala Gln Leu Ser Thr Val Ser Ser Ala Pro Thr Ser Ile Ser Tyr Ser
             85                  90                  95

Tyr Val Ser Asn Ala Met Tyr Asp Ala Ala Tyr Asp Ile Trp Leu Asp
             100                 105                 110

Pro Thr Pro Arg Thr Asp Gly Val Asn Arg Thr Glu Ile Met Val Trp
         115                 120                 125

Phe Asn Lys Val Gly Ser Val Gln Pro Val Gly Ser Gln Val Gly Thr
130                 135                 140

Ala Thr Val Ala Gly Arg Gln Trp Gln Val Trp Ser Gly Asn Asn Gly
145                 150                 155                 160
```

Ser Asn Asp Val Leu Ser Phe Val Ala Pro Ser Ala Ile Thr Ser Trp
            165                 170                 175

Ser Phe Asp Val Met Asp Phe Val Arg Gln Ala Val Ser Arg Gly Leu
            180                 185                 190

Ala Gln Asn Ser Trp Tyr Leu Thr Ser Val Gln Ala Gly Phe Glu Pro
            195                 200                 205

Trp Gln Asn Gly Ala Gly Leu Ala Val Thr Ser Phe Ser Ser Thr Val
210                 215                 220

Asn Thr
225

<210> SEQ ID NO 3
<211> LENGTH: 375
<212> TYPE: PRT
<213> ORGANISM: Streptomyces avermitilis
<220> FEATURE:
<223> OTHER INFORMATION: wild-type Streptomyces avermitilis strain MA-
      4680 endo-1,4-beta-glucanase, 1,4-beta-D-glucan
      glucanohydrolase, locus SAV_555, celA1, endoglucanase

<400> SEQUENCE: 3

Met Arg Pro Ser Pro His Ala Arg Ser Ala Arg Gly Leu Phe Gly
 1               5                  10                  15

Ala Leu Leu Thr Ala Leu Val Ser Leu Ala Ala Leu Leu Thr Thr Ala
            20                  25                  30

Ser Val Ala Gln Ala Asp Thr Ser Ile Cys Glu Pro Phe Gly Ser Thr
            35                  40                  45

Thr Ile Gln Gly Arg Tyr Val Val Gln Asn Asn Arg Trp Gly Thr Ser
        50                  55                  60

Glu Ala Gln Cys Ile Thr Ala Thr Asp Ser Gly Phe Arg Ile Thr Gln
65                  70                  75                  80

Ala Asp Gly Ser Val Pro Thr Asn Gly Ala Pro Lys Ser Tyr Pro Ser
                85                  90                  95

Val Tyr Asn Gly Cys His Tyr Thr Asn Cys Ser Pro Gly Thr Ser Leu
            100                 105                 110

Pro Ala Gln Leu Ser Thr Val Ser Ser Ala Pro Thr Ser Ile Ser Tyr
            115                 120                 125

Ser Tyr Val Ser Asn Ala Met Tyr Asp Ala Ala Tyr Asp Ile Trp Leu
        130                 135                 140

Asp Pro Thr Pro Arg Thr Asp Gly Val Asn Arg Thr Glu Ile Met Val
145                 150                 155                 160

Trp Phe Asn Lys Val Gly Ser Val Gln Pro Val Gly Ser Gln Val Gly
                165                 170                 175

Thr Ala Thr Val Ala Gly Arg Gln Trp Gln Val Trp Ser Gly Asn Asn
            180                 185                 190

Gly Ser Asn Asp Val Leu Ser Phe Val Ala Pro Ser Ala Ile Thr Ser
        195                 200                 205

Trp Ser Phe Asp Val Met Asp Phe Val Arg Gln Ala Val Ser Arg Gly
210                 215                 220

Leu Ala Gln Asn Ser Trp Tyr Leu Thr Ser Val Gln Ala Gly Phe Glu
225                 230                 235                 240

Pro Trp Gln Asn Gly Ala Gly Leu Ala Val Thr Ser Phe Ser Ser Thr
                245                 250                 255

Val Asn Thr Gly Gly Gly Asn Pro Gly Asp Pro Gly Ser Pro Thr Ala
            260                 265                 270

```
Cys Lys Val Ala Tyr Ala Thr Asn Val Trp Gln Gly Gly Phe Thr Ala
        275                 280                 285

Asp Val Thr Val Thr Asn Thr Gly Ser Ser Pro Val Asn Gly Trp Lys
    290                 295                 300

Leu Ala Phe Thr Leu Pro Ala Gly Gln Gln Ile Thr Ser Ser Trp Ser
305                 310                 315                 320

Ala Gly Val Ser Pro Ser Ser Gly Ala Val Thr Ala Ser Ser Leu Ala
                325                 330                 335

Tyr Asn Ala Gln Ile Ala Thr Gly Gly Arg Val Ser Phe Gly Phe Gln
            340                 345                 350

Gly Ser Tyr Ser Gly Thr Phe Ala Ala Pro Ala Gly Phe Ser Leu Asn
        355                 360                 365

Gly Ala Ala Cys Thr Thr Ala
        370                 375
```

<210> SEQ ID NO 4
<211> LENGTH: 1017
<212> TYPE: DNA
<213> ORGANISM: Artificial Sequence
<220> FEATURE:
<223> OTHER INFORMATION: synthetic codon optimized Streptomyces avermitilis endogluganase

<400> SEQUENCE: 4

```
gatacttcta tttgtgaacc atttggatct actacaatcc aaggacgcta tgtagtacag    60
aataatcgtt ggggcacaag tgaagctcaa tgtataacag caaccgattc aggattccgc   120
attacccaag cggatggttc tgtaccaacg aatggtgctc taaatcttta tccaagtgtc   180
tataacggat gtcattatac aaattgctct cctgggacgt cgcttccagc ccaattatca   240
acagtttcat ctgctccaac atctattagt tattcttacg tgtcaaatgc catgtatgat   300
gccgcgtacg acatttggtt agatccaaca ccgcgcacag atggtgtaaa tcgaacagaa   360
atcatggtgt ggtttaataa agtaggcagc gtgcagccag taggatctca gtaggtacg    420
gctacggtgg caggccgaca atggcaggtt tggtcaggaa ataacggatc taatgatgtg   480
cttagtttcg tagctccaag tgccattact tcatggtctt tgatgtaat ggactttgtt    540
cgtcaagccg ttagtcgcgg attagctcaa aactcttggt atttgacatc tgtccaagct   600
ggatttgaac cgtggcagaa tggcgctgga ctagcagtaa cttctttttc gtctacggta   660
aacactggag gcggcaatcc aggagatccg ggatctccta ctgcttgcaa agttgcttat   720
gcaacgaatg tttggcaagg tggatttacg gctgacgtaa ctgtaacgaa tacagggtcc   780
tcacctgtca atggatggaa acttgctttt acgttaccag caggccaaca aattacttcg   840
tcttggtcag caggagtatc tccgtcatct ggagcagtga cagcttctag ccttgcatac   900
aatgcacaaa ttgcaaccgg gggacgtgta tcatttggat tcaaggtag ttattctggc    960
acatttgcag cacctgcagg ttttttcttta atggggctg cttgcacaac ggcatga     1017
```

<210> SEQ ID NO 5
<211> LENGTH: 1029
<212> TYPE: DNA
<213> ORGANISM: Artificial Sequence
<220> FEATURE:
<223> OTHER INFORMATION: synthetic codon optimized Streptomyces avermitilis endogluganase with N-terminal DTSM spacer

<400> SEQUENCE: 5

```
gatactagta tggatacttc tatttgtgaa ccatttggat ctactacaat ccaaggacgc    60
tatgtagtac agaataatcg ttggggcaca agtgaagctc aatgtataac agcaaccgat   120
```

```
tcaggattcc gcattaccca agcggatggt tctgtaccaa cgaatggtgc tcctaaatct    180
tatccaagtg tctataacgg atgtcattat acaaattgct ctcctgggac gtcgcttcca    240
gcccaattat caacagtttc atctgctcca acatctatta gttattctta cgtgtcaaat    300
gccatgtatg atgccgcgta cgacatttgg ttagatccaa caccgcgcac agatggtgta    360
aatcgaacag aaatcatggt gtggtttaat aaagtaggca gcgtgcagcc agtaggatct    420
caagtaggta cggctacggt ggcaggccga caatggcagg tttggtcagg aaataacgga    480
tctaatgatg tgcttagttt cgtagctcca agtgccatta cttcatggtc ttttgatgta    540
atggactttg ttcgtcaagc cgttagtcgc ggattagctc aaaactcttg gtatttgaca    600
tctgtccaag ctggatttga accgtggcag aatggcgctg gactagcagt aacttctttt    660
tcgtctacgg taaacactgg aggcggcaat ccaggagatc cgggatctcc tactgcttgc    720
aaagttgctt atgcaacgaa tgtttggcaa ggtggattta cggctgacgt aactgtaacg    780
aatacagggt cctcacctgt caatggatgg aaacttgctt ttacgttacc agcaggccaa    840
caaattactt cgtcttggtc agcaggagta tctccgtcat ctggagcagt gacagcttct    900
agccttgcat acaatgcaca aattgcaacc ggggacgtg tatcatttgg atttcaaggt    960
agttattctg gcacatttgc agcacctgca ggttttctct taaatggggc tgcttgcaca    1020
acggcatga    1029
```

<210> SEQ ID NO 6
<211> LENGTH: 222
<212> TYPE: PRT
<213> ORGANISM: Artificial Sequence
<220> FEATURE:
<223> OTHER INFORMATION: synthetic Streptomyces avermitilis
      endogluganase variant

<400> SEQUENCE: 6

Asp Thr Ser Ile Cys Glu Pro Phe Gly Ser Thr Thr Ile Gln Gly Arg
 1               5                  10                  15

Tyr Val Val Gln Asn Asn Arg Trp Gly Thr Ser Glu Pro Gln Cys Ile
            20                  25                  30

Thr Ala Thr Asp Ser Gly Phe Arg Ile Thr Gln Ala Asp Gly Ser Val
        35                  40                  45

Pro Thr Asn Gly Pro Lys Ser Tyr Pro Ser Val Tyr Asn Gly Cys
    50                  55                  60

His Tyr Thr Asn Cys Ser Pro Gly Thr Pro Leu Pro Ala Gln Leu Ser
65                  70                  75                  80

Thr Val Ser Ser Ala Pro Thr Ser Ile Ser Tyr Ser Tyr Val Ser Asn
                85                  90                  95

Ala Met Tyr Asp Ala Ala Tyr Asp Ile Trp Leu Asp Pro Thr Pro Arg
            100                 105                 110

Thr Asp Gly Val Asn Arg Thr Glu Ile Met Val Trp Phe Asn Lys Val
        115                 120                 125

Gly Ser Val Gln Pro Val Gly Ser Gln Val Gly Thr Ala Thr Val Ala
    130                 135                 140

Gly Arg Gln Trp Gln Val Trp Ser Gly Asn Asn Gly Ser Asn Asp Val
145                 150                 155                 160

Leu Ser Phe Val Ala Pro Ser Ala Ile Thr Ser Trp Ser Phe Asp Val
                165                 170                 175

Met Asp Phe Val Arg Gln Ala Val Ser Arg Gly Leu Ala Gln Pro Ser
            180                 185                 190

```
Trp Tyr Leu Thr Ser Val Gln Ala Gly Phe Glu Pro Trp Gln Asn Gly
        195                 200                 205

Ala Gly Leu Ala Val Thr Ser Phe Ser Ser Thr Val Asn Thr
    210                 215                 220

<210> SEQ ID NO 7
<211> LENGTH: 222
<212> TYPE: PRT
<213> ORGANISM: Artificial Sequence
<220> FEATURE:
<223> OTHER INFORMATION: synthetic Streptomyces avermitilis
      endogluganase variant

<400> SEQUENCE: 7

Asp Thr Ser Ile Cys Glu Pro Phe Gly Trp Thr Thr Ile Gln Gly Arg
1               5                   10                  15

Tyr Val Val Gln Asn Asn Arg Trp Gly Thr Ser Glu Pro Gln Cys Ile
            20                  25                  30

Thr Ala Thr Asp Ser Gly Phe Arg Ile Thr Arg Ala Asp Gly Ser Val
        35                  40                  45

Pro Thr Asn Gly Pro Pro Lys Ser Tyr Pro Ser Val Tyr Asn Gly Cys
    50                  55                  60

His Tyr Thr Asn Cys Ser Pro Gly Thr Pro Leu Pro Ala Gln Leu Ser
65                  70                  75                  80

Thr Ile Ser Ser Ala Pro Thr Ser Ile Ser Tyr Ser Tyr Val Ser Asn
                85                  90                  95

Ala Val Tyr Asp Ala Ala Tyr Asp Ile Trp Leu Asp Pro Thr Pro Arg
            100                 105                 110

Thr Asp Gly Val Asn Arg Thr Glu Ile Met Val Trp Phe Asn Lys Val
        115                 120                 125

Gly Ser Val Gln Pro Val Gly Ser Gln Val Gly Thr Ala Thr Val Ala
    130                 135                 140

Gly Arg Gln Trp Gln Val Trp Ser Gly Asn Asn Gly Ser Asn Asp Val
145                 150                 155                 160

Leu Ser Phe Val Ala Pro Ser Ala Ile Thr Ser Trp Ser Phe Asp Val
                165                 170                 175

Met Asp Phe Val Arg Gln Ala Val Ser Arg Gly Leu Ala Gln Pro Ser
            180                 185                 190

Trp Tyr Leu Thr Ser Val Gln Ala Gly Phe Glu Pro Trp Gln Asn Gly
        195                 200                 205

Ala Gly Leu Ala Val Thr Ser Phe Ser Ser Thr Val Asn Thr
    210                 215                 220

<210> SEQ ID NO 8
<211> LENGTH: 222
<212> TYPE: PRT
<213> ORGANISM: Artificial Sequence
<220> FEATURE:
<223> OTHER INFORMATION: synthetic Streptomyces avermitilis
      endogluganase variant

<400> SEQUENCE: 8

Asp Thr Ser Ile Cys Glu Pro Phe Gly Trp Thr Val Ile Gln Gly Arg
1               5                   10                  15

Tyr Val Val Gln Asn Asn Arg Trp Gly Thr Ser Glu Pro Gln Cys Ile
            20                  25                  30

Thr Ala Thr Asp Ser Gly Phe Arg Ile Thr Arg Ala Asp Gly Ser Lys
        35                  40                  45
```

```
Pro Thr Asn Gly Pro Pro Lys Ser Tyr Pro Ser Val Tyr Asn Gly Cys
        50                  55                  60

His Tyr Thr Ile Cys Ser Pro Gly Thr Pro Leu Pro Ala Gln Ile Ser
 65                  70                  75                  80

Lys Ile Ser Ser Ala Pro Thr Ser Ile Ser Tyr Ser Tyr Val Ser Asn
                    85                  90                  95

Ala Val Tyr Asp Ala Ala Tyr Asp Ile Trp Leu Asp Pro Thr Pro Arg
                100                 105                 110

Thr Asp Gly Val Asn Arg Thr Glu Ile Met Val Trp Phe Asn Lys Val
            115                 120                 125

Gly Ser Val Gln Pro Val Gly Ser Gln Val Gly Thr Ala Thr Val Ala
        130                 135                 140

Gly Arg Gln Trp Gln Val Trp Met Gly Asn Asn Gly Ser Asn Asp Val
145                 150                 155                 160

Leu Ser Phe Val Ala Pro Ser Ala Ile Thr Ser Trp Ser Phe Asp Val
                165                 170                 175

Met Asp Phe Val Arg Gln Ala Val Gln Arg Gly Leu Ala Gln Pro Ser
                180                 185                 190

Trp Tyr Leu Thr Ser Val Gln Ala Gly Phe Glu Pro Trp Glu Asn Gly
            195                 200                 205

Ala Gly Leu Ala Val Thr Ser Phe Ser Ser Thr Val Asn Thr
        210                 215                 220

<210> SEQ ID NO 9
<211> LENGTH: 29
<212> TYPE: PRT
<213> ORGANISM: Artificial Sequence
<220> FEATURE:
<223> OTHER INFORMATION: synthetic Bacillus megaterium signal peptide

<400> SEQUENCE: 9

Met Lys Arg Ile Val Met Val Gly Phe Ile Leu Leu Phe Pro Leu Asn
 1               5                  10                  15

Met Leu Ala Gly Pro Ile Ser Ser Ile Ala Glu Ala Gln
            20                  25

<210> SEQ ID NO 10
<211> LENGTH: 254
<212> TYPE: PRT
<213> ORGANISM: Artificial Sequence
<220> FEATURE:
<223> OTHER INFORMATION: synthetic construct with Bacillus megaterium
      signal peptide, tripeptide spacer TSM and Streptomyces
      avermitilis endogluganase

<400> SEQUENCE: 10

Met Lys Arg Ile Val Met Val Gly Phe Ile Leu Leu Phe Pro Leu Asn
 1               5                  10                  15

Met Leu Ala Gly Pro Ile Ser Ser Ile Ala Glu Ala Gln Thr Ser Met
            20                  25                  30

Asp Thr Ser Ile Cys Glu Pro Phe Gly Trp Thr Val Ile Gln Gly Arg
                35                  40                  45

Tyr Val Val Gln Asn Asn Arg Trp Gly Thr Ser Glu Pro Gln Cys Ile
        50                  55                  60

Thr Ala Thr Asp Ser Gly Phe Arg Ile Thr Arg Ala Asp Gly Ser Lys
 65                  70                  75                  80

Pro Thr Asn Gly Pro Pro Lys Ser Tyr Pro Ser Val Tyr Asn Gly Cys
                85                  90                  95
```

```
His Tyr Thr Ile Cys Ser Pro Gly Thr Pro Leu Pro Ala Gln Ile Ser
                100                 105                 110

Lys Ile Ser Ser Ala Pro Thr Ser Ile Ser Tyr Ser Tyr Val Ser Asn
            115                 120                 125

Ala Val Tyr Asp Ala Ala Tyr Asp Ile Trp Leu Asp Pro Thr Pro Arg
        130                 135                 140

Thr Asp Gly Val Asn Arg Thr Glu Ile Met Val Trp Phe Asn Lys Val
145                 150                 155                 160

Gly Ser Val Gln Pro Val Gly Ser Gln Val Gly Thr Ala Thr Val Ala
                165                 170                 175

Gly Arg Gln Trp Gln Val Trp Met Gly Asn Asn Gly Ser Asn Asp Val
            180                 185                 190

Leu Ser Phe Val Ala Pro Ser Ala Ile Thr Ser Trp Ser Phe Asp Val
        195                 200                 205

Met Asp Phe Val Arg Gln Ala Val Gln Arg Gly Leu Ala Gln Pro Ser
    210                 215                 220

Trp Tyr Leu Thr Ser Val Gln Ala Gly Phe Glu Pro Trp Glu Asn Gly
225                 230                 235                 240

Ala Gly Leu Ala Val Thr Ser Phe Ser Ser Thr Val Asn Thr
                245                 250

<210> SEQ ID NO 11
<211> LENGTH: 218
<212> TYPE: PRT
<213> ORGANISM: Artificial Sequence
<220> FEATURE:
<223> OTHER INFORMATION: synthetic Hypocrea schweinitzii endoglucanase
      Cel12 catalytic domain

<400> SEQUENCE: 11

Gln Thr Ser Cys Asp Gln Tyr Ala Thr Phe Ser Gly Asn Gly Tyr Ile
1               5                   10                  15

Val Ser Asn Asn Leu Trp Gly Ala Ser Ala Gly Ser Gly Phe Gly Cys
            20                  25                  30

Val Thr Ser Val Ser Leu Asn Gly Ala Ala Ser Trp His Ala Asp Trp
        35                  40                  45

Gln Trp Ser Gly Gly Gln Asn Asn Val Lys Ser Tyr Gln Asn Val Gln
    50                  55                  60

Ile Asn Ile Pro Gln Lys Arg Thr Val Asn Ser Ile Gly Ser Met Pro
65                  70                  75                  80

Thr Thr Ala Ser Trp Ser Tyr Ser Gly Ser Asp Ile Arg Ala Asn Val
                85                  90                  95

Ala Tyr Asp Leu Phe Thr Ala Ala Asn Pro Asn His Val Thr Tyr Ser
            100                 105                 110

Gly Asp Tyr Glu Leu Met Ile Trp Leu Gly Lys Tyr Gly Asp Ile Gly
        115                 120                 125

Pro Ile Gly Ser Ser Gln Gly Thr Val Asn Val Gly Gly Gln Thr Trp
    130                 135                 140

Thr Leu Tyr Tyr Gly Tyr Asn Gly Ala Met Gln Val Tyr Ser Phe Val
145                 150                 155                 160

Ala Gln Ser Asn Thr Thr Ser Tyr Ser Gly Asp Val Lys Asn Phe Phe
                165                 170                 175

Asn Tyr Leu Arg Asp Asn Lys Gly Tyr Asn Ala Gly Gly Gln Tyr Val
            180                 185                 190

Leu Ser Tyr Gln Phe Gly Thr Glu Pro Phe Thr Gly Ser Gly Thr Leu
        195                 200                 205
```

```
Asn Val Ala Ser Trp Thr Ala Ser Ile Asn
    210                 215

<210> SEQ ID NO 12
<211> LENGTH: 227
<212> TYPE: PRT
<213> ORGANISM: Artificial Sequence
<220> FEATURE:
<223> OTHER INFORMATION: synthetic Rhodothermus marinus endoglucanase
      Cel12 catalytic domain

<400> SEQUENCE: 12

Thr Val Glu Leu Cys Gly Arg Trp Asp Ala Arg Asp Val Ala Gly Gly
 1               5                  10                  15

Arg Tyr Arg Val Ile Asn Asn Val Trp Gly Ala Glu Thr Ala Gln Cys
                20                  25                  30

Ile Glu Val Gly Leu Glu Thr Gly Asn Phe Thr Ile Thr Arg Ala Asp
            35                  40                  45

His Asp Asn Gly Asn Asn Val Ala Ala Tyr Pro Ala Ile Tyr Phe Gly
        50                  55                  60

Cys His Trp Gly Ala Cys Thr Ser Asn Ser Gly Leu Pro Arg Arg Val
 65                 70                  75                  80

Gln Glu Leu Ser Asp Val Arg Thr Ser Trp Thr Leu Thr Pro Ile Thr
                85                  90                  95

Thr Gly Arg Trp Asn Ala Ala Tyr Asp Ile Trp Phe Ser Pro Val Thr
               100                 105                 110

Asn Ser Gly Asn Gly Tyr Ser Gly Gly Ala Glu Leu Met Ile Trp Leu
           115                 120                 125

Asn Trp Asn Gly Gly Val Met Pro Gly Gly Ser Arg Val Ala Thr Val
       130                 135                 140

Glu Leu Ala Gly Ala Thr Trp Glu Val Trp Tyr Ala Asp Trp Asp Trp
145                 150                 155                 160

Asn Tyr Ile Ala Tyr Arg Arg Thr Thr Pro Thr Thr Ser Val Ser Glu
               165                 170                 175

Leu Asp Leu Lys Ala Phe Ile Asp Asp Ala Val Ala Arg Gly Tyr Ile
           180                 185                 190

Arg Pro Glu Trp Tyr Leu His Ala Val Glu Thr Gly Phe Glu Leu Trp
       195                 200                 205

Glu Gly Gly Ala Gly Leu Arg Ser Ala Asp Phe Ser Val Thr Val Gln
   210                 215                 220

Lys Leu Ala
225

<210> SEQ ID NO 13
<211> LENGTH: 222
<212> TYPE: PRT
<213> ORGANISM: Artificial Sequence
<220> FEATURE:
<223> OTHER INFORMATION: synthetic Streptomyces sp. 11AG8 endoglucanase
      Cel12 catalytic domain

<400> SEQUENCE: 13

Asn Gln Gln Ile Cys Asp Arg Tyr Gly Thr Thr Thr Ile Gln Asp Arg
 1               5                  10                  15

Tyr Val Val Gln Asn Asn Arg Trp Gly Thr Ser Ala Thr Gln Cys Ile
                20                  25                  30

Asn Val Thr Gly Asn Gly Phe Glu Ile Thr Gln Ala Asp Gly Ser Val
            35                  40                  45
```

```
Pro Thr Asn Gly Ala Pro Lys Ser Tyr Pro Ser Val Tyr Asp Gly Cys
 50                  55                  60

His Tyr Gly Asn Cys Ala Pro Arg Thr Thr Leu Pro Met Arg Ile Ser
 65                  70                  75                  80

Ser Ile Gly Ser Ala Pro Ser Ser Val Ser Tyr Arg Tyr Thr Gly Asn
                 85                  90                  95

Gly Val Tyr Asn Ala Ala Tyr Asp Ile Trp Leu Asp Pro Thr Pro Arg
            100                 105                 110

Thr Asn Gly Val Asn Arg Thr Glu Ile Met Ile Trp Phe Asn Arg Val
            115                 120                 125

Gly Pro Val Gln Pro Ile Gly Ser Pro Val Gly Thr Ala His Val Gly
        130                 135                 140

Gly Arg Ser Trp Glu Val Trp Thr Gly Ser Asn Gly Ser Asn Asp Val
145                 150                 155                 160

Ile Ser Phe Leu Ala Pro Ser Ala Ile Ser Trp Ser Phe Asp Val
            165                 170                 175

Lys Asp Phe Val Asp Gln Ala Val Ser His Gly Leu Ala Thr Pro Asp
            180                 185                 190

Trp Tyr Leu Thr Ser Ile Gln Ala Gly Phe Glu Pro Trp Glu Gly Gly
        195                 200                 205

Thr Gly Leu Ala Val Asn Ser Phe Ser Ser Ala Val Asn Ala
210                 215                 220

<210> SEQ ID NO 14
<211> LENGTH: 222
<212> TYPE: PRT
<213> ORGANISM: Artificial Sequence
<220> FEATURE:
<223> OTHER INFORMATION: synthetic Streptomyces lividans endoglucanase
      Cel12 catalytic domain

<400> SEQUENCE: 14

Asp Thr Thr Ile Cys Glu Pro Phe Gly Thr Thr Thr Ile Gln Gly Arg
  1               5                  10                  15

Tyr Val Val Gln Asn Asn Arg Trp Gly Ser Thr Ala Pro Gln Cys Val
             20                  25                  30

Thr Ala Thr Asp Thr Gly Phe Arg Val Thr Gln Ala Asp Gly Ser Ala
            35                  40                  45

Pro Thr Asn Gly Ala Pro Lys Ser Tyr Pro Ser Val Phe Asn Gly Cys
 50                  55                  60

His Tyr Thr Asn Cys Ser Pro Gly Thr Asp Leu Pro Val Arg Leu Asp
 65                  70                  75                  80

Thr Val Ser Ala Ala Pro Ser Ser Ile Ser Tyr Gly Phe Val Asp Gly
                 85                  90                  95

Ala Val Tyr Asn Ala Ser Tyr Asp Ile Trp Leu Asp Pro Thr Ala Arg
            100                 105                 110

Thr Asp Gly Val Asn Gln Thr Glu Ile Met Ile Trp Phe Asn Arg Val
            115                 120                 125

Gly Pro Ile Gln Pro Ile Gly Ser Pro Val Gly Thr Ala Ser Val Gly
        130                 135                 140

Gly Arg Thr Trp Glu Val Trp Ser Gly Gly Asn Gly Ser Asn Asp Val
145                 150                 155                 160

Leu Ser Phe Val Ala Pro Ser Ala Ile Ser Gly Trp Ser Phe Asp Val
            165                 170                 175

Met Asp Phe Val Arg Ala Thr Val Ala Arg Gly Leu Ala Glu Asn Asp
            180                 185                 190
```

```
Trp Tyr Leu Thr Ser Val Gln Ala Gly Phe Glu Pro Trp Gln Asn Gly
        195                 200                 205

Ala Gly Leu Ala Val Asn Ser Phe Ser Ser Thr Val Glu Thr
    210                 215                 220

<210> SEQ ID NO 15
<211> LENGTH: 218
<212> TYPE: PRT
<213> ORGANISM: Artificial Sequence
<220> FEATURE:
<223> OTHER INFORMATION: synthetic Trichoderma reesei endoglucanase
      Cel12 catalytic domain

<400> SEQUENCE: 15

Gln Thr Ser Cys Asp Gln Trp Ala Thr Phe Thr Gly Asn Gly Tyr Thr
1               5                   10                  15

Val Ser Asn Asn Leu Trp Gly Ala Ser Ala Gly Ser Gly Phe Gly Cys
            20                  25                  30

Val Thr Ala Val Ser Leu Ser Gly Gly Ala Ser Trp His Ala Asp Trp
        35                  40                  45

Gln Trp Ser Gly Gly Gln Asn Asn Val Lys Ser Tyr Gln Asn Ser Gln
    50                  55                  60

Ile Ala Ile Pro Gln Lys Arg Thr Val Asn Ser Ile Ser Ser Met Pro
65                  70                  75                  80

Thr Thr Ala Ser Trp Ser Tyr Ser Gly Ser Asn Ile Arg Ala Asn Val
                85                  90                  95

Ala Tyr Asp Leu Phe Thr Ala Ala Asn Pro Asn His Val Thr Tyr Ser
            100                 105                 110

Gly Asp Tyr Glu Leu Met Ile Trp Leu Gly Lys Tyr Gly Asp Ile Gly
        115                 120                 125

Pro Ile Gly Ser Ser Gln Gly Thr Val Asn Val Gly Gly Gln Ser Trp
    130                 135                 140

Thr Leu Tyr Tyr Gly Tyr Asn Gly Ala Met Gln Val Tyr Ser Phe Val
145                 150                 155                 160

Ala Gln Thr Asn Thr Thr Asn Tyr Ser Gly Asp Val Lys Asn Phe Phe
                165                 170                 175

Asn Tyr Leu Arg Asp Asn Lys Gly Tyr Asn Ala Ala Gly Gln Tyr Val
            180                 185                 190

Leu Ser Tyr Gln Phe Gly Thr Glu Pro Phe Thr Gly Ser Gly Thr Leu
        195                 200                 205

Asn Val Ala Ser Trp Thr Ala Ser Ile Asn
    210                 215

<210> SEQ ID NO 16
<211> LENGTH: 4
<212> TYPE: PRT
<213> ORGANISM: Artificial Sequence
<220> FEATURE:
<223> OTHER INFORMATION: synthetic N-terminal DTSM spacer

<400> SEQUENCE: 16

Asp Thr Ser Met
1
```

ENDOGLUCANASES

CROSS-REFERENCE TO RELATED APPLICATIONS

This application is a continuation of application Ser. No. 12/751,985 filed Mar. 31, 2010, which claims benefit of provisional application No. 61/165,312 filed Mar. 31, 2009. The entire contents of each application are incorporated herein by reference.

FIELD OF THE INVENTION

This invention relates to variant endoglucanase polypeptides and to new methods for saccharification.

BACKGROUND OF THE INVENTION

Cellulosic biomass is a significant renewable resource for the generation of sugars. Fermentation of these sugars can yield numerous end-products such as fuels and chemicals. While the fermentation of sugars to fuels such as ethanol is relatively straightforward, the hydrolytic conversion of cellulosic biomass to fermentable sugars such as glucose, generally referred to as "saccharification," is difficult because of the crystalline structure of cellulose and its close association with lignin (Ladisch et al., 1983, *Enzyme Microb. Technol.* 5:82). Pretreatment, by methods including, but not limited to, mechanical and chemical treatments increases the susceptibility of cellulose to hydrolysis, presumably by breaking the lignin seal and disrupting the crystalline cellulose structure. This step may be followed by the enzymatic conversion of cellulose to glucose, cellobiose, cello-oligosaccharides and the like using enzymes that break β-1-4 glycosidic bonds of cellulose. These enzymes are collectively referred to as "cellulases."

Cellulases are divided into three sub-categories of enzymes: 1,4-β-D-glucan glucanohydrolase ("endoglucanase" or "EG"); 1,4-β-D-glucan cellobiohydrolase ("exoglucanase", "cellobiohydrolase", or "CBH"); and β-glucosidase ("β-D-glucoside-glucohydrolase", "cellobiase" or "BG"). See Methods in Enzymology, 1988, Vol. 160, p. 200-391 (Eds. Wood, W. A and Kellogg., S. T.). These enzymes act in concert to catalyze the hydrolysis of cellulose containing substrates. Endoglucanases randomly attack the interior parts and mainly the amorphous regions of cellulose, mostly yielding shorter cellulose chains. Exoglucanases incrementally shorten the glucan molecules by binding to the glucan ends and releasing mainly cellobiose, a water-soluble β-1,4-linked dimer of glucose, from the ends of the cellulose polymer. β-glucosidases split the cellobiose into two units of glucose.

Most cellulases have a multidomain structure consisting of a core domain separated from a cellulose binding domain (CBD) by a linker peptide (Suumakki et al., 2000, *Cellulose* 7:189-209). The core or catalytic domain contains the active site (van Tilbeurgh et al., 1986, *FEBS Lett.* 16:215; Tomme et al., 1988, *Eur. J. Biochem.* 170:575-81).

There are several types of microorganisms that produce cellulases. These include fungi, actinomycetes, and bacteria. Cellulases from strains of the filamentous fungi *Trichoderma* sp., *Penicillium* sp., *Myceliophthora* sp. and *Chrysosporium* sp. have been particularly productive in hydrolyzing cellulose, and cellulases derived from these strains have been previously used to hydrolyze cellulose. However, the cost of producing these enzymes along with their hydrolytic inefficiency under certain industrial conditions has been a drawback.

In order to maximize the hydrolysis of cellulosic substrates and enable commercial routes to end-product production (e.g., biofuels), it would be highly desirable to develop new cellulases and particularly new endoglucanases useful in the saccharification of biomass. The invention described herein fulfills these and other needs, as will be apparent upon review of the following disclosure.

In addition to being useful in the hydrolysis of biomass feedstock, cellulases have other industrial applications. Cellulases are useful in the pulp and paper industry, the textile industry, as detergent components, and as additives in animal feeds. The cellulases of the present invention may be useful in these applications as well.

BRIEF SUMMARY OF THE INVENTION

In one aspect, this invention provides variant endoglucanases having improved properties. In some aspects, the variant endoglucanases are superior to naturally occurring endoglucanases under conditions required for saccharification of cellulosic feedstock.

In a second aspect, the invention provides improved methods for saccharification of cellulosic feedstock. In these methods the yield stress of a cellulose-containing mixture is reduced by treatment with endoglucanase, followed by treatment with other cellulase enzymes.

In yet another aspect, the invention provides signal peptides that are useful for expression and secretion of heterologous proteins, such as endoglucanses, in host cells, such as *Bacillus* species.

In one aspect, the invention relates to an isolated variant endoglucanase comprising a catalytic domain with at least about 70%, at least about 80%, at least about 85%, at least about 88% identity, or at least about 89%, 90%, 91%, 92%, 93%, 94%, 95%, 96%, 97%, 98%, or 99% identity to SEQ ID NO:1 and an amino acid substitution or deletion at one or more of the following positions D1, S10, T12, Q14, G15, A29, T33, D36, S37, I41, Q43, V48, T50, N51, A53, V60, N68, S74, A77, Q78, L79, S80, T81, V82, S83, Y91, S95, M98, A102, T110, R118, I121, V131, S136, A141, T142, Q147, S152, A165, S167, S171, Q182, V184, S185, G187, L188, Q190, N191, V198, P204, Q206, N207, T219 and/or T222 in SEQ ID NO:1. In one embodiment, the variant endoglucanases will have improved enzymatic performance compared to the enzymatic performance of the endoglucanase of SEQ ID NO: 1 or SEQ ID NO: 2 under desired pH and temperature conditions. In some embodiments, the pH conditions will be in the range of pH 3 to 10. In one embodiment, the pH conditions will be in the range of pH 4.0 to 5.5. In other embodiments, the temperature conditions will be in the range of 60° C. to 75° C., 60° C. to 80° C., 70° C. to 85° C., 75° C. to 90° C., or 75° C. to 95° C. In some embodiments the catalytic domain has at least 88% identity to SEQ ID NO:1.

In a further aspect, the invention relates to an isolated variant endoglucanase comprising a substitution at a position corresponding to one or more of residues D1(E/G/V), S10(F/H/L/T/W/Y), T12(I/V), Q14(E/K/L/P), G15N, A29(H/K/L/P/R/T), T33(A/E/H/I/L/Q/R/V), D36Y, S37E, I41V, Q43(E/K/L/M/R/V), V48K,T50(L/P), N51(H/K/S), A53(G/P), V60I, N68(H/I/K/L/V), S74(A/E/H/K/L/N/P/Q/R/T/V), A77V, Q78K, L79I, S80K, T81(K/N/Q/R/S), V82I, S83(E/I/R/V), Y91(C/F), S95(D/H/K/N/T), M98(I/K/Q/T/V), A102S, T110(E/K), R118(K/Q), I121 L, V131(E/I/M), S136 (D/E/H/K/R/T/V), A141(D/S/T), T142(C/F/H/M/N/S/V/W), Q147(R/S), S152(I/L/M/V), A165S, S167(D/I), S171T, Q182(I/V), V184F, G187E, L188F, Q190(D/H), S185(D/E/G/H/I/K/L/N/Q/R/T/V/Y), N191(P/Q/Y), V198I, P204L, Q206(E/R/S/V), N207(D/G), T219(A/C/D/E/Q), and/or T222K in SEQ ID NO:1. In some embodiments the variant endonuclease comprises a catalytic domain with at least about 70%, at least about 80%, at least about 85%, at least about 88% identity, or at least about 89%, 90%, 91%, 92%, 93%, 94%, 95%, 96%, 97%, 98%, or 99% identity to SEQ ID NO:1 and one of more of the substitutions above. In some embodiments the catalytic domain has at least 88% identity to SEQ ID NO:1.

In other aspects, the invention relates to an isolated endoglucanase with a catalytic domain comprising at least 80% sequence identity to the *Streptomyces avermitilis* endoglucanase catalytic domain (SEQ ID NO:1); and an amino acid substitution at a position corresponding to one or more of positions D1, S10, T12, Q14, G15, A29, T33, D36, S37, I41, Q43, V48, T50, N51, A53, V60, N68, S74, A77, Q78, L79, S80, T81, V82, S83, Y91, S95, M98, A102, T110, R118, I121, V131, S136, A141, T142, Q147, S152, A165, S167, S171, Q182, V184, S185, G187, L188, Q190, N191, V198, P204, Q206, N207, T219 and/or T222 in SEQ ID NO:1. In some embodiments the variant endoglucanase polypeptide is derived from, and has improved catalytic activity relative to, a catalytic domain homolog of SEQ ID NO:1. In some embodiments the variant endoglucanase polypeptide includes a cellulose binding domain. In some embodiments the endoglucanase catalytic domain and the cellulose binding domain are from the same parent endoglucanase. In some embodiments the variant endonuclease comprises a catalytic domain about at least about 88% identity, or at least about 88%, 89%, 90%, 91%, 92%, 93%, 94%, 95%, 96%, 97%, 98%, or 99% identity to SEQ ID NO:1.

In other aspects, the invention relates to an isolated endoglucanase including the sequence of SEQ ID NO: 7 or a variant of SEQ ID NO: 7 having at least 95% sequence identity to SEQ ID NO:7 and one or more amino acid substitutions in a position corresponding to positions T12, V48, N68, Q78, L79, T81, S152, S185, and/or Q206 in SEQ ID NO: 7.

In some embodiments the variant endonuclease comprises a catalytic domain with at least about at least about 88% identity, or at least about 89%, 90%, 91%, 92%, 93%, 94%, 95%, 96%, 97%, 98%, or 99% identity to SEQ ID NO:8.

In another aspect, the invention relates to a polynucleotide sequence encoding an isolated variant endoglucanase polypeptide of the invention, for example comprising a catalytic domain with at least about 70%, at least about 80%, at least about 85%, at least about 88% identity, or at least about 89%, 90%, 91%, 92%, 93%, 94%, 95%, 96%, 97%, 98%, or 99% identity to SEQ ID NO:1 and an amino acid substitution or deletion at one or more of the following positions D1, S10, T12, Q14, G15, A29, T33, D36, S37, I41, Q43, V48, T50, N51, A53, V60, N68, S74, A77, Q78, L79, S80, T81, V82, S83, Y91, S95, M98, A102, T110, R118, I121, V131, S136, A141, T142, Q147, S152, A165, S167, S171, Q182, V184, S185, G187, L188, Q190, N191, V198, P204, Q206, N207, T219 and/or T222 in SEQ ID NO:1. In some embodiments the catalytic domain has at least 88% identity to SEQ ID NO:1.

In a further embodiment, the invention relates to a polynucleotide sequence which encodes a variant endoglucanase having an amino acid substitution at a position corresponding to one or more of residues D1(E/G/V), S10(F/H/L/T/W/Y), T12(I/V), Q14(E/K/L/P), G15N, A29(H/K/L/P/R/T), T33(A/E/H/I/L/Q/R/V), D36Y, S37E, I41V, Q43(E/K/L/M/R/V), V48K, T50(L/P), N51(H/K/S), A53(G/P), V60, N68(H/I/K/L/V), S74(A/E/H/K/L/N/P/Q/R/T/V), A77V, Q78K, L79I, S80K, T81(K/N/Q/R/S), V82I, S83(E/I/R/V), Y91(C/F), S95 (D/H/K/N/T), M98(I/K/Q/T/V), A102S, T110(E/K), R118 (K/Q), I121 L, V131(E/I/M), S136(D/E/H/K/R/T/V), A141 (D/S/T), T142(C/F/H/M/N/S/V/W), Q147(R/S), S152(I/L/M/V), A165S, S167(D/I), S171T, Q182(I/V), V184F, G187E, L188F, Q190(D/H), N191(P/Q/Y), S185(D/E/G/H/I/K/L/N/Q/R/T/V/Y), V198I, P204L, Q206(E/R/S/V), N207(D/G), T219(A/C/D/E/Q), and/or T222K in SEQ ID NO:1. In some embodiments the variant endonuclease comprises a catalytic domain with at least about 70%, at least about 80%, at least about 85%, at least about 88% identity, or at least about 89%, 90%, 91%, 92%, 93%, 94%, 95%, 96%, 97%, 98%, or 99% identity to SEQ ID NO:1 and one of more of the substitutions above.

In some embodiments, the invention relates to an isolated variant endoglucanase comprising a catalytic domain with at least about 70%, at least about 80%, at least about 85%, at least about 88% identity, for example, or at least about 89%, 90%, 91%, 92%, 93%, 94%, 95%, 96%, 97%, 98%, or 99% identity to SEQ ID NO:3.

In yet another aspect, the invention relates to a vector comprising a polynucleotide described herein operably linked to a promoter.

In a further aspect, the invention relates to a host cell transformed with a polynucleotide or vector encoding a variant endoglucanase as described herein. In some embodiments, the host cell is a filamentous fungal cell and in other embodiments the host cell is a bacterial cell such as a *Bacillus* cell. In still a further aspect, the invention relates to a method of producing a variant endoglucanase as described herein comprising culturing a host cell transformed with a vector encoding a variant endoglucanase under conditions sufficient to produce the endoglucanase and obtaining the produced endoglucanase.

In other aspects, the invention relates to a method of converting biomass to fermentable sugars comprising contacting a variant endoglucanase as described herein with a biomass substrate under suitable conditions to produce fermentable sugars. In one embodiment, the fermentable sugars are contacted either separately or concurrently with a microorganism in a fermentation to produce end-products. In a further embodiment, the microorganism is a yeast and the end-product is an alcohol (e.g., ethanol). In yet another embodiment the fermentation is a simultaneous saccharification and fermentation process (SSF) and in other embodiments the saccharification and fermentation steps are consecutive.

In additional aspects, the invention relates to enzyme compositions comprising a variant endoglucanase of the present invention. In some embodiments, the enzyme composition is used in a composition for a saccharification application. In some embodiments, the enzyme composition is used in an application for treating textiles. In further embodiments, the enzyme composition is used in an application for treating pulp or paper. In yet other embodiments, the enzyme composition is used in a cleaning application (e.g. a detergent composition). In other embodiments, the enzyme composition may be used as a feed additive. In additional embodiments, the enzyme composition comprising a variant endoglucanase of the invention will include other enzymes (e.g. one or more other cellulases).

BRIEF DESCRIPTION OF THE DRAWINGS

FIG. 1 depicts (A) the amino acid sequence comprising the catalytic domain (CatD) of wild-type *Streptomyces avermitilis* endoglucanse (EG) (SEQ ID NO: 1); (B) the amino acid sequence of "CDX-SavOcat" (SEQ ID NO: 2), which is the wild-type *Streptomyces avermitilis* EG CatD, as modified by addition of an N-terminal spacer DTSM (SEQ ID NO: 16);

and (C) the amino acid sequence of wild-type *Streptomyces avermitilis* EG, which includes a signal peptide and cellulose binding domain having GenBank accession NP_821730 (SEQ ID NO: 3).

FIG. 2 depicts (A) SEQ ID NO: 4 which is a codon-optimized polynucleotide sequence coding for native *Streptomyces avermitilis* EG catD and cellulose binding domain, and (B) SEQ ID NO: 5 which is the codon optimized polynucleotide sequence coding for wild-type *Streptomyces avermitilis* EG catD and cellulose binding domain with an N-terminal spacer provided.

Figure 3:
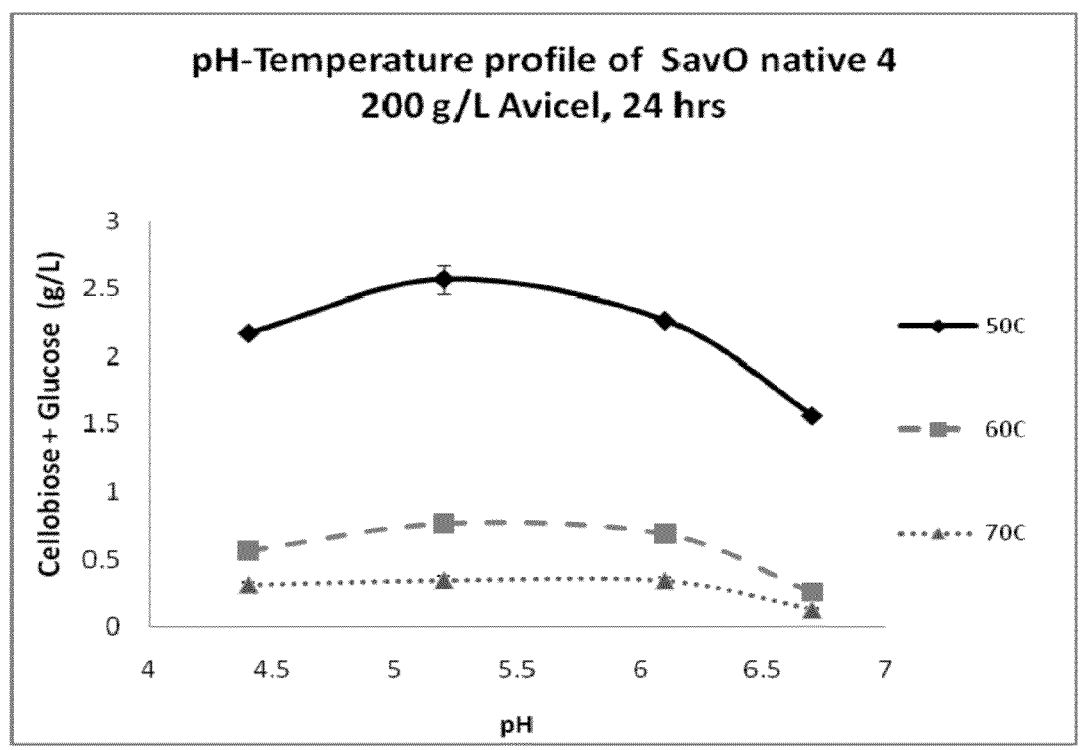

FIG. 3 illustrates the activity profile of CDX-SavOcat (SEQ ID NO: 2) at 50° C., 60° C., and 70° C., and pH (4.4-6.8) using Avicel (200 g/L) as a substrate under high throughput conditions. The production of cellobiose and glucose was measured by HPLC. CDX-SavOcat (SEQ ID NO: 2) exhibited optimum activity at pH 5 and 50° C., and detectable endoglucanse activity was observed at pH 4.4 and 70° C.

Figure 4:
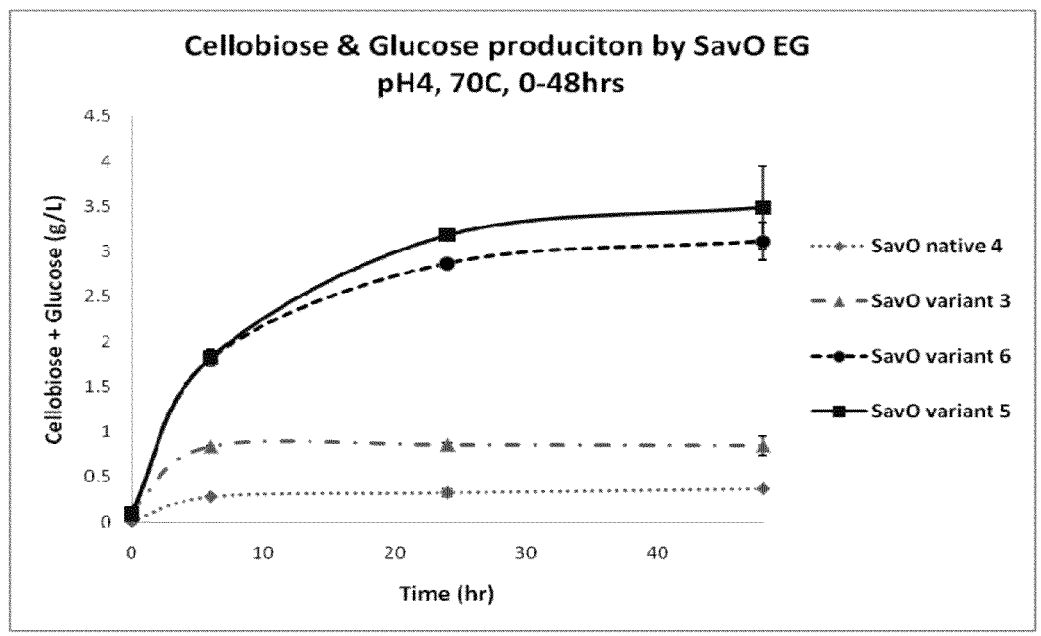

FIG. 4 illustrates the production of cellobiose and glucose over 48 hrs by various SavO EG variants. Conditions: 200 g/l Avicel, pH 4, 70° C. N=3, Error bars represent ±1 standard deviation.

Figure 5:
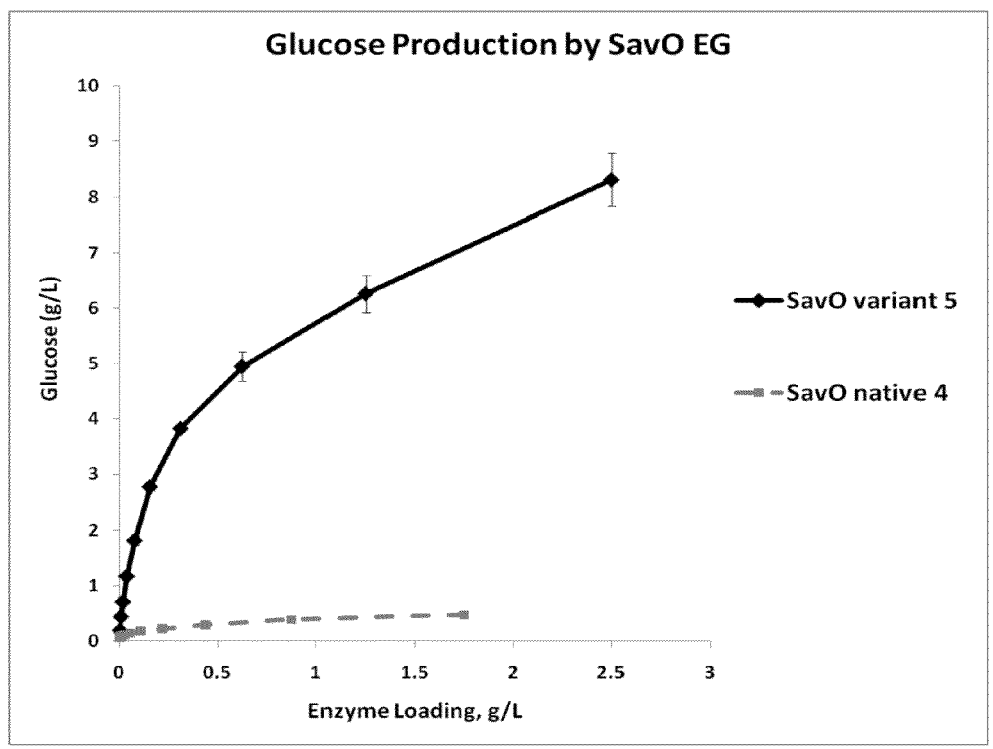

FIG. 5 shows production of glucose over 48 hrs by the CDX-SavOcat (SEQ ID NO: 2) and SavO variant 5 (SEQ ID NO: 8). Conditions: 200 g/l Avicel, pH 5, 65° C. N=3, Error bars represent ±1 standard deviation.

Figure 6:
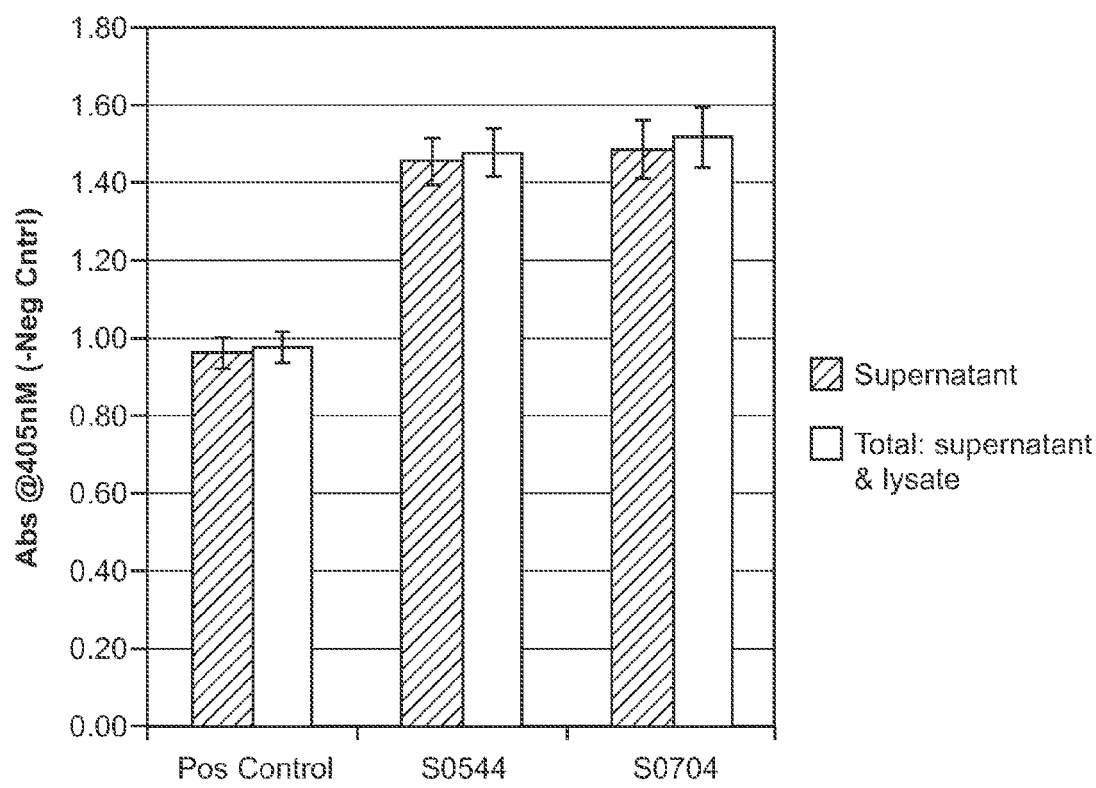

FIG. 6 shows high levels of production of a SavO endoglucanase variant linked to a *B. megaterium* signal peptide (SEQ ID NO: 9). Positive control: *B. megaterium* optimized signal peptide. Assay conditions: 5 mM pNPC, pH 5, 45° C. for 1 hr.

DETAILED DESCRIPTION

I. Overview

Current methods for production of ethanol and other valuable compounds from cellulosic feedstock generally requires three processes:

a) Pretreatment of the feedstock;
b) Hydrolysis of cellulose in the feedstock to produce soluble sugars (saccharification);
c) Fermentation of the sugars to produce a desired product, and recovery of the product.

The present invention relates, in part, to the second process, enzymatic hydrolysis of cellulose in the pre-treated feedstock to produce fermentable soluble sugars. Section II, below, provides definitions of selected terms used in this disclosure. In Section III, below, a novel saccharification process is described in which, inter alia, an endoglucanase is combined with cellulosic biomass and subsequently treated with other cellulase enzymes. In Section IV, variant endoglucanase proteins with desirable properties are described. These endoglucanases may be used in the saccharification process described in Section III, as well as for many other purposes. Section IV also describes a signal peptide sequence that, when fused to a heterologous polypeptide sequence, results in high levels of secretion from bacterial hosts such as *Bacillus* species, and particularly *B. megaterium*. The signal peptide may be used for production of endoglucanses described in Section III, as well as for expression of other cellulases and non-cellulase proteins. Section V provides experimental examples, including methods that may be used in carrying out the invention.

It will be understood that the specification is organized into separate sections solely for clarity, and that disclosures in any section may be combined with disclosures in any other section(s). For example, the feedstocks listed in Section II may be used in the processes described in Section III, the processes described in Section III may be carried out using the EG variants described in Section IV, etc.

II. DEFINITIONS

Unless defined otherwise, all technical and scientific terms used herein generally have the same meaning as commonly understood by one of ordinary skill in the art to which this invention belongs. Generally, the nomenclature used herein and the laboratory procedures in analytical chemistry, cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications.

The invention makes use of various conventional methods in molecular biology, cell culture, rheology, and enzymology. For techniques used in genetic engineering, see, e.g., Sambrook et al., 2001, *Molecular Cloning: A Laboratory Manual*, 3rd Ed., Cold Spring Harbor Laboratory Press, Cold Spring Harbor, N.Y. and Ausubel, ed., *Current Protocols in Molecular Biology*, 1990-2008, John Wiley Interscience. Standard techniques, or modifications thereof, are used for chemical syntheses and chemical analyses.

"Biomass," "cellulosic substrate," "cellulosic feedstock," and "feedstock" are used interchangeably herein to refer to materials that contain cellulose. Biomass can be derived from plants, animals, or microorganisms, and may include agricultural and forestry residues, industrial wastes, and terrestrial and aquatic crops grown for energy purposes. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, and flowers.

A "pretreated cellulosic feedstock" is a cellulose-containing material treated using methods known in the art, such as chemical, physical and biological pretreatments (e.g., mechanical breaking, steam explosion, pulping, grinding, acid hydrolysis, solvent exposure, and the like) to increase the susceptibility of cellulose to hydrolysis.

"SavO EG" refers to *Streptomyces avermitilis* endoglucanase.

"Catalytic Domain" or "CatD" refers to the structural region of a polypeptide which includes the active site for substrate hydrolysis. The amino acid sequence of the *Streptomyces avermitilis* endoglucanase "SavO-EG" of SEQ ID NO:1 includes the CatD.

The term "cellulase" refers to a category of enzymes capable of hydrolyzing cellulose (β-1,4-glucan or β-D-glucosidic linkages) to shorter cellulose chains, oligosaccharides, cellobiose and/or glucose.

"Endoglucanase" or "EG" refers to a class of cellulases (E.C.3.2.1.4) that hydrolyze internal β-1,4 glucosidic bonds of cellulose.

"Exoglucanase", "exo-cellobiohydrolase" or "CBH" refers to a class of cellulases (E.C. 3.2.1.91) that hydrolyze cellobiose from the reducing or non-reducing end of cellulose.

"Beta-glucosidase" or "cellobiase" or "BGL" refers to a β-glucosidase glucohydrolase (E.C. 3.2.1.21) that catalyzes the hydrolysis of cellobiose to glucose.

A "complete cellulase" or a "cellulase mixture" refers to composition comprising CBH, EG and BGL cellulases. Cellulase mixtures are known (see, e.g., Viikari et al., 2007, "Thermostable enzymes in lignocellulose hydrolysis" *Adv Biochem Eng Biotechnol* 108:121-45, and US Pat. publications US 2009/0061484, US 2008/0057541, and US 2009/0209009 to Iogen Energy Corp., each of which is incorporated herein by reference for all purposes. Other examples include cellulases from, for example, *Trichoderma reesei*, *Acidothermus cellulolyticus*, *Thermobifida fusca*, *Humicola grisea*, *Myceliophthora thermophilia* and *Chrysosporium* sp.), combinations of engineered cellulase enzymes, and commercially available cellulase mixtures (e.g., ACCELLERASE™ 1000 (Danisco) ACCELLERASE™ 1500 (Danisco), CELLIC CTEC2 (Novozymes)).

"Coding sequence" refers to that portion of a nucleic acid that encodes for an amino acid sequence of a protein.

The term 'contacting" refers to the placing of a respective enzyme or respective microbe in sufficiently close proximity to a respective substrate to enable the enzyme or microorganism to convert the substrate to a product. Those skilled in the art will recognize that mixing a solution of an enzyme or a culture of microorganisms with the respective substrate will effect contacting.

The terms "culturing" and "cultivation" refer to growing a population of microbial cells under suitable conditions in a liquid or solid medium. In some embodiments, culturing refers to fermentative bioconversion of a cellulosic substrate to an end-product.

"Deletion" refers to modification of a polypeptide by removal of one or more amino acids compared to a reference polypeptide.

"Detergent" refers to a mixture that is intended for use in a wash medium for the laundering of soiled fabrics. Such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein the term "expression" includes any step involved in the production of a polypeptide including but not limited to, transcription, post-transcriptional modification, translation, post-translational modification and secretion.

"Feed additive" refers to the use of cellulases for the treatment of animal feed for purposes known in the art, e.g., to enhance food products and reduce fiber in grain during the grain wet milling process or dry milling process.

"Saccharification" refers to the process in which substrates (e.g., cellulosic biomass) are broken down via the action of cellulases to produce fermentable sugars (e.g. monosaccharides such as but not limited to glucose). "Saccharification" also refers to the process in which cellulosic substrates are hydrolyzed to produce soluble sugars (glucose and cellobiose).

"Fermentable sugars" means simple sugars (monosaccharides, disaccharides and short oligosaccharides) such as but not limited to glucose, xylose, galactose, arabinose, mannose and sucrose.

The term "soluble sugars" is used herein to refer to cellobiose and glucose.

As used herein, the term "fermentation" is used broadly to refer to the cultivation of a microorganism(s) that use simple sugars, such as fermentable or soluble sugars, as an energy source to obtain a desired product.

"Host cell" refers to a suitable host for an expression vector comprising DNA encoding a heterologous protein, such as a variant EG encompassed by the invention, and the progeny thereof. Host cells useful in the present invention are generally prokaryotic or eukaryotic hosts, including any transformable microorganism in which expression can be achieved.

"Improved enzymatic performance" and "increased catalytic activity" refer to an improved property of the variant endoglucanase polypeptides, which can be represented by a statistically significant increase in specific activity (e.g., product produced/time/weight protein) or a statistically significant increase in percent conversion of the substrate to the product as compared to the reference endoglucanase enzyme at conditions specified by pH and temperature as desired. Exemplary methods to determine enzyme activity are provided in the Examples and may include, but are not limited to, cellobiose production from crystalline cellulose as measure by HTP screening or HPLC. Any property relating to enzyme activity may be affected, including the classical enzyme properties of $K_m$, $V_{max}$ or $k_{cat}$, changes of which can lead to increased enzymatic activity.

"Improved properties" of an endoglucanse of the invention may include increased protein expression, thermoactivity, thermostability, pH activity, pH stability, product specificity, increased specific activity, substrate specificity, increased resistance to substrate or end-product inhibition, altered pH/temperature profile, and chemical stability.

The term "improved thermostability" as used herein means a variant enzyme displays an increase in "residual activity" relative to the wildtype enzyme. Residual activity is determined by exposing the variant enzyme and the reference (e.g., wild type) enzyme to stress conditions of elevated temperature for a period of time and then determining endoglucanse activity under conditions in which wild type enzyme normally has activity. For example, the endoglucanse activity of the enzyme exposed to stress conditions ("a") is compared to that of a control in which the enzyme is not exposed to the stress conditions ("b"), and residual activity is equal to the ratio a/b. A variant with increased thermostability will have greater residual activity than the wild type enzyme. In one embodiment the enzymes are exposed to stress conditions of 65° C. at pH 5 for 6 hrs, but any cultivation conditions described herein can be used.

The term "introduced" in the context of inserting a nucleic acid sequence into a cell means transfected, transduced or transformed (collectively "transformed") and includes reference to the incorporation of a nucleic acid sequence into a eukaryotic or prokaryotic cell wherein the nucleic acid is incorporated into the genome of the cell.

The term "transformed" or "transformation" used in reference to a cell means a cell has a non-native nucleic acid sequence integrated into its genome or as an episomal plasmid that is maintained through multiple generations.

"Isolated" refers to a biologically active endoglucanase that has been intentionally separated from its host cell using standard microbiological and recombinant techniques. The term also includes endoglucanases purified from its host cell components. For example, an "isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis).

"Polynucleotide" has its normal meaning in the art.

"Signal sequence" or "signal peptide" refers to a sequence of amino acids at the N-terminal portion of a protein that facilitates the secretion of the mature form of the protein outside of the cell. The mature form of the extracellular protein lacks the signal sequence which is cleaved off during the secretion process.

The term "pre-protein" refers to a protein including an amino-terminal signal peptide (or leader sequence) region attached. The signal peptide is cleaved from the pre-protein by a signal peptidase during the secretion process to result in the mature or secreted protein.

"Simultaneous Saccharification and Fermentation (SSF)" refers to the process in which fermentable sugars (e.g. glucose) that are broken down from cellulose in a saccharification reaction are simultaneously converted by fermentation to an end-product (e.g. alcohol such as but not limited to ethanol).

"Variant endoglucanase" or "engineered endoglucanase" refers to endoglucanases of the present invention that are derived by manipulation from a reference endoglucanase containing a catalytic domain. Variant endoglucanases may be constructed by modifying a DNA sequence that encodes, for example, the native mature endoglucanase from *Streptomyces avermitilis* fused to a desired signal peptide, transformation of that DNA sequence into a suitable host, and expression of the modified DNA sequence to produce the enzyme. Reference endoglucanases may be naturally occurring endoglucanases or recombinant variant endoglucanases.

The amino acid sequence of a variant endoglucanase is derived from a "precursor" or "parent" endoglucanase amino acid sequence by the substitution of one or more amino acids of the precursor/parent amino acid sequence.

A "vector" is a DNA construct for introducing a DNA sequence into a cell. A vector may be an expression vector that is operably linked to a suitable control sequence capable of effecting the expression in a suitable host of the polypeptide encoded in the DNA sequence. An "expression vector" has a promoter sequence operably linked to the DNA sequence (e.g., transgene) to drives expression in a host cell.

The term "wild-type" or "native" are used interchangeably herein and, when applied to a polypeptide or protein, means a polypeptide or protein expressed by a naturally occurring microorganism found in nature. Thus, "wild-type *Streptomyces avermitilis* EG" and "native *Streptomyces avermitilis* EG" are the same.

As used herein "a", "an", and "the" include plural references unless the context clearly dictates otherwise.

The term "comprising" and its cognates are used in their inclusive sense; that is, equivalent to the term "including" and its corresponding cognates.

A "corresponding residue" as used in the present invention refers to a residue present in a variant endoglucanase that exists in an equivalent position to that in SEQ ID NO:1 or SEQ ID NO: 7 as indicated by primary sequence homology, tertiary structural homology or functional equivalence. Thus, the residue number or residue position of a given polymer is designated with respect to a reference sequence (e.g., SEQ ID NO:1) rather than by the actual numerical position of the residue within the given amino acid or polynucleotide sequence. For example, a given amino acid sequence can be aligned to the reference sequence by introducing gaps to optimize residue matches between the two sequences. In these cases, although the gaps are present, the numbering of the residue in a variant endoglucanase sequence is made with respect to SEQ ID NO:1 to which it has been aligned. Sequence comparison algorithms and the precise parameters used for alignment are the same as used for sequence identity determination as it pertains to the variant endoglucanases of the present invention, and are described later in the detailed description.

"Identity" or "percent identity" in the context of two or more polypeptide sequences, refers to two or more sequences or subsequences that are the same or have a specified percentage of amino acid residues that are the same (i.e., share at least about 70%, at least about 80%, at least about 85%, at least about 88% identity, for example, or at least about 89%, 90%, 91%, 92%, 93%, 94%, 95%, 96%, 97%, 98%, or 99% identity over a specified region to a reference sequence), when compared and aligned for maximum correspondence over a comparison window, or designated region as measured using a sequence comparison algorithms or by manual alignment and visual inspection. Sequence comparison algorithms and the precise parameters used for sequence identity determination as it pertains to the variant endoglucanases of the present invention are described later in the detailed description.

As used herein, the term "slurry" refers to an aqueous mixture comprising suspended solids, including cellulose, derived from biomass.

The following nomenclature may by used to describe substitutions in a variant polypeptide (or nucleic acid) sequence relative to a parent sequence: "R-#" or "R-#-V", where "#" refers to the position in a reference sequence and to corresponding residues in a variant or homologous sequence, "R" refers to the amino acid at that position in the reference sequence, and "V" refers to the amino acid at that position in the variant sequence, using the IUPAC single letter designation. For example, for a variant endoglucanse described with reference to SEQ ID NO: 1, "S10" indicates that in the variant EG, the residue at the position corresponding to the serine at position 10 of SEQ ID NO: 1 is replaced with an amino acid other than serine, and "S10W" means that the residue at the position corresponding to the serine at position 10 of SEQ ID NO: 1 is replaced with tryptophan, with amino acid position being determined by optimal alignment of the variant sequence with SEQ ID NO:1. Thus, for SavO variant 5 (discussed below) "S10W" means that the residue at the position corresponding to residue 10 of SEQ ID NO: 1 is tryptophan (e.g., position 10 of SEQ ID NO:8). For a variant of a homologous EG domain, "S10W" means that in the variant the residue at the position corresponding to position 10 of SEQ ID NO: 1 is tryptophan. For example, in a *S. lividans* Cel12 EG variant, "S10W" means that the threonine residue at position 10 of SEQ ID NO: 14 is replaced by tryptophan. By aligning the amino acid sequences of variants and homologs to a reference SavO sequence (e.g., SEQ ID NO:1) it is possible to assign an amino acid position number to any amino acid residue in the variant or homolog. As will be apparent, "R-#-(V1/V2/ . . . $V_N$)" means that the residue in the variant at position # is selected from V1, V2, . . . $V_N$. In variants comprising multiple substitutions, modifications are separated by semicolons (:) or addition marks ("+"), e.g., "S10W;A29P; Q43R;" or "S10W+A29P+Q43R."

III. Improved Saccharification Process

In one aspect the invention provides a saccharification process in which soluble sugars such as glucose and cellobiose are efficiently produced from a starting material with high solids content (e.g., greater than 5%, greater than 10%, greater than 20%, greater than 25%, greater than 30%, or greater than 35% dry weight of pretreated biomass).

In one embodiment the process includes maintaining a slurry containing (i) a pretreated cellulosic feedstock and (ii) an endoglucanse, under first saccharification conditions for a time sufficient to reduce the yield stress of the slurry; then combining the slurry with beta-glucosidase and cellobiohydrolase enzymes and maintaining the slurry under second saccharification conditions for a time sufficient to increase the amount of soluble sugars in the slurry.

In an initial step of the process, an endoglucanase is combined with the feedstock in an aqueous solution to form a slurry. Typically one endoglucanase is combined with the feedstock, but addition of multiple endoglucanases is contemplated. Properties of various suitable endoglucanase are discussed below in this Section III, in Section IV, and throughout this disclosure.

The pH and composition (e.g., content of salts, metals, surfactants, and the like) of the slurry may be adjusted prior to, at the time of, or after addition of the endoglucanase to provide conditions hospitable to endoglucanase activity. As noted, the slurry may have a high solids content. However the method can be used to process mixtures having a wide range of solids content.

Generally the feedstock in the slurry will be pre-treated at least minimally (e.g., mechanically breaking up the biomass) and often pretreatment includes additional manipulation such as steam explosion, acid hydrolysis and the like). In some embodiments the endoglucanse may be added to a slurry containing minimally pretreated biomass and further pretreatment can continue during at least a portion of the first saccharification conditions.

Preferably, the slurry comprising the pretreated cellulosic feedstock and endoglucanse is substantially free of cellobiohydrolase and beta-glucosidase activities. There are a variety of ways to prepare a slurry that contains cellulosic material and an endoglucanase, but which is essentially free of other cellulases. In one approach an endoglucanase composition substantially free of cellobiohydrolases and beta-glucosidases is combined with a pretreated feedstock in the slurry. Equivalently, a culture medium or broth that contains an endoglucanase but which is substantially free of cellobiohydrolases and beta-glucosidases proteins may be combined with a pretreated feedstock. In another approach, cells that express and secret an endoglucanase, but not cellobiohydrolases and beta-glucosidases proteins, are cultured in the slurry with the cellulosic material. In another approach a cellulase composition (e.g., broth) that contains both an endoglucanase and other cellulases is combined with the feedstock under first saccharification conditions in which the non-endoglucanase cellulases have reduced activity. In this context, a cellulase (e.g., a cellobiohydrolase or beta-glucosidase) has reduced activity under a specified temperature and pH if the cellulase has less than 20% enzymatic activity, and preferably less than 10% enzymatic activity, relative to the cellulase activity at the optimum pH and temperature, after exposure for 15 minutes to the specified condition. In yet another approach a cellulase composition (e.g., broth) that contains both an endoglucanase and other cellulases is combined with the feedstock under first saccharification conditions in which the non-endoglucanase cellulases are inactive or are rapidly inactivated. In this context, a cellulase (e.g., a cellobiohydrolase or beta-glucosidase) is inactive under a specified temperature and pH if the cellulase has less than 5% enzymatic activity, and preferably less than 1% enzymatic activity, relative to the cellulase activity at the optimum pH and temperature, after exposure for 15 minutes to the specified condition. Cellobiohydrolase and beta-glucosidase activity can be measured using routine techniques, including the methods described in Examples 13 and 14 below.

In some embodiments a slurry may be considered substantially free of other cellulases if little or no cellobiohydrolase or beta-glucosidase activity is detectable. In some embodiments no cellobiohydrolase or beta-glucosidase activity is detectable other than any such activities attributable to the endoglucanase itself and/or contributed by endogenous cellyuases in the feedstock.

In some embodiments of the invention, a slurry may be considered substantially free of other cellulases when the proportion of EG in or added to the slurry is an significant excess of any catalytically active BGL and CBH polypeptides present.

In some embodiments of the invention, a slurry may be considered substantially free of other cellulases if the weight ratio of endoglucanase to non-endoglucanase cellulase (BGL plus CHB) is greater than 5:1, preferably greater than 10:1, preferably greater than 20:1, preferably greater than 50:1, more preferably greater than 100:1.

In some embodiments a slurry may be considered substantially free of other (non-EG) cellulases if at least 10%, preferably at least 20%, even more preferably at least 30% of the weight ratio of total extracellular protein is EG. Extracellular protein means protein that is not intracellular, and is usually primarily secreted protein.

In some embodiments the endoglucanse may be produced by an organism that expresses high levels of EG (for example, due to genetic engineering of the organism's genome) to boost recombinant EG activity and production but which also produces low levels (e.g., endogenous or wild-type levels) of BGL and CBH. In such embodiments the molar excess of EG to the combination of BGL+CBH may be at least about 5:1, at least about 10:1, at least about 20:1, at least about 50:1, at least about 100:1 or even at least about 500:1.

The slurry is maintained under first saccharification conditions for a time sufficient to reduce the yield stress of the slurry. "Yield stress" refers to the minimum stress (force/area) required to be applied before a slurry moves. Yield stress is defined as the stress at which the phase angle becomes greater than 45° when measured at 25° C. using routine rheological methodology. Exemplary methods for measuring yield stress known in the art and are described in Example 11, infra.

The first saccharification conditions are conditions under which the endoglucanase is active and, in some cases, may be close to the pH and temperature optimum for the endoglucanase used. Preferably the endoglucanase is thermophilic and the first saccharification conditions include a temperature greater than 50° C., such as in the range between 50° C. and 85° C., sometimes between 60° C. and 80° C., sometimes between 65° C. and 80° C., sometime between 70° C. and 80° C., and sometimes between 75° C. and 80° C. A wide range of pHs may be used, for example acid pH (pH<6), basic pH (pH>8) or neutral pH (pH 6-8). In some embodiments the first saccharification conditions comprise an acid pH (e.g., such as pH in the range 3-6, usually pH in the range 3.5-5).

Typically the time sufficient to reduce the viscosity or yield stress of the slurry is between 1 minute and 96 hours, and preferably is between 1 hour and 48 hours. Often the time is at least about 1 hour, at least about 2 hours, at least about 5 hours, at least about 10 hours, or at least about 12 hours, and less that about 36 hours or less than about 24 hours. In some embodiments the time is sufficient for a reduction in viscosity or yield stress of the slurry by at least 50% compared to the starting material (e.g., the slurry immediately before or immediately after addition of the endoglucanses), often by at least 80%, sometimes by at least 90%, and in some embodiments a reduction of at least 95%, or even at least 99%, is achieved. It is desirable that yield stress be less than 300 Pa, more preferably less than 100 Pa, even more preferably less than 30 Pa, and in some cases less than 10 Pa, to promote production of soluble sugars (glucose and cellobiose) as described hereinbelow. In addition, reducing yield stress improves the pumpability of the slurry. See, e.g., Roche et al., 2009, *Biotech and Bioengg* 104:290-300.

It will be understood that as the yield stress of a slurry is reduced, the viscosity of the slurry decreases. In exemplary embodiments the viscosity of a slurry, prior to endoglucanase treatment, is greater than $10^3$ Pa-s, greater than $10^4$ Pa-s, greater than $10^5$ Pa-s, or greater than $10^6$ Pa-s. In some embodiments the viscosity of the slurry is reduced during the time the slurry is maintained under first saccharification conditions by at least 10-fold, preferably at least 100-fold, and often by at least 500-fold. In some embodiments the viscosity of the slurry is reduced during the time the slurry is maintained under first saccharification conditions to less than about 1000 Pa s, often less than about 500 Pa s, most often less than about 100 Pa s, and sometimes less than about 50 Pa s.

It will be appreciated that temperature, and to a lesser extent pH, may change in the course of the process, for example, as a pretreated feedstock cools over time. Typically, the temperature and pH remain in the specified range for at least a time sufficient to reduce the yield stress.

Exemplary first saccharification conditions are 0.1 hours to 10 hours at 50° C.-75° C. and pH 3.5-5.

Following treatment with endoglucanase under first saccharification conditions, the slurry is combined with cellobiohydrolase(s) and beta-glucosidase(s) and is maintained under second saccharification conditions for a time sufficient to increase the amount of soluble sugars (glucose and cellobiose) in the slurry. The process of maintaining cellulosic material with endoglucanase is sometimes be referred to as a "first step" and the subsequent process of treating the product of the first step with other cellulases is sometimes referred to as a "second step."

In the second step, the partially hydrolyzed biomass produced in the first step is combined with one or more cellobiohydrolases and one or more beta-glucosidases and optionally other enzymes such as, for example, endoglucanases, proteases, hemicellulases, xyloglucanase, beta-xylosidase, endoxylanase, alpha-L-arabinofuranosidase, alpha-and glucuronidase. The cellulase may be a "complete," such as, for example, broth from *Trichoderma reesei* or *Penicillium pinophilum* (Singh et al., 2009, *Bioresour. Technol.* 100:6679-81) or commercially available products such as ACCELERASE™ 1000 (Danisco) and CELLUCLAST™ (Novozymes). Alternatively one or both of the cellobiohydrolase and beta-glucosidase may added as enriched or purified compositions. In another approach, cells expressing cellobiohydrolase and/or beta-glucosidase, or broth from such cells, may be added.

In some embodiments (as when a complete cellulase is used) an endoglucanase is added to the slurry along with cellobiohydrolase and beta-glucosidase in the second step. In such cases the endoglucanase may be the same as, or may be different from, the endoglucanase used in the first step.

Often the second saccharification conditions differ from the first saccharification conditions in temperature and/or pH and/or by addition or removal of compounds such as metals, surfactants, catalysts, water, and the like. For example, when the first saccharification conditions are unsuitable for the cellobiohydrolase(s) and/or beta-glucosidase(s) used in the second step, the slurry (i.e., the slurry in which the feedstock has been subjected to endoglucanse treatment under first saccharification conditions) may be modified after the first step (e.g., prior to or at the time of addition of the non-endoglucanse cellulases).

Example 12, below, illustrates that first and second steps may be carried out at different temperatures. In the example, the first (endoglucanase) step was carried out at 75° C., while the second (cellulase) step was carried out at 50° C. using ACCELLERASE™ 1000 (Danisco). ACCELLERASE™ 1000, an enzyme complex that contains exoglucanase, endoglucanase, hemi-cellulase and beta-glucosidase activities, is reported by the manufacturer to be inactivated at temperatures above 70° C. In some embodiments, the first (endoglucanase) step is carried out at higher temperature than the second (cellulase) step. In some embodiments, the first (endoglucanase) saccharification conditions are maintained for a time that is shorter than the time for which the second (cellulase) saccharification conditions are maintained.

Exemplary second saccharification conditions are 3 hours to 168 hours at 40° C.-80° C. at pH 3-10. In specific embodiments the second saccharification conditions are maintained 3 hours to 24 hours, 72 hours to 168 hours, or 24 hours to 120 hours. In specific embodiments the second saccharification conditions include a temperature in the range 25° C.-80° C., 40° C.-75° C., 40° C.-70° C., or 40° C.-60° C.

The first and second steps may be carried out in the same reactor. Alternatively, the first step may be carried out in a first reactor and the second step may be carried out in a second reactor. Using this approach the content of the first reactor may be pumped into the second reactor or may be transferred by other means. Alternatively, a continuous processing approach is used in which the EG is added to the feedstock at a first part of the flowpath and the CBH/BGL proteins are added to the partially digested cellulosic substrate at a second, downstream, part of the flowpath. It will be appreciated that the term "reactor", in the context used above, does not imply a particular structure. A large number of reactor systems are known that may be used, or adapted for, the present invention. See, e.g., Foody et al., WO 2006/063467, incorporated herein by reference. In one embodiment, pretreatment, first saccharification step, second saccharification step, and fermentation each occur in a different reactor.

In a less preferred embodiment, the EG is added in a first step (e.g., first reactor), the CBH is added in a second step (e.g., second reactor), and the BGL is added in a third step (e.g., third reactor).

The present method provides greater conversion of feedstock to soluble sugars (glucose and cellobiose) than conventional methods. As shown in Example 12, when pretreated baggase (200 g/L) was maintained for 24 h with an endoglucanase (0.25%) at pH 5.0 and 75° C., followed by incubation for 24 h with ACCELLERASE™ 1000 (1.75%) at pH 5.0 and 50° C., the % conversion of glucan to soluble sugars was significantly higher than achieved by incubation with ACCELLERASE™ 1000 (2%) at 50° C. for 48 h. This was particularly unexpected under the conditions of Example 12, because the cellulose binding domain of the SavO endoglucanase used in the experiment is rapidly cleaved from the catalytic domain of the EG after secretion of the enzyme, as demonstrated by mass spectrometry. In one embodiment, the amount of soluble sugar produced according to the present method is greater than the amount of soluble sugar produced in a reference saccharification process in which pretreated feedstock is maintained with equal amounts of the endoglucanase, beta-glucosidase and cellobiohydrolase under first saccharification conditions, or alternatively under second saccharification conditions, for a time equal to the combined time under first and second saccharification conditions according to the process of present method.

The endoglucanase used in the saccharification method of the invention may be, for example, from plants, bacteria or fungi, and may be naturally occurring, recombinantly produced, or a recombinant variant of a naturally occurring endoglucanase.

In some embodiments the endoglucanase is from a fungus, such as a filamentous fungus. Without intending to limit the invention, exemplary endoglucanases include those listed in Table 1, as well as enzymatically active variants with at least 70%, at least 80%, or at least 90% sequence identity to a listed endoglucanse.

In some embodiments the endoglucanase is from a bacterium, such as a *Streptomyces* species, e.g., *S. ambofaciens, S. achromogenes, S. avermitilis, S. coelicolor, S. aureofaciens, S. aureus, S. fungicidicus, S. griseus*, and *S. lividans*. Without intending to limit the invention exemplary endoglucanases include those listed in Table 1 as well as enzymatically active variants with at least 70%, at least 80%, or at least 90% sequence identity to a listed endoglucanase.

TABLE 1

| EG | Acc. No. | Reference |
| --- | --- | --- |
| T. reesei Cel12 | 1H8V | J. Mol. Biol. 308 (2), 295-310 (2001) |
| H. schweinitzii Cel12 | 1OA3 | Protein Sci. 12 (4), 848-860 (2003) |
| R. marinus Cel12 | 1H0B | J. Mol. Biol. 320 (4), 883-897 (2002) |
| S. sp. Cel12 | 1OA4 | Protein Sci. 12 (4), 848-860 (2003) |
| S. lividans Cel12 | 2NLR | Appl. Environ. Microbiol. 60 (5), 1701-1703 (1994) |

In some embodiments the endoglucanse is a naturally occurring *Streptomyces avermitilis* endoglucanse ("SavO") or an engineered SavO variant described in Section IV hereinbelow, including without limitation wild-type SavO and SavO variants listed in Tables 4A-C. In some embodiments the endoglucanse is a homolog of SavO and comprises one or more substitutions described in Section IV hereinbelow.

In one embodiment the endoglucanase comprises a catalytic domain having the sequence of SavO variant 2, 5, 6 or 7 as set forth Table 4A-C, below.

In some embodiments the endoglucanase is enzymatically active at high temperature (e.g., temperatures greater than 50° C., sometimes greater than 60° C., sometimes greater than 65° C. greater, and sometimes than 70° C.), and in some embodiments the endoglucanse has optimum activity at the high temperature.

In some embodiments the EG lacks a cellulose binding domain (CBD). For example, in some embodiments the cellulose binding domain of the endoglucanase is cleaved from the catalytic domain following secretion of the enzyme. Alternatively, engineered endoglucanases lacking a CBD may be used.

IV. Improved Endoducanses

In one aspect the present invention provides endoglucanases exhibiting high enzymatic activity at elevated temperatures. The endoglucanases of the invention are derived from an *Streptomyces avermitilis* endoglucanase (SavO EG) (SEQ ID NO:3) or a homolog of the SavO EG and comprise one or more substitutions relative to the naturally occurring sequence (e.g., native or wild-type SavO EG) as described hereinbelow. As noted above, endoglucanases and other cellulases generally have a multidomain structure comprising a catalytic domain (Cat) and a cellulose binding domain (CBD) by a linker peptide. The inventors have discovered that a proteolytic fragment of SavO EG comprising the catalytic domain but not the CBD retains enzymatic activity. Thus, in some embodiments the endoglucanases of the invention comprise a catalytic domain derived from the catalytic domain of a *Streptomyces avermitilis* endoglucanase (SavO EG) (SEQ ID NOS: 1 and 2) or from a homologous catalytic domain of a structurally related endoglucanase. In various embodiments the endoglucanases of the invention may comprise (i) an isolated EG catalytic domain, optionally comprising a short spacer at the amino- and/or carboxy terminus; (ii) an EG catalytic domain linked to a native CBD (e.g., the SavO CBD when a SavO catalytic domain is used; see, e.g., SEQ ID NO:3); (iii) an EG catalytic domain linked to a heterologous CBD with which the EG catalytic domain is not naturally associated (e.g., an EG catalytic domain linked to the CBD from *S. lividans* EG).

In some embodiments the endoglucanase comprises a catalytic domain with at least 70% sequence identity, sometimes at least 75%, sometimes at least 80%, sometimes at least 85%, sometimes at least 90%, sometimes at least 88%, sometimes at least 90%, sometimes at least 95% and sometimes at least 98% sequence identity to the *Streptomyces avermitilis* endoglucanase catalytic domain (SEQ ID NO: 1). In some embodiments the endoglucanases comprise catalytic domains with greater than or equal to 88% sequence identity to the catalytic domain of *Streptomyces avermitilis* endoglucanase (SavO EG) (SEQ ID NO:1 or SEQ ID NO: 2). In some embodiments the endoglucanse has complete sequence identity to the *Streptomyces avermitilis* endoglucanase catalytic domain (SEQ ID NO: 1), except for specified substitutions.

As described in the Examples, analyses of numerous variant endoglucanases has resulted in EGs with improved characteristics compared to the wild-type SavO EG. These improved characteristics include improved enzymatic performance under process conditions that are beneficial to the saccharification of biomass substrates.

The endoglucanases of the invention comprise one or more substitutions relative to the naturally occurring SavO EG sequence or naturally occurring SavO EG-homolog sequence. For example, The invention further encompasses EG variants listed in Tables 4A-4C as disclosed herein.

In some embodiments of the invention, the isolated variant EG polypeptides comprise an amino acid substitution or deletion at one or more of the following positions D1, S10, T12, Q14, G15, V18, A29, T33, D36, S37, I41, Q43, V48, T50, N51, A53, V60, N68, S74, A77, Q78, L79, S80, T81, V82, S83, Y91, S95, M98, A102, T110, R118, I121, V131, S136, A141, T142, Q147, S152, A165, S167, S171, Q182, V184, S185, G187, L188, Q190, N191, W193, V198, P204, Q206, N207, T219 and/or T222 in SEQ ID NO:1, wherein SEQ ID NO: 1 has the amino acid sequence of:

(SEQ ID NO: 1)
DTSICEPFGSTTIQGRYVVQNNRWGTSEAQCITATDSGFRITQADGSVPT

NGAPKSYPSVYNGCHYTNCSPGTSLPAQLSTVSSAPTSISYSYVSNAMYD

AAYDIWLDPTPRTDGVNRTEIMVWFNKVGSVQPVGSQVGTATVAGRQWQV

WSGNNGSNDVLSFVAPSAITSWSFDVMDFVRQAVSRGLAQNSWYLTSVQA

GFEPWQNGAGLAVTSFSSTVNT.

In some embodiments the variant EG having one or more substitutions comprises an amino acid sequence that is at least 88% identical to the amino acid sequence of SEQ ID NO: 1. In some embodiments the variant EG polypeptide will have at least 89%, at least 90%, at least 91%, at least 92% at least 93%, at least 95%, at least 96%, at least 97%, at least 98%, at least 99% sequence identity to SEQ ID NO: 1.

In some embodiments, the isolated variant EG comprises a substitution at a position corresponding to one or more of residues D1(E/G/V), S10(F/H/L/T/W/Y), T12(I/V), Q14(E/K/L/P), G15N, A29(H/K/L/P/R/T), T33(A/E/H/I/L/Q/R/V), D36Y, S37E, I41V, Q43(E/K/L/M/R/V), V48K,T50(L/P), N51(H/K/S), A53(G/P), V60I, N68(H/I/K/L/V), S74(A/E/H/

K/L/N/P/Q/R/T/V), A77V, Q78K, L79I, S80K, T81(K/N/Q/R/S), V82I, S83(E/I/R/V), Y91(C/F), S95(D/H/K/N/T), M98(I/K/Q/T/V), A102S, T110(E/K), R118(K/Q), I121 L, V131(E/I/M), 5136(D/E/H/K/R/T/V), A141(D/S/T), T142(C/F/H/M/N/S/V/W), Q147(R/S), S152(I/L/M/V), A165S, S167(D/I), S171T, Q182(I/V), V184F, S185(D/E/G/H/I/K/L/N/Q/R/T/V/Y), G187E, L188F, Q190(D/H), N191(P/Q/Y), V198I, P204L, Q206(E/R/S/V), N207(D/G), T219(A/C/D/E/Q), and/or T222K in SEQ ID NO:1.

In some embodiments, the variant EG will include at least 2, at least 3, at least 4, at least 5, at least 6, at least 7, at least 8, at least 9, at least 10, at least 11, at least 12, at least 13, at least 14, at least 15, at least 16 amino acid residues which have been substituted as compared to the amino acid sequence of SEQ ID NO: 1 or SEQ ID NO: 2.

In some embodiments, the variant EG of the invention will comprise a substitution in at least position S10, A29, A53, S74 or N191 as compared to SEQ ID NO: 1. In some embodiments, the variant will include substitutions in 2 of these positions, in 3 of these positions, in 4 of these positions and sometimes in all 5 of these positions. In some embodiments, a variant EG of the invention will comprise a substitution at S10(F/H/L/T/W/Y), A29(H/K/L/P/R/T), A53(G/P), S74(A/E/H/K/L/N/P/Q/R/T/V) and/or N191(P/Q/Y) as compared to SEQ ID NO: 1. In some embodiments, the variant EG of the invention in addition to having a substitution at any one of positions S10, A29, A53, S74 and/or N191 will further comprise a substitution at a position selected from one or more of T12, Q43, V48, N68, Q78, L79, T81, V82, M98, S152, S185, and Q206 as compared to SEQ ID NO: 1. In some embodiments, the substitution will be selected from T12(V/I), Q43(R), V48(K), N68(I), Q78(K), L79(I), T81(K/I), V82(I), M98(V), S152(M), S185(Q/V), and Q206(E) as compared to SEQ ID NO: 1.

In some embodiments, the variant EG will comprise a sequence having at least 95% sequence identity to SEQ ID NO: 6, wherein SEQ ID NO: 6 has the amino acid sequence of:

```
                                           (SEQ ID NO: 6)
DTSICEPFGSTTIQGRYVVQNNRWGTSEPQCITATDSGFRITQADGSVPT

NGPPKSYPSVYNGCHYTNCSPGTPLPAQLSTVSSAPTSISYSYVSNAMYD

AAYDIWLDPTPRTDGVNRTEIMVWFNKVGSVQPVGSQVGTATVAGRQWQV

WSGNNGSNDVLSFVAPSAITSWSFDVMDFVRQAVSRGLAQPSWYLTSVQA

GFEPWQNGAGLAVTSFSSTVNT
```

In some embodiments, the variant EG will comprise SEQ ID NO: 6 and in other embodiments the variant EG will include at least 1, at least 2, at least 3, at least 4, at least 5, at least 6, at least 7, or at least 8 further substitutions at a position corresponding to position S10, T12, Q43, V48, N68, Q78, L79, T81, V82, M98V, S152, and/or S185 in SEQ ID NO: 6. In some embodiments, the substitutions will correspond to S10(F/H/L/T/W/Y), T12(I/V), Q43(E/K/L/M/R/V), V48K, N68(H/I/K/L/V), Q78K, L79I, T81(K/N/Q/R/S), V82I, M98(I/K/Q/T/V), S152(I/L/M/V) and/or S185(D/E/G/H/I/K/L/N/Q/R/T/V/Y) in SEQ ID NO: 6.

In some embodiments, the variant EG of the invention will comprise at least 90%, at least 91%, at least 92%, at least 93%, at least 95%, at least 96%, at least 97%, at least 98%, and at least 99% amino acid sequence identity with SEQ ID NO: 7. In some embodiments, the variant EG of the invention is the EG comprising SEQ ID NO: 7, wherein SEQ ID NO: 7 has the amino acid sequence of

```
                                           (SEQ ID NO: 7)
DTSICEPFGWTTIQGRYVVQNNRWGTSEPQCITATDSGFRITRADGSVPT

NGPPKSYPSVYNGCHYTNCSPGTPLPAQLSTISSAPTSISYSYVSNAVYD

AAYDIWLDPTPRTDGVNRTEIMVWFNKVGSVQPVGSQVGTATVAGRQWQV

WSGNNGSNDVLSFVAPSAITSWSFDVMDFVRQAVSRGLAQPSWYLTSVQA

GFEPWQNGAGLAVTSFSSTVNT
```

In some embodiments, the variant EG will comprise an amino acid sequence having at least one substitution selected from position T12, V48, N68, Q78, L79, T81, S152, S185, and/or Q206 as compared to SEQ ID NO: 7. In some embodiments, the substitution will be selected from T12(V/I), Q43(R/E/K/L/M/V), V48(K), N68(H/I/K/L/V), Q78(K), L79(I), T81(K/N/Q/R/S), S152(I/L/M/V), S185(D/E/G/H/I/K/L/N/Q/R/T/V/Y), and/or Q206(E/R/S/V) as compared to SEQ ID NO: 7. In some embodiments, the variant EG of the invention will have at least 95% sequence identity to SEQ ID NO: 7.

In some embodiments, the variant EG of the invention is the EG comprising SEQ ID NO: 8, wherein SEQ ID NO: 8 has the amino acid sequence of:

```
                                           (SEQ ID NO: 8)
DTSICEPFGWTVIQGRYVVQNNRWGTSEPQCITATDSGFRITRADGSKPT

NGPPKSYPSVYNGCHYTICSPGTPLPAQISKISSAPTSISYSYVSNAVYD

AAYDIWLDPTPRTDGVNRTEIMVWFNKVGSVQPVGSQVGTATVAGRQWQV

WMGNNGSNDVLSFVAPSAITSWSFDVMDFVRQAVQRGLAQPSWYLTSVQA

GFEPWENGAGLAVTSFSSTVNT
```

In some embodiments, the variant EG will comprise SEQ ID NO: 8 and in other embodiments the variant EG will include at least 1, at least 2, at least 3, at least 4, at least 5, at least 6, at least 7, or at least 8 further substitutions or deletions in SEQ ID NO:8.

The invention also contemplates that substitutions may be introduced into endoglucanses of other bacterial and fungal species, at positions corresponding to the substituted positions of the S. avermitilis EG, to produce variants with similarly desirable properties.

For example, a number of bacteria (including but not limited to *Streptomyces, Micromonospora, Actinosynnema, Salinispora, Mycobacterium* species) express endoglucanses comprising catalytic domains with significant sequence identity to *Streptomyces avermitilis* EG catalytic domain. The present invention contemplates EG variants of these bacterial EGs in which substitutions are made at residues corresponding to the S. avermitilis positions and substitutions disclosed herein. Examples of bacterial EGs with significant sequence identity include, for example: *Streptomyces sviceus* ATCC 29083 (Accession No. ZP_05016224.1); *Streptomyces scabiei* 87.22 (Accession No. YP_003494465.1); *Streptomyces ghanaensis* ATCC 14672 (Accession No. ZP_04683886.1); *Streptomyces rochei* (Accession No. CAA52139.1); *Streptomyces griseoflavus* Tu4000 (Accession No. ZP_05536909.1); *Streptomyces xylophagus* (Accession No. ACN56471.1); *Streptomyces viridosporus* (Accession No. AAD25090.1); *Streptomyces scabiei* 87.22 (Accession No.

YP_003486364.1); *Streptomyces coelicolor* A3(2) (Accession No. NP_625477.1); *Streptomyces flavogriseus* ATCC 33331 (Accession No. ZP_05801764.1); *Streptomyces lividans* TK24 (Accession No. ZP_06532489.1); *Streptomyces halstedii* (Accession No. AAC45429.1); *Streptomyces ambofaciens* ATCC 23877 (Accession No. CAJ90159.1); *Streptomyces* sp. 11AG8 (Accession No. AAF91283.1); *Micromonospora aurantiaca* ATCC 27029 (Accession No. ZP_06215034.1); *Mycobacterium kansasii* ATCC 12478 (Accession No. ZP_04750212.1); *Micromonospora* sp. ATCC 39149 (Accession No. ZP_04607827.1); *Streptomyces* sp. SPB78 (Accession No. ZP_05488520.1); *Streptomyces* sp. SPB74 (Accession No. ZP_04994021.1); *Salinispora tropica* CNB-440 (Accession No. YP_001161230.1); *Actinosynnema mirum* DSM 43827 (Accession No. YP_003101698.1); *Salinispora arenicola* CNS-205 (Accession No. YP_001539639.1); *Mycobacterium kansasii* ATCC 12478 (Accession No. ZP_04747778.1).

Determination of sequence identity is determined by a sequence comparison algorithm. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters.

The algorithm used to determine whether a variant endoglucanase has a catalytic domain sequence identity to SEQ ID NO:1 is the BLAST algorithm, which is described in Altschul et al., 1990, *J. Mol. Biol.* 215:403-410. Software for performing BLAST analyses is publicly available through the National Center for Biotechnology Information (on the worldwide web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a word size (W) of 3, an expectation (E) of 10, and the BLOSUM62 scoring matrix (see Henikoff & Henikoff, 1989, *Proc. Natl. Acad. Sci. USA* 89:10915).

Table 2 provides an aligment of catalytic domains of SavO and 5 homologous EGs. The multiple sequence alignment was done using AlignX from Invitrogen (part of VectorNTI). It is based on the Clustal W algorithm.

TABLE 2

```
                           1                                                  50
T. reesei Cel12      (1)   -QTSCDQWATFTGNG--YTVSNNLWGASAGSGFGCVTA----VSLSGGAS
H. schweinitzii Cel12 (1)  -QTSCDQYATFSGNG--YIIVSNNLWGASAGSGFGCVTS----VSLNGAAS
R. marinus Cel12     (1)   TVELCGRWDARDVAGGRYRVINNVWGAETAQCIEVGLETGNFTITRADHD
S. sp. Cel12         (1)   NQQICDRYGTTTIQDR-YVVQNNRWGTSATQCINVTGNGFEITQADGSYP
S. lividans Cel12    (1)   DTTICEPFGTTTIQGR-YVVQNNRWGSTAPQCVTATDTGFRVTQADGSAP
SavO EG              (1)   DTSICEPFGSTTIQGR-YVVQNNRWGTSEAQCITATDSGFRITQADGSVP 51                                                 100
T. reesei Cel12      (44)  WHADWQWSGGQNNVKSYQNSQIAIPQKRTVNSISSMPTTASWSYSGSNIR
H. schweinitzii Cel12 (44) WHADWQWSGGQNNVKSYQNVQINIPQKRTVNSIGSMPTTASWSYSGSDIR
R. marinus Cel12     (51)  NGNNVAAYPAIYFGCHWGACTSNSGLPRRVQELSDVRTSWTLTPITT-GR
S. sp. 11AG8 Cel12   (50)  TNGAPKSYPSVYDGCHYGNCAPRTTLPMRISSIGSAPSSVSYRYTGN-GV
S. lividans Cel12    (50)  TNGAPKSYPSVFNGCHYTNCSPGTDLPVRLDTVSAAPSSISYGFVDG-AV
SavO EG              (50)  TNGAPKSYPSVYNGCHYTNCSPGTSLPAQLSTVSSAPTSISYSYVSN-AM 101                                                150
T. reesei Cel12      (94)  ANVAYDLFTAANPNHVTYSG-DYELMIWLGKYGDIGPIGSSQGTVNVGGQ
H. schweinitzii Cel12 (94) ANVAYDLFTAANPNHVTYSG-DYELMIWLGKYGDIGPIGSSQGTVNVGGQ
R. marinus Cel12     (100) WNAAYDIWFSPVTNSGNGYSGGAELMIWLNWNGGVMPGGSRVATVELAGA
S. sp. 11AG8 Cel12   (99)  YNAAYDIWLDPTPRTNGVN--RTEIMIWFNRVGPVQPIGSPVGTAHVGGR
S. lividans Cel12    (99)  YNASYDIWLDPTARTDGVN--QTEIMIWFNRVGPIQPIGSPVGTASVGGR
SavO EG              (99)  YDAAYDIWLDPTPRTDGVN--RTEIMVWFNKVGSVQPVGSQVGTATVAGR 151                                                200
T. reesei Cel12      (143) SWTLYYGYNGAMQVYSFVAQTNTTNYSGDVKNFFNYLRDNKGYNAAGQYV
H. schweinitzii Cel12 (143) TWTLYYGYNGAMQVYSFVAQSNTTSYSGDVKNFFNYLRDNKGYNAGGQYV
R. marinus Cel12     (150) TWEVWYADWDWNYIAYRRTTPTTSVSELDLKAFIDDAVA-RGYIRPEWYL
S. sp. 11AG8 Cel12   (147) SWEVWTGSNGSNDVISFLAPSAISSWSFDVKDFVDQAVS-HGLATPDWYL
S. lividans Cel12    (147) TWEVWSGGNGSNDVLSFVAPSAISGWSFDVMDFVRATVA-RGLAENDWYL
SavO EG              (147) QWQVWSGNNGSNDVLSFVAPSAITSWSFDVMDFVRQAVS-RGLAQNSWYL 201                            229
T. reesei Cel12      (193) LSYQFGTEPFTGSGTLNVASWTASIN---
H. schweinitzii Cel12 (193) LSYQFGTEPFTGSGTLNVASWTASIN---
R. marinus Cel12     (199) HAVETGFELWEGGAGLRSADFSVTVQKLA
S. sp. 11AG8 Cel12   (196) TSIQAGFEPWEGGTGLAVNSFSSAVNA--
```

TABLE 2-continued

```
S. lividans Cel12    (196)   TSVQAGFEPWQNGAGLAVNSFSSTVET--
SavO EG              (196)   TSVQAGFEPWQNGAGLAVTSFSSTVNT--
```

T. reesei Cel12 (SEQ ID NO: 15)
H. schweinitzii Cel12 (SEQ ID NO: 11)
R. marinus Cel12 (SEQ ID NO: 12)
S. sp. 11AG8 Cel12 (SEQ ID NO: 13)
S. lividans Cel12 (SEQ ID NO: 14)
SavO EG (SEQ ID NO: 1)

When the wild-type catalytic domain from *Streptomyces avermitilis* EG (SEQ ID NO: 1) is aligned with an EG from *Streptomyces lividans* they share 87% sequence identity as defined by the parameters described herein. In some embodiments, improved endoglucanase variants of the present invention have a catalytic domain with at least 88% identity to the wild-type catalytic domain of *S. avermitilis* endoglucanase (SEQ ID NO:1).

Cellulose Binding Domain

While the variant EGs of the present invention are defined by the catalytic domain, many cellulases include a cellulose binding domain and linker peptide (see, e.g., the wild-type or native full length SavO EG (SEQ ID NO: 3)). It is contemplated that in some embodiments a cellulase having endoglucanase activity which encompasses the variant EG of the invention will also include a linker and cellulase binding domain. In some embodiments, the linker and cellulose binding domain (collectively, "CDB") will be the CBD having the polypeptide sequence as depicted in FIG. 1C. In some embodiments, the CBD will have at least 90%, at least 93%, at least 95%, at least 96%, at least 97%, at least 98%, at least 99% sequence identity to the CBD as depicted in FIG. 1C. In some embodiments the variant EG will include one or more substitutions in the CBD, such as 1, 2, 3, 4, 5, or 6 substitutions in the CBD as depicted in FIG. 1C.

CBDs may be homologous or heterologous to the catalytic domain. A homologous CBD is associated in the wildtype EG with the parental catalytic domain. For example, the *Streptomyces avermitilis* EG CDB (see FIG. 1C) is homologous to the *Streptomyces avermitilis* EG catalytic domain.

Assessment of, and Properties of, Improved Variant Endoglucanases

Variant endoglucanases can be generated from a reference endoglucanase sequence using recombinant or synthetic methods. The properties (e.g., catalytic activity, pH and temperature tolerance and optimums, etc.) of variant endoglucanases of the invention can be compared to reference endoglucanases (which may be wildtype or other variants). The comparison may be quantitative or qualitative. For example, a variant endoglucanase once expressed from a host cell may be compared to the sequence of the wild-type SavO EG catalytic domain (SEQ ID NO: 1 or SEQ ID NO: 2) for improved properties. For example, the properties of a variant endoglucanase expressed from a host cell (e.g., a SavO EG variant having a catalytic domain with at least 88% sequence identity to SEQ ID NO: 1) may be compared to the reference endoglucanases comprising SEQ ID NO:1 (the catalytic domain of wild-type SavO EG) or SEQ ID NO:2 (which contains the wild-type SavO EG catalytic domain and 4 N-terminal amino acids).

The variant endoglucanases of the present invention such as those found in Table 4A-C can be screened to determine improved properties such as optimal activity at desired conditions. Various screening tests may be used by one skilled in the art. In one embodiment, variant endoglucanase candidates can be screened by a tier 1 colorimetric pNPC (p-nitrophenyl-6-D-cellobiosideybased HTP assay (substrate: pNPC; pH: 4.0; temperature: 70° C.; time: 24 hours). The release of p-nitrophenol is measure at 405 nm to calculate activity of the endoglucanase variants. Active variants identified from a tier1 assay can be subsequently subjected to a tier 2 HPLC assay (substrate: Avicel (crystalline cellulose) pH: 4.0-5.0; temperature: 60-70° C.; time: 24 hours) to identify improved variant endoglucanases. Production of cellobiose from cellulose containing substrates can be measured by HPLC. Improved endoglucanase variants may further be confirmed and validated under saccharification process conditions. Cellobiose and glucose production under saccharification process conditions are measured by HPLC.

Some variant EGs of the present invention will have improved activity as compared to a reference sequence. For example improved enzyme activity at a pH range of 3.0 to 7.5, also at a pH range of 3.5 to 6.5, also at a pH range of 3.5 to 6.0, also at a pH range of 3.5 to 5.5, also at a pH range of 4.0 to 6.0, also at a pH range of 4.0 to 5.5 also at a pH range of 4.0 to 5.0. Some EG variants will have improved thermo-stability or improved thermo-activity at a temperature of about 55 to 85° C., also at a temperature of 60 to 80° C., also at a temperature of about 60 to 75° C., and also at a temperature of about 60 to 70° C. In some embodiments, the variant EGs will have improved enzyme activity at a pH of 4.0 to 5.0 and a temperature of 60-70° C., and have a catalytic domain with at least 88% sequence identity to the catalytic domain of S. avermitilis endoglucanase (SEQ ID NO:1).

In some embodiments, the variant EGs of the invention will exhibit endoglucanase activity that is at least 1.5 fold, at least about 2.0 fold, at least about 3.0 fold, at least about 4.0 fold, at least about 5.0 fold, at least about 6.0 fold, at least about 7.0 fold, at least about 8.0 fold and at least 10 fold greater than the endoglucanase activity of the EG of SEQ ID NO: 2 when tested under the same conditions. In other embodiments, the stability (half-life) of the variant EG at pH 5.0 and 65° C. will be at least 100 fold, at least 200 fold, at least 300 fold, at least 400 fold, at least 500 fold, at least 600 fold, at least 700 fold, at least 800 fold and even 1000 fold greater than the stability of a reference EG sequence (such as but not limited to SEQ ID NO: 2) under the same conditions.

The variant endoglucanases of the present invention may be prepared either by mutating the reference endoglucanase as described above, synthetically engineering a gene encoding the variant endoglucanase, or by synthetically generating a polypeptide having the amino acid residue substitutions as described herein.

Modified Variants

The present invention includes conservatively modified variants of the SavO EG polypeptides described herein (e.g., Table 4A-C). In some embodiments these variants have conservative substitutions made in their amino acid sequences. Examples of conservative substitutions are within the group of basic amino acids (arginine, lysine and histidine), acidic amino acids (glutamic acid and aspartic acid), polar amino acids (glutamine and asparagines), hydrophobic amino acids (leucine, isoleucine and valine), aromatic amino acids (phenylalanine, tryptophan and tyrosine), and small amino acids (glycine, alanine, serine, threonine, proline, cysteine and methionine). Amino acid substitutions which do not generally alter the specific activity are known in the art and are described, for example, by H. Neurath and R.L. Hill, 1979, in "The Proteins," Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

Conservatively substituted variations of the SavO EG polypeptides of the present invention include substitutions relative to the variants listed herein (e.g., Table 4A-C) of a small percentage, typically less than 5%, more typically less than 2%, and often less than 1% of the amino acids of the polypeptide sequence, with a conservatively selected amino acid of the same conservative substitution group. The addition of sequences which do not alter the encoded activity of a SavO EG polynucleotide, such as the addition of a non-functional or non-coding sequence, is considered a conservative variation of the SavO EG polynucleotide.

The reference endoglucanase polynucleotide sequence cloned into a vector as described above, which encodes the naturally occurring S. avermitilis catalytic domain, can be subjected to site-specific mutagenic processes to generate the variant endoglucanases of the present invention. Site-directed mutagenesis techniques are described in Ling et al., *Anal Biochem.*, 254(2):157-178 (1997); Dale et al., *Ann. Rev. Genet.*, 19:423-462 (1996); Botstein & Shortle, *Science*, 229: 1193-1201 (1985); Carter, *Biochem. J.*, 237:1-7 (1986); and Kunkel, "The efficiency of oligonucleotide directed mutagenesis" in Nucleic Acids & Molecular Biology (Eckstein, F. and Lilley, D. M. J. eds., Springer Verlag, Berlin (1987)); Kunkel, *Proc. Natl. Acad. Sci. USA*, 82:488-492 (1985); Kunkel et al., *Methods in Enzymol.*, 154:367-382 (1987); Zoller & Smith, *Nucleic Acids Res.*, 10:6487-6500 (1982); Zoller & Smith, *Methods in Enzymol.*, 100:468-500 (1983); Zoller & Smith, *Methods in Enzymol.*, 154:329-350 (1987); Taylor et al. (1985) *Nucl. Acids Res.*, 13: 8765-8787 (1985); Nakamaye & Eckstein, *Nucl. Acids Res.*, 14:9679-9698 (1986); Sayers et al., *Nucl. Acids Res.*, 16:791-802 (1988); Kramer & Fritz, *Methods in Enzymol.*, 154:350-367 (1987); Kramer et al., *Nucl. Acids Res.*, 16:7207 (1988); and Fritz et al., 1988, *Nucl. Acids Res.*, 16:6987-99.

A variant EG polypeptide of the invention can be subject to further modification to generate new polypeptides that retain the specific substitutions that characterizes the variant and which may have desirable properties. For example, a polynucleotide encoding a variant endoglucanase with an improved property can be subjected to additional rounds of mutagenesis treatments to generate polypeptides with further improvements in the desired enzyme property.

The number of modifications to the reference polypeptide, e.g. SEQ ID NO:1, that produces an improved endoglucanase property may comprise one or more amino acids. Protein evolution of combinatorial mutations can be accomplished by any method known in the art including, but not limited to, classical and/or synthetic DNA shuffling techniques.

Classical DNA shuffling generates variant DNA molecules by in vitro homologous recombination from random fragmentation of a parental DNA followed by reassembly using ligation and/or PCR, which results in randomly introduced point mutations. It consists of a three-step process that begins with the enzymatic digestion of genes, yielding smaller fragments of DNA. The small fragments are then allowed to randomly hybridize and are filled in to create longer fragments. Ultimately, any full-length, recombined genes that are re-created are amplified via PCR. If a series of alleles or mutated genes is used as a starting point for DNA shuffling, the result is a library of recombined genes that can be translated into novel proteins. The library can in turn be screened for increased activity at the desired conditions as described above. Endoglucanases that were generated with single amino acid mutations via either random or site-directed mutagenesis as described herein provide a parental or reference nucleotide sequence. Genes with beneficial mutations can be shuffled further, both to bring together these independent, beneficial mutations in a single nucleotide sequence and to eliminate any mutations that would prevent the desired endoglucanase for exhibiting activity that the pH and temperatures desired for the present invention.

Synthetic DNA shuffling may also be used to increase endoglucanase activity. In synthetic recombination methods, a plurality of oligonucleotides are synthesized which collectively encode a plurality of the mutations to be recombined. The oligonucleotides are designed based on the determination of favorable amino acid substitutions as described above. Following manufacture of the oligonucleotides, the methods of shuffling as described above can be used to create a library of variant endoglucanases.

Recombination-based directed evolution may further be complemented by protein sequence activity relationships (ProSAR), which incorporates statistical analyses in targeting amino acid residues for mutational analysis. See, e.g., Fox et al., *Nature Biotechnology* 25: 338-344 (2007). Using directed evolution in combination with statistical analysis facilitates mutation-oriented enzyme optimization by identifying beneficial mutations even in endoglucanase variants with reduced function. Using this approach, potentially beneficial residues in the catalytic domain of S. avermitilis endoglucanase can be predicted based on the three dimensional structure of the catalytic domain of the Streptomyces lividans CelB2 endoglucanase (Sulzenbacher et al., 1999, Biochemistry 38:4826-33).

Methods of protein evolution are well known in the art. See, e.g., Wells et al., Gene 34:315-323 (1985); Minshull et al., *Curr Opin Chem Biol* 3:284-290 (1999); Christians et al, *Nature Biotech* 17:259-264 (1999); Crameri et al., *Nature* 391:288-291 (1998); Crameri et al., *Nature Biotech* 15:436-438 (1997); Zhang et al., *Proc Natl Acad Sci USA* 94:45-4-4509 (1997); Crameri et al., Nature Biotech 14:315-319 (1996); Stemmer, *Nature* 370:389-391 (1994); Stemmer, *Proc Natl Acad Sci USA* 91:10747-10751 (1994); WO 95/22625; WO 97/0078; WO 97/35966; WO 98/27230; WO 00/42651; WO 01/75767 and U.S. Pat. Nos. 5,605,793, 5,811,238, 5,830,721, 5,834,252, 5,837,458 and 6,537,746.

Variant endoglucanases having the amino acid substitutions described herein can also be synthetically generated. Chemically synthesized polypeptides may be generated using the well-known techniques of solid phase, liquid phase, or peptide condensation techniques, and can include any combination of amino acids as desired to produce the variants described herein. Synthetic amino acids can be obtained from Sigma, Cambridge Research Biochemical, or any other chemical company familiar to those skilled in the art.

Signal Peptides

Typically the endoglucanases of the invention are expressed as secreted proteins. Thus, in some embodiments, the endoglucanase polypeptide will be expressed as a pre-protein including a signal peptide at the amino-terminus. In general, three distinct physicochemical regions are found within signal peptides: a positively charged N-terminus, a central hydrophobic region, and a more polar flexible C-terminus ending in a signal cleavage site.

A signal peptide sequence may be heterologous to (foreign to) a secreted polypeptide or may be naturally associated with the secreted polypeptide or with a parent polypeptide sequence of which the secreted polypeptide is a variant. In some cases a signal peptide is linked to a polypeptide sequence encoding a naturally occurring polypeptide that is not normally secreted or does not naturally contain a signal peptide coding region. In some cases a foreign signal peptide can replace a natural signal peptide coding region in order to enhance secretion of the polypeptide. In some cases a signal peptide is linked to a polypeptide sequence encoding a naturally polypeptide that is not found in nature, such as a truncated form of a naturally occurring protein. Any signal peptide coding region which directs the expressed polypeptide into the secretory pathway of a host cell of choice may be used in the present invention. Generally the signal peptide will be selected for optimal expression and secretion in a particular host. Exemplary signal peptides include bacterial signal peptide sequences, fungal signal peptide sequences, artificial signal peptide sequences, and signal peptide sequences from plants and animals.

Methods are well know for fusing a nucleic acid segment encoding a desired signal peptide with a nucleic acid sequence encoding a polypeptide. Commercial expression vectors are available in which a polypeptide-encoding nucleic acid sequence can be inserted in-frame with a nucleic acid sequence encoding a signal peptide, and containing regulatory elements required for optimal expression of the encoded fusion protein.

Bacterial Signal Peptides

In one embodiment, the EG polypeptide of the invention will be operably linked to a signal peptide sequence derived from a bacterial sp. such as a signal sequence derived from a *Bacillus* (e.g., *B. stearothermophilus*, *B. licheniformis*, *B. subtilis* or *B. megaterium*). Additionally effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis subtilisin*, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiol Rev.* 57:109-37.

In one embodiment a *B. megaterium* signal peptide is operably linked to a heterologous protein for effective production and secretion of the heterologous protein in a bacterial host. In one embodiment the signal peptide comprises MKRIVMVGFILLFPLNMLAGPISSIAEAQ (SEQ ID NO: 9) or a sequence differing from SEQ ID NO:9 at, in separate embodiments, 1, 2, or 3 positions (e.g., 1, 2, or 3 positions in residues 2-25 of SEQ ID NO:9). Based, in part, on analysis of the *B. megaterium* genome, a library of nucleic acids encoding a set of approximately 200 putative signal peptides from *B. megaterium* was prepared and screened using an approach similar to that of Brockmeier et al., 2006, *J Mol Bio* 362:393-402. The coding regions of these putative signal peptides were cloned upstream of open reading frames of genes encoding SavO variant 5 (SEQ ID NO: 8), a bacterial beta-glucosidase (CeIA), and a bacterial exoglucanase (CBH2). The constructs were heterologously expressed in *B. megaterium* and cellulase activity from the cell medium and cell lysate were measured to determine the efficiency of protein secretion.

When the SavO endoglucanse was expressed using the signal peptide sequence of SEQ ID NO: 9, a remarkably high proportion (~97%) of the EG protein produced was secreted. SEQ ID NO:9 was also effective in driving secretion of other heterologous proteins in *B. megaterium* (see Table 3) suggesting it is useful for secretion of a variety of proteins in bacteria, especially *Bacillus* species (for example and without limitation, *B. megaterium*, *B. stearothermophilus*, *B. licheniformis*, *B. subtilis*).

TABLE 3

| Protein | % secreted |
|---|---|
| SavO variant 5 | 97 |
| Beta-glucosidase (from cellulosic bacterium) | 80 |
| Exoglucanase (from cellulosic bacterium) | 91 |

Accordingly, in one aspect the invention provides a fusion protein comprising a first amino acid sequence encoding a signal peptide and second amino acid sequence encoding a heterologous polypeptide, where the first sequence is at the amino terminus of the fusion protein and is identical to or substantially identical to MKRIVMVGFILLFPLNMLAGPISSIAEAQ (SEQ ID NO: 9) and the second sequence does not encode a *B. megaterium* polypeptide. As illustrated in Example 12, below, it is sometimes convenient to introduce additional polypeptide sequence between the signal peptide and the heterologous protein. Typically the additional sequences are short (sometimes fewer than 20 amino acids, often fewer than 5 amino acids) and can be referred to as a "spacer peptide." However, longer sequences are also contemplated.

In some embodiments the heterologous polypeptide is a cellulase protein (i.e., an endoglucanse, a cellobiohydrolase or a beta-glucosidase). Exemplary cellulases include, without limitation, fungal cellulases and variants thereof and bacterial (e.g., *Streptomyces*) cellulases and variants thereof. In certain embodiments the cellulase is an endoglucanase such as a *Streptomyces avermitilis* endoglucanse or variant thereof. Exemplary heterologous polypeptides include improved endoglucanases having a sequence such as SEQ ID NO: 6, SEQ ID NO: 7, or SEQ ID NO: 8. The heterologous endoglucanse polypeptide may or may not include a cellulose binding domain.

In some embodiments the heterologous polypeptide is a not a cellulase protein. Suitable polypeptides include any non-*B. megaterium* polypeptide for which secretion is desired, such as fungal proteins, bacterial proteins, amylases, proteases, lipases, cutinases, xylanases, phytases, oxido-reductases, esterases, laccases, isomerases, transferases, transaminases, ketoreductases, glucose oxidases, dehydrogenases, artificial sequences, animal or plant proteins, and variants thereof.

In a related aspect, the invention provides a recombinant nucleic acid that encodes a fusion protein of the invention. In some embodiments the recombinant nucleic acid includes a promoter operably linked to the protein encoding sequence, for example, in a recombinant expression vector containing the nucleic acid and capable of expressing the fusion protein in a suitable host cell.

Also provided are host cells that contain the nucleic acid. Typically the host is a bacteria, for example a *Bacillus* species. In some important embodiments the host is *B. megaterium*.

It will be understood that host cells can be used to produce the heterologous polypeptide. For example, the invention provides a method for producing a heterologous polypeptide in a *B. megaterium* host cell. Advantageously, in *B. megate-*

*rium* (for example), the signal peptide can increase production of secreted protein by 50% or more compared to other signal peptides.

It will also be appreciated that fusion proteins and host cells that secret a cellulase find use in production of soluble sugars from a cellulosic feedstocks. For example, a cell expressing the cellulase (e.g., a SavO endoglucanse described herein) may be maintained under conditions in which the cellulase polypeptide is secreted into a culture medium, and a pretreated cellulosic feedstock can be combined with the culture medium (with cells or a substantially cell-free broth) or with secreted cellulase obtained from the culture medium. In some embodiments a *B. megaterium* host cell expressing a *Streptomyces avermitilis* endoglucanse or variant thereof is used in this fashion for conversion of cellulosic material.

Fungal Signal Peptides

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, Yeast 8:423-88.

Propeptides

In some embodiments, a cloned endoglucanase sequence may have a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *B. megaterium*, *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Polynucleotides Encoding Variant Endoglucanases

In another aspect, the present disclosure provides polynucleotides encoding the variant endoglucanase polypeptides encompassed by the invention. The polynucleotides may be operatively linked to one or more heterologous regulatory or control sequences that control gene expression to create a recombinant polynucleotide capable of expressing the polypeptide. Expression constructs containing a heterologous polynucleotide encoding the engineered endoglucanase can be introduced into appropriate host cells to express the corresponding endoglucanase.

Reference, Precursor and Parent Endoglucanases

A reference endoglucanase or a variant endoglucanase may be made by cloning into a construct any nucleic acid molecule of cDNA, genomic DNA, synthetic DNA or RNA that codes for the endoglucanase. The choice of vector depends on the host cell chosen to express the endoglucanase.

A reference endoglucanase nucleic acid may be obtained by amplifying any publicly available S. avermitilis template, and can be made by any of a number of methods known to those skilled in the art including PCR. However the invention is intended to encompass any suitable methods of DNA amplification. A number of DNA amplification techniques are suitable for use with the present invention. Such amplification techniques include methods such as polymerase chain reaction (PCR), strand displacement amplification (SDA), nucleic acid sequence based amplification (NASBA), rolling circle amplification, T7 polymerase mediated amplification, T3 polymerase mediated amplification and SP6 polymerase mediated amplification. The precise method of DNA amplification is not intended to be limiting, and other methods not listed here will be apparent to those skilled in the art and their use is within the scope of the invention. Exemplary references include manuals such as PCR Technology: *Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); *Current Protocols in Molecular Biology*, Ausubel, 1990-2008, including supplemental updates; U.S. Pat. No. 4,683,202.

Because of the knowledge of the codons corresponding to the various amino acids, availability of a polypeptide sequence provides a description of all the polynucleotides capable of encoding the subject polypeptide. The degeneracy of the genetic code, where the same amino acids are encoded by alternative or synonymous codons allows an extremely large number of nucleic acids to be made, all of which encode the improved endoglucanase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein.

An isolated polynucleotide encoding an improved endoglucanase may be manipulated in a variety of ways to provide for expression of the polypeptide. Manipulation of the isolated polynucleotide prior to its insertion into a vector, such as an expression vector, may be desirable or necessary depending on the expression vector. Polynucleotides encoding variant endoglucanases may contain promoters, signal sequences, terminators, etc., as described below. Recombinant DNA techniques, vectors, promoters, terminators, and the like are well known in the art and are described below.

Vectors

The nucleic acid encoding the endoglucanase is cloned into a vector, having one or more expression regulating regions such as a promoter and a terminator, a replication origin, etc., depending on the type of hosts into which they are to be introduced. A recombinant vector comprising a endoglucanase sequence may be any vector that can conveniently be subjected to recombinant DNA procedures, and the choice of vector will often depend on the host cell into which is to be introduced. The vector is preferably an expression vector in which the DNA sequence encoding the enzyme of the invention is operably linked to additional segments required for transcription of the DNA. In general, the expression vector is derived from plasmid or viral DNA, or may contain elements of both.

"Operably linked" indicates that the segments are arranged so that they function in concert for their intended purposes, e.g. a promoter that is operably linked to a gene sequence regulates or enhances transcription of the DNA sequence coding for the protein. The expression vectors of the present invention may contain an element(s) that permits integration of the vector into the host cell's genome or autonomous replication of the vector in the cell independent of the genome.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. The vectors may be linear or closed circular plasmids. Examples of bacterial origins of replication are P15A on or the origins of replication of plasmids pBR322, pUC19, pACYC177, or pACYC184 permitting replication in *E. coli*, and pUB110, pE194, pTA1060, or pAM.beta.1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell. See, e.g., Ehrlich, 1978, *Proc Natl Acad. Sci. USA* 75:1433.

For integration into the host cell genome, the vector may rely on the nucleic acid sequence encoding the polypeptide or any other element of the vector for integration of the vector into the genome by homologous or nonhomologous recombination. The expression vector containing the endoglucanase sequence may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Promoters

Regulatory sequences, which allow the regulation of the expression of the polypeptide relative to the growth of the host cell, may be provided. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

The promoter sequence is a nucleic acid sequence that is recognized by a host cell for expression of a polynucleotide, such as a polynucleotide containing the coding region. Generally, the promoter sequence contains transcriptional control sequences, which mediate expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

An appropriate promoter sequence, which can be obtained from genes encoding extracellular or intracellular polypeptides either homologous or heterologous to the host cell, may comprise the cloned vector. For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus megaterium* promoters, and prokaryotic beta-lactamase gene (VIIIa-Kamaroff et al., *Proc. Natl. Acad. Sci. USA* 75: 3727-3731 (1978)), as well as the tac promoter (DeBoer et al., *Proc. Natl. Acad. Sci. USA* 80: 21-25 (1993)). Further promoters include trp promoter, phage lambda $P_L$, T7 promoter and the like. Promoters suitable for use in the invention are described in "Useful proteins from recombinant bacteria" in *Scientific American* 242:74-94 (1980); and in Sambrook et al. (2001), supra.

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-88.

Transcription Terminators

Cloned endoglucanases may also have a suitable transcription terminator sequence, a sequence recognized by a host cell to terminate transcription. The terminator sequence is operably linked to the 3' terminus of the nucleic acid sequence encoding the polypeptide. Any terminator that is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase,

*Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C(CYCI), and *Saccharomyces cerevisiae* glyceraldehyde-3-phosphate dehydrogenase. Other useful terminators for yeast host cells are described by Romanos et al., 1992, *Yeast* 8:423-88.

Leader Sequence

A suitable leader sequence may be part of a cloned endoglucanase sequence, which is a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

Polyadenylation Sequences

Sequences may also contain a polyadenylation sequence, which is a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, *Mol Cell Bio* 15:5983-5990 (1995).

Selectable Markers

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

Exemplary Expression Vectors

Expression vectors useful in the present invention are commercially available. Suitable commercial expression vectors include p3xFLAGTM™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(−)® and pBK-CMV, which are commercially available from Stratagene, La Jolla Calif., and plasmids which are derived from pBR322 (Gibco BRL), pUC (Gibco BRL), pREP4, pCEP4 (Invitrogen) or pPoly (Lathe et al., *Gene* 5.7:193-201 (1987)). A preferred vector is a modified vector derived from the commercially available *Bacillus megaterium* shuttle vector pMM1525 (Boca Scientific Inc. Boca Raton, Fla.) as further described in the examples.

Host Cells

The sequence encoding an endoglucanase is transformed into a host cell in order to allow propagation of the endoglucanase vector and expression of the endoglucanase. As noted above, the endoglucanase is post-translationally modified to remove the signal peptide and in some cases may be cleaved after secretion.

The transformed or transfected host cell described above is cultured in a suitable nutrient medium under conditions permitting the expression of the endoglucanase. The medium used to culture the cells may be any conventional medium suitable for growing the host cells, such as minimal or complex media containing appropriate supplements. Cells are optionally grown in HTP media. Suitable media are available from commercial suppliers or may be prepared according to published recipes (e.g. in catalogues of the American Type Culture Collection).

In some embodiments, the host cell is a eukaryotic cell. Suitable eukaryotic host cells include, but are not limited to, fungal cells, algal cells, insect cells, and plant cells. Suitable fungal host cells include, but are not limited to, Ascomycota, Basidiomycota, Deuteromycota, Zygomycota, Fungi imperfecti. Particularly preferred fungal host cells are yeast cells and filamentous fungal cells. The filamentous fungi host cells of the present invention include all filamentous forms of the subdivision Eumycotina and Oomycota. (Hawksworth et al., In Ainsworth and Bisby's Dictionary of The Fungi, 8$^{th}$ edition, 1995, CAB International, University Press, Cambridge, UK). Filamentous fungi are characterized by a vegetative mycelium with a cell wall composed of chitin, cellulose and other complex polysaccharides. The filamentous fungi host cells of the present invention are morphologically distinct from yeast.

In the present invention a filamentous fungal host cell may be a cell of a species of, but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, or teleomorphs, or anamorphs, and synonyms or taxonomic equivalents thereof.

In some embodiments of the invention, the filamentous fungal host cell is of the *Trichoderma* species, e.g., *T. longibrachiatum, T. viride* (e.g., ATCC 32098 and 32086), *Hypocrea jecorina* or *T. reesei* (NRRL 15709, ATTC 13631, 56764, 56765, 56466, 56767 and RL-P37 and derivatives thereof—See Sheir-Neiss et al., Appl. Microbiol. Biotechnology, 20 (1984) pp 46-53), *T. koningii*, and *T. harzianum*. In addition, the term "*Trichoderma*" refers to any fungal strain that was previously classified as *Trichoderma* or currently classified as *Trichoderma*. In some embodiments of the invention, the filamentous fungal host cell is of the *Aspergillus* species, e.g., *A. awamori, A. funigatus, A. japonicus, A. nidulans, A. niger, A. aculeatus, A. foetidus, A. oryzae, A. sojae*, and *A. kawachi*. (Reference is made to Kelly and Hynes (1985) *EMBO J.* 4,475479; NRRL 3112, ATCC 11490, 22342, 44733, and 14331; Yelton M., et al., (1984) *Proc. Natl. Acad. Sci. USA*, 81, 1470-1474; Tilburn et al., (1982) *Gene* 26, 205-221; and Johnston, I. L. et al. (1985) EMBO J. 4, 1307-1311). In some embodiments of the invention, the filamentous fungal host cell is of the *Chrysosporium* species, e.g., *C. lucknowense, C. keratinophilum, C. tropicum, C. merdarium, C. inops, C. pannicola*, and *C. zonatum*. In some embodiments of the invention, the filamentous fungal host cell is of the *Myceliophthora* species, e.g., *M. thermophilia*. In some embodiments of the invention, the filamentous fungal host cell is of the *Fusarium* species, e.g., *F. bactridioides, F. cerealis, F. crookwellense, F. culmorum, F. graminearum, F. graminum. F. oxysporum, F. roseum*, and *F. venenatum*. In some embodiments of the invention, the filamentous fungal host cell is of the *Neurospora* species, e.g., *N. crassa*. Reference is made to Case, M. E. et al., (1979*Proc. Natl. Acad. Sci. USA*, 76, 5259-5263; U.S. Pat. No. 4,486,553; and Kinsey, J. A. and J. A. Rambosek (1984) *Molecular and Cellular Biology* 4, 117-122. In some embodiments of the invention, the filamentous fungal host cell is of the *Humicola* species, e.g., *H. insolens, H. grisea*, and *H. lanuginosa*. In some embodiments of the invention, the filamentous fungal host cell is of the *Mucor* species, e.g., *M. miehei* and *M. circinelloides*. In some embodiments of the invention, the filamentous fungal host cell is of the *Rhizopus* species, e.g., *R. oryzae* and *R. niveus*. In some embodiments of the invention, the filamentous fungal host cell is of the *Penicillum* species, e.g., *P. purpurogenum, P. chrysogenum*, and *P. verruculosum*. In some embodiments of the invention, the filamentous fungal host cell is of the *Thielavia* species, e.g., *T. terrestris*. In some embodiments of the invention, the filamentous fungal host cell is of the *Tolypocladium* species, e.g., *T. inflatum* and *T. geodes*. In some embodiments of the invention, the filamentous fungal host cell is of the *Trametes* species, e.g., *T. villosa* and *T. versicolor*.

In the present invention a yeast host cell may be a cell of a species of, but not limited to *Candida, Hansenula, Saccharomyces, Schizosaccharomyces, Pichia, Kluyveromyces*, and *Yarrowia*. In some embodiments of the invention, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, and *Yarrowia lipolytica*.

In some embodiments the filamentous fungal host cell is "*Chrysosporium lucknowense* C1," such as for example a strain described in U.S. Pat. Nos. 6,015,707, 5,811,381 and 6,573,086; US Pat. Pub. Nos. 2007/0238155, US 2008/0194005, US 2009/0099079; International Pat. Pub. Nos., WO 2008/073914 and WO 98/15633, and any derivatives thereof, and including, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184. Other strains include cells deposited under accession numbers ATCC 44006, CBS (Centraalbureau voor Schimmelcultures) 122188, CBS 251.72, CBS143.77, CBS 272.77, and VKM F-3500D. Exemplary derivatives include modified organisms in which one or more endogenous genes or sequences has been deleted and/or one or more heterologous genes or sequences has been introduced. Derivatives include UV18#100f [Δalpl, UV18#100f [Δ]pyr5 [Δ]alpl, UV18#100.f Aalpl Apep4 Aalp2, UV18#100.f [Δ]pyr5 Aalpl Apep4 Aalp2 and UV18#100.f [Δ]pyr4 [Δ]pyr5 Aalp 1 Apep4 Aalp2. as described in WO2008073914, incorporated herein by reference.

In some embodiments on the invention, the host cell is an algal cell such as, *Chlamydomonas* (e.g., *C. Reinhardtii*) and *Phormidium* (P. sp. ATCC29409).

In other embodiments, the host cell is a prokaryotic cell. Suitable prokaryotic cells include gram positive, gram negative and gram-variable bacterial cells. For example and not for limitation, the host cell may be a species of *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Franciselia, Havobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia* and *Zymomonas*. In some embodiments, the host cell is a species of, *Agrobacterium, Acinetobacter, Azobacter, Bacillus, Bifidobacterium, Buchnera, Geobacillus, Campylobacter, Clostridium, Corynebacterium, Escherichia, Enterococcus, Erwinia, Flavobacterium, Lactobacillus, Lactococcus, Pantoea, Pseudomonas, Staphylococcus, Salmonella, Streptococcus, Streptomyces*, and *Zymomonas*.

In yet other embodiments, the bacterial host strain is nonpathogenic to humans. In some embodiments the bacterial host strain is an industrial strain. Numerous bacterial industrial strains are known and suitable in the present invention.

In some embodiments of the invention, the bacterial host cell is of the *Agrobacterium* species, e.g., *A. radiobacter, A. rhizogenes*, and *A. rubi*. In some embodiments of the invention the bacterial host cell is of the *Arthrobacter* species, e.g., *A. aurescens, A. citreus, A. globformis, A. hydrocarboglutamicus, A. mysorens, A. nicotianae, A. paraffineus, A. protophonniae, A. roseoparqffinus, A. sulfureus*, and *A. ureafaciens*. In some embodiments of the invention the bacterial host cell is of the *Bacillus* species, e.g., *B. thuringiensis, B. anthracis, B. megaterium, B. subtilis, B. lentus, B. circulans, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. licheniformis, B. megaterium, B. clausii, B. stearothermophilus* and *B. amyloliquefaciens*. Some preferred embodiments of a *Bacillus* host cell include *B. subtilis, B. licheniformis, B. megaterium, B. stearothermophilus* and *B. amyloliquefa-*

*ciens*. In some embodiments the bacterial host cell is of the *Clostridium* species, e.g., *C. acetobutylicum, C. tetani* E88, *C. lituseburense, C. saccharobutylicum, C. perfringens*, and *C. beijerinckii*. In some embodiments the bacterial host cell is of the *Corynebacterium* species e.g., *C. glutamicum* and *C. acetoacidophilum*. In some embodiments the bacterial host cell is of the *Escherichia* species, e.g., *E. coli*. In some embodiments the bacterial host cell is of the *Erwinia* species, e.g., *E. uredovora, E. carotovora, E. ananas, E. herbicola, E. punctata*, and *E. terreus*. In some embodiments the bacterial host cell is of the *Pantoea* species, e.g., *P. citrea*, and *P. agglomerans*. In some embodiments the bacterial host cell is of the *Pseudomonas* species, e.g., *P. putida, P. aeruginosa, P. mevalonii*, and *P.* sp. D-0I 10. In some embodiments the bacterial host cell is of the *Streptococcus* species, e.g., *S. equisimiles, S. pyogenes*, and *S. uberis*. In some embodiments the bacterial host cell is of the *Streptomyces* species, e.g., *S. ambofaciens, S. achromogenes, S. avermitilis, S. coelicolor, S. aureofaciens, S. aureus, S. fungicidicus, S. griseus*, and *S. lividans*. In some embodiments the bacterial host cell is of the *Zymomonas* species, e.g., *Z. mobilis*, and *Z. lipolytica*.

Strains which may be used in the practice of the invention including both prokaryotic and eukaryotic strains, are readily accessible to the public from a number of culture collections such as American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Introduction of a vector or DNA construct into a host cell can be effected by calcium phosphate transfection, DEAE-Dextran mediated transfection, electroporation, or other common techniques (See Davis, L., Dibner, M. and Battey, I. (1986) *Basic Methods in Molecular Biology*, which is incorporated herein by reference). The engineered host cells can be cultured in conventional nutrient media modified as appropriate for activating promoters, selecting transformants, or amplifying the endoglucanase polynucleotide. Culture conditions, such as temperature, pH and the like, are those previously used with the host cell selected for expression, and will be apparent to those skilled in the art and in the references cited herein, including, for example, Sambrook, Ausubel and Berger, as well as, for example, Freshney (1994) *Culture of Animal Cells, a Manual of Basic Technique*, third edition, Wiley-Liss, New York; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (Eds.) *The Handbook of Microbiological Media* (1993) CRC Press, Boca Raton, Fla., all of which are incorporated herein by reference.

Purification of Expressed Endoqlucanases

The present invention is directed to a method of making a polypeptide having endoglucanase activity, culturing a host cell transformed with a polynucleotide encoding the endoglucanase in a culture medium under conditions that cause said polynucleotide to be expressed and optionally recovering or isolating the expressed EG polypeptide. Typically, recovery or isolation of the EG polypeptide is from the host cell culture medium, the host cell or both, using protein recovery techniques that are well known in the art, including those described herein.

Prior art references are available for the culture and production of cells, including cells of bacterial, plant, animal (especially mammalian) and archebacterial origin. See e.g., Sambrook, Ausubel, and Berger (all supra), as well as Freshney (1994) Culture of Animal Cells, a Manual of Basic Technique, third edition, Wiley-Liss, New York and the references cited therein; Doyle and Griffiths (1997) Mammalian Cell Culture: Essential Techniques John Wiley and Sons, NY; Humason (1979) Animal Tissue Techniques, fourth edition W.H. Freeman and Company; and Ricciardelli, et al., (1989) In vitro Cell Dev. Biol. 25:1016-1024, all of which are incorporated herein by reference. For plant cell culture and regeneration, Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York); Jones, ed. (1984) Plant Gene Transfer and Expression Protocols, Humana Press, Totowa, N.J. and Plant Molecular Biology (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) The Handbook of Microbiological Media (1993) CRC Press, Boca Raton, Fla., which is incorporated herein by reference. Additional information for cell culture is found in available commercial literature such as the Life Science Research Cell Culture Catalogue (1998) from Sigma-Aldrich, Inc (St Louis, Mo.) ("Sigma-LSRCCC") and, for example, The Plant Culture Catalogue and supplement (1997) also from Sigma-Aldrich, Inc (St Louis, Mo.) ("Sigma-PCCS"), all of which are incorporated herein by reference.

In some embodiments, cells expressing the variant EG polypeptides of the invention are grown under batch or continuous fermentation conditions. Classical batch fermentation is a closed system, wherein the compositions of the medium is set at the beginning of the fermentation and is not subject to artificial alternations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady sate growth conditions. Methods for modulating nutrients and growth factors for continuous fermentation processes as well as techniques for maximizing the rate of product formation are well known in the art of industrial microbiology.

The resulting polypeptide may be recovered/isolated and optionally purified by any of a number of methods known in the art. For example, the polypeptide may be isolated from the nutrient medium by conventional procedures including, but not limited to, centrifugation, filtration, extraction, spray-drying, evaporation, chromatography (e.g., ion exchange, affinity, hydrophobic, chromatofocusing, and size exclusion), or precipitation. Protein refolding steps can be used, as desired, in completing the configuration of the mature protein. Finally, high performance liquid chromatography (HPLC) can be employed in the final purification steps. In addition to the references noted supra, a variety of purification methods are well known in the art, including, for example, those set forth in Sandana (1997) Bioseparation of Proteins, Academic Press, Inc.; Bollag et al. (1996) Protein Methods, 2nd Edition, Wiley-Liss, NY; Walker (1996) The Protein Protocols Handbook Humana Press, NJ; Harris and Angal (1990) Protein Purification Applications: A Practical Approach, IRL Press at Oxford, Oxford, England; Harris and Angal Protein Purification Methods: A Practical Approach, IRL Press at Oxford, Oxford, England; Scopes (1993) Protein Purification: Principles and Practice 3rd Edition, Springer Verlag, NY; Janson and Ryden (1998) Protein Purification: Principles, High Resolution Methods and Applications, Second Edition, Wiley-VCH, NY; and Walker (1998) Protein Protocols on CD-ROM, Humana Press, NJ, all of which are incorporated herein by reference. A procedure for recovering the EG polypeptides from a cell lysate is illustrated in Example 2.

Cell-free transcription/translation systems can also be employed to produce EG polypeptides using the polynucleotides of the present invention. Several such systems are commercially available. A general guide to in vitro transcription and translation protocols is found in Tymms (1995) In vitro Transcription and Translation Protocols: Methods in Molecular Biology, Volume 37, Garland Publishing, NY, which is incorporated herein by reference.

EG Compositions and methods of use

The production of variant endoglucanases described herein have multiple industrial applications; which include but are not limited to, sugar production (e.g. glucose syrups), biofuels production, textile treatment, pulp or paper treatment, and applications in detergents or animal feed. A host cell containing a variant endoglucanase of the present invention may be used without recovery and purification of the recombinant endoglucanase, e.g. for use in a large scale biofermentor. Or, the recombinant endoglucanase may be expressed and purified from the host cell.

The variant endoglucanases that have been described herein are particularly useful for breaking down cellulose to smaller oligosaccharides, disaccharides and monosaccharide. As discussed in detail above, the variant endoglucanses are useful in saccharification methods described in Section III. Alternatively, the variant endoglucanses may be used in combination with other cellulase enzymes including, for example, conventional enzymatic saccharification methods, to produce fermentable sugars.

In some embodiments the EG enzyme compositions may be reacted with a biomass substrate in the range of about 25° C. to 100° C., about 30° C. to 90° C., about 30° C. to 80° C., and about 30° C. to 70° C. Also the biomass may be reacted with the EG enzyme compositions at about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C. and at about 100° C. Generally the pH range will be from about pH 3.0 to 8.5, pH 3.5 to 8.5, pH 4.0 to 7.5, pH 4.0 to 7.0 and pH 4.0 to 6.5. The incubation time may vary for example from 1.0 to 240 hours, from 5.0 to 180 hrs and from 10.0 to 150 hrs. For example the incubation time will be at least 1 hr, at least 5 hrs, at least 10 hrs, at least 15 hrs, at least 25 hrs, at least 50 hr, at least 100 hrs, at least 180 and the like). Incubation of the cellulase under these conditions may result in the release of substantial amounts of soluble sugars from the substrate. For example at least 20%, at least 30%, at least 40%, at least 50%, at least 60%, at least 70%, at least 80%, at least 90% or more soluble or fermentable sugar may be available as compared to the release of sugar by a parent polypeptide.

The fermentable sugars can be fermented into alcohols (e.g., ethanol) to be used as biofuels. The variant endoglucanases of the present invention may be utilized in any method used to generate alcohols or other biofuels from cellulose, and are not limited necessarily to those described herein. Two methods commonly employed are the separate saccharification and fermentation (SHF) method (see, Wilke et al., Biotechnol. Bioengin. 6:155-75 (1976)) or the simultaneous saccharification and fermentation (SSF) method disclosed for example in U.S. Pat. Nos. 3,990,944 and 3,990,945.

The SHF method of saccharification comprises the steps of contacting a cellulase with a cellulose containing substrate to enzymatically break down cellulose into fermentable sugars (e.g., monosaccharides such as glucose), contacting the fermentable sugars with an alcohol-producing microorganism to produce alcohol (e.g., ethanol or butanol) and recovering the alcohol.

In addition to SHF methods, a SSF method may be used. In some cases, SSF methods result in a higher efficiency of alcohol production than is afforded by the SHF method (Drissen et al., Biocatalysis and Biotransformation 27:27-35 (2009). One disadvantage of SSF over SHF is that higher temperatures are required for SSF than for SHF. In one embodiment, the present invention claims EG polypeptides that have higher thermo-stability than a reference EG and one practicing the present invention could expect an increase in ethanol production if using the cellulases described here in combination with SSF.

For cellulosic substances to be used effectively as substrates for the saccharification reaction in the presence of a cellulase of the present invention, it is desirable to pretreat the substrate. Means of pretreating a cellulosic substrate are known in the art and the present invention is not limited by such methods.

Any alcohol producing microorganism such as those known in the art, e.g., *Saccharomyces cerevisiae*, can be employed with the present invention for the fermentation of fermentable sugars to alcohols and other end-products.

The fermentable or soluble sugars produced from the use of one or more EG variants encompassed by the invention may be used to produce other end-products besides alcohols, such as but not limited to other biofuels compounds, acetone, amino acids, organic acids, glycerol, ascorbic acid, 1,3-propanediol and other chemicals.

The variant endoglucanases of the present invention may also be used for textile processing or cleaning. Such processing includes, but is not limited to, stonewashing, depilling, defuzzing, color clarification, harshness reduction, modifying the texture, feel and/or appearance of cellulose-containing fabrics or other techniques used during manufacturing or cleaning/reconditioning of cellulose-containing fabrics. Additionally, treating within the context of this invention contemplates the removal of "immature" or "dead" cotton from cellulosic fabric or fibers. Immature cotton is significantly more amorphous than mature cotton and because of uneven dyeing, for example.

Detergents may be developed from the endoglucanases of the present invention. Detergent compositions useful in accordance with the present invention may include special formulations such as pre-wash, pre-soak and home-use color restoration compositions. Such treating compositions may be in the form of a concentrate which requires dilution or in the form of a dilute solution or form which can be applied directly to the cellulose-containing fabric. As a detergent, the endoglucanases of this invention are useful for soil removal, to improve the fabric-care properties, or household color clarification and restoring effects. General treatment techniques for cellulase treatment of textiles are described, e.g., in EP Publication No. 2200016.

The textile material that is treated with the enzyme preparations of the present invention may be manufactured of natural cellulose containing fibers or synthetic cellulose containing fibers or mixtures thereof. Examples of natural cellulosics are cotton, linen, hemp, jute and ramie. Examples of synthetic cellulosics are viscose, cellulose acetate, cellulose triacetate, rayon, cupro and lyocell. The above mentioned cellulosics can also be employed in various blends comprising synthetic fibers such as polyester, polyamide, or acrylic fibers. The textile material may be yarn or knitted or woven, or formed by any other means.

Endoglucanases as described herein are further useful in the pulp and paper industry. In the pulp and paper industry, neutral cellulases can be used, for example, in deinking of different recycled papers and paperboards having neutral or alkaline pH, in improving the fiber quality, or increasing the drainage in paper manufacture. Other examples include the removal of printing paste thickener and excess dye after textile printing, and as a treatment for animal feed to aid in the digestion of feed containing high levels of cellulose.

In some embodiments, the variant EG is combined with other cellulases to form a cellulase mixture. Those skilled in the art are aware of other cellulase that may be used in conjunction with the variant EGs of the invention. Commercial cellulases are known and available from Danisco Inc, Genencor division, Novozymes, and Iogen. Enzymes of a cellulase mixture work together resulting in decrystallization and hydrolysis of the cellulose from a biomass substrate to yield soluble sugars, such as but not limited to glucose (Brigham et al., (1995) in Handbook on Bioethanol (C. Wyman ed.) pp 119-141, Taylor and Francis, Washington D.C.).

The endoglucanases of the present invention may be used in combination with other optional ingredients such as a buffer, a surfactant, and/or a scouring agent. A buffer may be used with the cellulases of the present invention to maintain a pH of 4-5 within the solution in which the cellulase is employed. The exact concentration of buffer employed will depend on several factors which one skilled in the art can determine. Suitable buffers are well known in the art. A surfactant may further be used in combination with the cellulases of the present invention. Suitable surfactants include any surfactant compatible with the cellulase being utilized and the fabric including, for example, anionic, non-ionic and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, etc. Suitable counter ions for anionic surfactants include, but are not limited to, alkali metal ions such as sodium and potassium; alkaline earth metal ions such as calcium and magnesium; ammonium ion; and alkanolamines having 1 to 3 alkanol groups of carbon number 2 or 3. Ampholytic surfactants include, e.g., quaternary ammonium salt sulfonates, and betaine-type ampholytic surfactants. Nonionic surfactants generally comprise polyoxyalkylene ethers, as well as higher fatty acid alkanolamides or alkylene oxide adduct thereof, and fatty acid glycerine monoesters. Mixtures of surfactants can also be employed as is known in the art.

The present invention may be practiced at effective amounts, concentrations, and lengths of time. An effective amount of cellulase is a concentration of cellulase sufficient for its intended purpose. For example, an effective amount of cellulase within a solution may vary depending on whether the intended purpose is to use the enzyme composition comprising the EG in a saccharification process, or for example a textile application such as stone-washing denim jeans. The amount of endoglucanase employed is further dependent on the equipment employed, the process parameters employed, and the cellulase activity, e.g., a particular solution will require a lower concentration of endoglucanase where a more active cellulase composition is used as compared to a less active cellulase composition. A concentration of endoglucanase and length of time that an endoglucanase will be in contact with the desired target further depends on the particular use employed by one of skill in the art, as is described herein.

One skilled in the art may practice the present invention using endoglucanases in either aqueous solutions, or a solid endoglucanase concentrate. When aqueous solutions are employed, the endoglucanase solution can easily be diluted to allow accurate concentrations. A concentrate can be in any form recognized in the art including, but not limited to, liquids, emulsions, gel, pastes, granules, powders, an agglomerate, or a solid disk. Other materials can also be used with or placed in the cellulase composition of the present invention as desired, including stones, pumice, fillers, solvents, enzyme activators, and anti-redeposition agents depending on the intended use of the composition.

EXAMPLES

The following examples are offered to illustrate, but not to limit the claimed invention.

Example 1

Wild Type *Streptomyces avermitilis* Endoglucanase (SavO EG) Gene Acquisition and Construction of Expression Vectors A gene coding for *Streptomyces avermitilis* endoglucanase (SavO EG) was codon optimized for expression in *B. megaterium* and *Escherichia coli* based on the reported amino acid sequence (Omura et al., 2001, Proc. Natl. Acad. Sci. U.S.A. 98:12215-20) and a codon optimization algorithm incorporated as described in Example 1 of WO2008042876 incorporated herein by reference. The gene was synthesized by GenScript Corporation (GenScript Corporation, 120 Centennial Ave., Piscataway, N.J. 08854, USA) and the DNA sequence verified. The gene was cloned behind a *Bacillus megaterium* "optimized" signal peptide plus a spacer region (12 bases encoding amino acid residues DTSM, SEQ ID 16) into an *E. coli/B. megaterium* shuttle vector pSSBm27 using the BsrGI/NgoMIV cloning sites. The vector pSSBm27 is a modified vector based on the shuttle vector pMM1525 (Boca Scientific Inc., Boca Raton, Fla.). The signal peptide and gene were under the control of an xlyose promoter (Pxyl) regulated by the xylose repressor gene (xylR) present on the shuttle vector. The vector contained the 'rep U' origin of replication for *Bacillus* and a tetracycline ampicillin resistance marker. The vector also contained the pBR322 origin of replication and an ampicillin resistance marker for maintenance in *E. coli*. The resulting plasmid (pSSBm27-SavO EG) was transformed by a standard PEG-mediated method of DNA transfer into *B. megaterium* protoplasts. The SavO EG sequence from the transformants was verified. The polynucleotide sequence of the catalytic domain, linker and cellulose binding domain that was cloned into the shuttle pSSBm27 vector is defined by SEQ ID NO: 5.

As discussed below, SavO native 4 and SavO variants (e.g., variants 1, 3, 5, 6 etc.) were expressed as fusion proteins including a *B. megaterium* signal peptide and the amino-terminal spacer sequence.

Example 2

Shake Flask Procedure

A single microbial colony of *Bacillus megaterium* containing a plasmid with the SavO EG gene was inoculated into 1 ml Luria-Bertani (LB) Broth (0.01 g/L Peptone from casein, 0.005 g/L yeast extract, 0.01 g/L sodium chloride) containing 10 µg/mL tetracycline. Cells were grown overnight (at least 16 hrs) in an incubator at 37° C. with shaking at 250 rpm. The culture was then diluted into 50 mL A5 media (2 g/L $(NH_4)_2SO_4$, 3.5 g/L $KH_2PO_4$, 7.3 g/L $Na_2HPO_4$, 1 g/L yeast extract, pH to 6.8), 50 µL of trace elements solution (49 g/L $MnCl_2 \cdot 4H_2O$, 45 g/L $CaCl_2$, 2.5 g/L $(NH_4)Mo_7 \cdot O_{24} \cdot H_2O$, 2.5 g/L $CoCl_2 \cdot 6H_2O$), 750 µL of 20% glucose, 75 µL of 1M $MgSO_4$, 50 µL of 10 mg/mL tetracycline, 50 µL of 2.5 g/L $FeSO_4 \cdot 7H_2O$ in a 250 ml flask to an optical density at 600 nm (OD600) of 0.2 and allowed to grow at 37° C. Expression of the SavO EG gene was induced with 0.5% xylose (final concentration) when the OD600 of the culture was 0.6 to 0.8 and incubated overnight (at least 16 hrs). Cells were pelleted by centrifugation (4000 rpm, 15 min, 4° C.). The clear media supernatant containing the secreted SavO EG enzyme was collected and stored at −20° C. SavO EG activity was confirmed using pNPC (p-nitrophenyl13-D-cellobioside) as substrate as described by Lemaire, et al. 1993, *J. Bact.*, 175(11): 3353-3360, which is incorporated herein by reference. The experimental procedures were also used for endoglucanase activity assays.

Example 3

Inoculation Shake Flask Procedure

A single microbial colony of *B. megaterium* containing a plasmid coding for SavO EG was inoculated into 250 ml A5 broth (2.0 g/L ammonium sulfate, 7.26 g/L of disodium monohydrogen phosphate, 3.52 g/L of potassium dihydrogen phosphate, 1.0 g/L of Tastone-154 yeast extract, 1.5 ml/L of 1M magnesium sulfate solution, 1.0 ml of 2.5 g/L iron sulfate septahydrate solution, and 1.0 ml/L of trace element solution containing 45.0 g/L of calcium chloride, 49.0 g/L manganese chloride tetrahydrate, 2.5 g/L cobalt chloride hexahydrate, and 2.5 g/L ammonium molybdate hydrate) containing 10 µg/ml tetracycline and 0.5% glucose. Cells were grown overnight (at least 12 hrs) in an incubator at 30° C. with shaking at 250 rpm. When the OD600 of the culture is 3.0 to 5.0 the cells were removed from the incubator and used immediately for inoculating fermentor, or stored at 4° C. until used.

Example 4

Reference Endoglucanase Expression; Fermentation Procedure

In an aerated agitated 15 L fermentor, 6.0 L of growth medium containing 0.88 g/L ammonium sulfate, 1.0 g/L of sodium citrate, 12.5 g/L of dipotassium monohydrogen phosphate trihydrate, 6.25 g/L of potassium dihydrogen phosphate, 3.3 g/L of Tastone-154 yeast extract, 2.0 g/L of Phytone peptone, and 1.0 ml/L of trace element solution containing 45.0 g/L of calcium chloride, 49.0 g/L of manganese chloride tetrahydrate, 2.5 g/L cobalt chloride hexahydrate, and 2.5 g/L ammonium molybdate hydrate was sterilized and brought to a temperature of 37° C. 120.0 mL of a feed solution containing 500 g/L glucose monohydrate, 12 g/L ammonium chloride and 5.0 g/L magnesium sulfate anhydrous was added. 0.083 g/L ferric ammonium citrate and 10 µg/mL tetracycline were added. The fermentor was inoculated with a late exponential culture of *B. megaterium*, containing a plasmid coding for SavO EG, grown in a shake flask as described in example 3 to a starting OD600 of 3.0 to 5.0. The fermentor was agitated at 500-1200 rpm and air was supplied to the fermentation vessel at 0.6-25.0 L/min to maintain dissolved oxygen level of 50% saturation. The pH of the culture was controlled at 7.0 by addition of 28% v/v ammonium hydroxide. Growth of the culture was maintained by the addition of a feed solution containing 500 g/L glucose monohydrate, 12 g/L ammonium chloride and 5.0 g/L magnesium sulfate anhydrous. After the culture reached an OD600 of 70±10, the expression of SavO EG was induced by the addition of xylose to obtain and maintain a concentration of 0.5%. The culture was grown for another 12 hours. The culture was then chilled to 4° C. and maintained at 4° C. until harvested. Media supernatant was harvested by centrifugation at 5000G for 30 minutes in a Sorval RC12BP centrifuge at 4° C.

The clear supernatant was decanted and concentrated ten-fold using a polyethersulfone polymer ultrafiltration membrane with a molecular weight cut off of 10 kDa. The concentrate was diafiltered using at least 3 volumes of 100 mM sodium acetate buffer pH 5.0. The final concentrate was dispensed into shallow containers and stored at −80° C.

Example 5

Assays to Determine Endoglucanase Activity

Endoglucanase activity may be determined either by a para-nitrophenyl-6-D-cellobioside (pNPC) assay, or a cellulose assay.

A colorimetric pNPC (p-nitrophenyl-β-D-cellobiosidey-based assay was used for measuring EG activity. In a total volume of 150 µL, 50 µL clear media supernatant containing EG enzyme was added to 5 mM pNPC (from Sigma) solution in 25 mM sodium acetate buffer, pH 4-5. The reactions were incubated at pH 5, 50° C. or pH 4, 70° C. for 24 hrs. In a total volume of 150 µL, 20 µL (pH 5, 50° C.) or 75 µL (pH 4, 70° C.) of the reaction mixture was quenched with 1M sodium carbonate pH 11 solution. The absorbance of the solution was measured at 405 nm to determine the conversion of pNPC to p-nitrophenyl. The release of p-nitrophenol ($\epsilon = 17,700$ $M^{-1}$ $cm^{-1}$) was measured at 405 nm to calculate EG activity. Detectable EG activity (~20% as compared to under optimal conditions (pH 5, 50° C.)) was observed under high throughput screening conditions (pH 4, 70° C.).

EG activity was also determined using a cellulose assay, which used Avicel (microcrystalline cellulase, from Sigma) as substrate. In a total volume of 150 µL, 75 µL clear media supernatant containing EG enzyme was added to 200 g/L Avicel in 300 mM sodium acetate buffer (pH 4-5). The reaction was incubated at 50-70° C. for 24 hours. Biotransformations were quenched with 150 µL of 10 mM sulfuric acid. Conversion of Avicel to soluble sugar oligomers was measured using an Agilent HPLC 1200 equipped with HPX-87H Ion exclusion column (300 mm×7.8 mm) with water as eluent at a flow rate of 1.0 mL/min at 80° C. The retention times of the cellobiose and glucose were 4.7 and 5.8 minute respectively. Detectable SavO EG activity (~20% as compared to under optimal conditions (pH 5, 50° C.)) was observed under high throughput screening conditions (pH 4, 70° C.).

Example 6

Evaluation of Optimal SavO EG Activity

The activity profile of CDX-SavOcat (SEQ ID NO: 2) was investigated at different temperatures (50° C., 60° C. and 70°

C.) and pH (4.4-6.8) using Avicel (200 g/L) as a substrate. The experimental and analytical procedures are described in Example 5. CDX-SavOcat (SEQ ID NO: 2) exhibited optimum activity at pH 5 and 50° C., and detectable endoglucanse activity was observed at pH 4.4 and 70° C. as shown in FIG. 3.

Example 7

High Throughput Assays to Identify Improved SavO EG Variants

Plasmid libraries containing variant eg genes were transformed into B. megaterium and plated on Luria-Bertani (LB) agar plates containing 3 μg/mL tetracycline with a DM3 regeneration media overlay (400 mM sodium succinate dibasic, pH 7.3, 0.5% casamino acids, 0.5% yeast extract, 0.4% $K_2HPO_4$, 0.2% $KH_2PO_4$, 20 mM $MgCl_2$, 0.5% glucose and 0.2% BSA). After incubation for at least 18 hours at 30° C., colonies were picked using a Q-bot® robotic colony picker (Genetix USA, Inc., Beaverton, Oreg.) into shallow, 96-well well microtiter plates containing 180 μL LB and 10 μg/mL tetracycline. Cells were grown overnight at 37° C. with shaking at 200 rpm and 85% humidity. 20 μL of this culture was then transferred into 96-well microtiter plates (deep well) containing 380 μL A5-glucose medium and 10 μg/mL tetracycline as described in Example 2. After incubation of deep-well plates at 37° C. with shaking at 250 rpm for 2 hours (OD600 0.6-0.8), recombinant gene expression by the cell cultures was induced by isopropyl thiogalactoside (IPTG) to a final concentration of 1 mM. The plates were then incubated at 37° C. with shaking at 250 rpm and 85% humidity for overnight (~15-18 hours). The deep plates were centrifuged at 4000 rpm for 15 minutes and the clear media supernatant containing the secreted EG enzyme was used for the high throughput pNPC or Avicel assay.

The SavO EG libraries were screened in high throughput using a tiered process. SavO EG variants were screened by tier 1 colorimetric pNPC-based high throughput assay (Substrate: pNPC; pH: 4.0; temperature: 70° C.; time: 24 hrs). Active EG variants identified from the tier1 assay were subsequently subjected to the tier 2 HPLC assay (Substrate: Avicel; pH: 4.0-5.0; temperature: 60-70° C.; time: 24 hrs) for the identification of improved variants.

Tier 1 variant screening was a pNPC-based High Throughput Assay. In shallow, 96-well microtiter plates 50 μL of media supernatant was added to 100 μL of 5 mM pNPC in sodium acetate buffer pH 4.0. After sealing with aluminum/polypropylene laminate heat seal tape (Velocity 11 (Menlo Park, Calif.), Cat#06643-001), the plates were shaken at 70° C. for up to 24 hrs. The plates were centrifuged for 5 minutes at 4000 rpm. In shallow well clear microtiter plates, 75 μL of the reaction mixture was quenched with 75 μL of 1M sodium carbonate pH 11 solution per well. The solutions were gently mixed for 3 times and absorbance was measured at 405 nm for the identification of active SavO EG variants.

Tier 2 variant screen was a cellulose-based High Throughput Assay. In deep, 96-well microtiter plates 75 μL of media supernatant was added to 75 μL of 200 g/L Avicel (microcrystalline cellulose, from Sigma) in 300 mM sodium acetate buffer pH 4.0-5.0. After sealing with aluminum/polypropylene laminate heat seal tape (Velocity 11 (Menlo Park, Calif.), Cat#06643-001), the plates were shaken at 60-70° C. for up to 24 hrs. The reactions were quenched by adding 150 μL of 10 mM sulfuric acid into the deep well plates. The plates were centrifuged at 4000 rpm for 5 minutes. 150 μL of supernatant from reaction mixture was filtered with 0.45 μm low-binding hydrophilic PTFE filter plate (Millipore, Billerica, Mass.). The HPLC sample plates were sealed with heat seal tape to prevent evaporation. As in Example 5B, conversion of Avicel to soluble sugar oligomers was measured using an Agilent HPLC 1200 equipped with HPX-87H Ion exclusion column (300 mm×7.8 mm) with water as eluent at a flow rate of 1.0 mL/min at 80° C. As described in Example 5, the retention times of the cellobiose and glucose were 4.7 and 5.8 minutes, respectively.

Example 8

Improved Endoglucanase Activities of Engineered SavO EG Variants

Improved SavO EG variants were identified from the high throughput screening of various SavO EG variant libraries as described in Example 7. Tables 4A, 4B and 4C depict the improvement in activities of EG variants encompassed by the invention.

Table 4A shows improved SavO EG variants derived from the CDX-SavOcat (SEQ ID NO:2). These variants were directly compared to CDX-SavOcat (SEQ ID NO: 2) in screening. Both the CDX-SavOcat and SavO EG variants contain the N-terminal "DTSM" spacer (SEQ ID NO:16). In Table 4A, the SavO EG catalytic domain without an N-terminal spacer (corresponding to SEQ ID NO:1) was used as the reference sequence for the numbering of the changed amino acid residues. The asterisk corresponds to the variant used for comparison of the subsequent round of variants described in Table 4B.

TABLE 4A

| Amino Acid Changes | Fold improvement[1] over CDX-SavOcat (SEQ ID NO: 2) |
|---|---|
| A29P, N191P | + |
| A53P | + |
| A29P, T50P, A53P, N191P | + |
| S74P | + |
| *A29P, A53P, S74P, N191P | ++ |
| A29P, A53P, N191P | + |
| T50P, A53P, S74P, N191P | ++ |
| A29P | + |
| A29P, T50P, A53P, S74P, N191P | + |
| A29P, A53P | + |
| T50P, A53P, S74P | + |
| A53P, S74P | + |
| A29P, A53P, S74P | + |
| T50P, A53P | + |
| A53P, S74P, N191P | + |
| A53P, N191P | + |
| T50P, A53P, N191P | + |
| T142C | + |
| A29L | + |
| A141T, Q182I | + |
| T50L | + |
| T81Q | + |
| M98V | + |
| T219D | + |
| Q43K | + |
| T110K | + |
| T81K | + |
| Q182I | + |
| T142H | + |
| T110E | + |
| V198I | + |
| P204L | + |
| T219C | + |
| I121L | + |
| A102S | + |
| S136E | + |

TABLE 4A-continued

| Amino Acid Changes | Fold improvement[1] over CDX-SavOcat (SEQ ID NO: 2) |
|---|---|
| S74E, T142M | + |
| S95D | + |
| A29T | + |
| M98K | + |
| D1E | + |
| Q43R | + |
| T142H, Q206E | + |
| Q206S | + |
| Q147S | + |
| A29H | + |
| R118K | + |
| M98T, G187E | + |
| Q14K | + |
| T33L | + |
| T81N | + |
| L79I | + |
| A29T, A141D | + |
| N51H | + |
| S185H | + |
| S185R | + |
| A29T, T142F | + |
| G15N, Q206R | + |
| A29R | + |
| N51K, Q190H | + |
| Q14P | + |
| S37E | + |
| A77V | + |
| S74K | + |
| S185I | + |
| S185T | + |
| A141S | + |
| S80K | + |
| S136H | + |
| S74R | + |
| M98I | + |
| Q206E | + |
| V82I | + |
| T33A | + |
| Q206V | + |
| Q14L | + |
| M98T | + |
| T142W | + |
| S136R | + |
| T219Q | ++ |
| Q43M | + |
| T33H | + |
| Q43E | + |
| T219E | + |
| Q43V | + |
| S74H | + |
| S136K | + |
| Y91F | + |
| S185D | + |
| S95H | + |
| A165S | + |
| Q78K | + |
| N207G | + |
| S74L | + |
| Q43L | + |
| N191Q | + |
| S74V | + |
| S74Q | + |
| T222K | + |
| N191Y | + |
| T219A | + |
| T142V | + |
| T142S | + |
| S136D | + |
| T33I | + |
| S185E | + |
| T142N | + |
| S95T | + |
| S167I | + |
| Q182V | + |
| S74T | + |
| S10L | + |
| T142M | + |
| S171T | + |
| S10H | + |
| S10T | + |
| T33Q | + |
| Q14E | + |
| T33V | + |
| T33E | + |
| T33R | + |
| A53G | + |
| S10Y | + |
| S10W | + |
| T81R | + |
| T81S | + |
| A29K | + |
| S83I | + |
| S83E | + |
| S83R | + |
| S83V | + |
| S95K | + |
| S95N | + |
| S136T | + |
| S136V | + |
| S185L | + |
| S185N | + |
| S185Q | ++ |
| S185V | + |
| S185Y | + |
| M98Q | + |
| S74N | + |
| S74E | + |
| S74A | + |
| S167D | + |
| S152V | + |
| Q190D | + |
| S152M | + |
| V48K | + |
| N68V | + |
| S152I | + |
| V131M | + |
| S152L | + |
| N68L | + |
| V131E | + |
| V184F, S185I | + |
| N68K | + |
| T12V | + |
| N68I | + |
| T12I | + |
| D36Y | + |
| V131I | + |
| N68H | + |

[1]Fold improvement is represented as follows:
+ = 1.1 to 2.0 fold improvement over CDX-SavOcat (SEQ ID NO:2)
++ = 2.1 to 2.2 fold improvement over CDX-SavOcat (SEQ ID NO:2)

Table 4B shows improved SavO EG variants derived from the CDX-SavOcat (SEQ ID NO: 2). The variants were not directly compared to the CDX-SavOcat in screening, but were compared to the best variant from Table 4A (A29P, A53P, S74P, N191P) and this sequence was used as the control ("+control") to estimate fold improvement (FI) over the CDX-SavOcat activity. Both the CDX-SavOcat and variants contain the N-terminal "DTSM" spacer (SEQ ID NO:16). In Table 4B, the native SavO EG sequence (catalytic domain without N-terminal spacer, SEQ ID NO:1) was used as the reference sequence for the numbering of the changed amino acid residues. The double asterisk (**) corresponds to the variant used for comparison of the subsequent round of variants described in Table 4C.

TABLE 4B

| Amino Acid Changes | Fold improvement[1] over SEQ ID NO:6 (Control Variant from Table 4A) |
|---|---|
| A29P, A53P, S74P, N191P (SEQ ID NO: 6) | |
| A29P, Q43R, A53P, S74P, V82I, M98V, N191P | +++ |
| S10W, A29P, A53P, S74P, V82I, M98I, N191P | +++ |
| S10W, A29P, A53P, S74P, M98I, N191P | +++ |
| S10W, A29P, Q43R, A53P, S74P, V82I, N191P | +++ |
| D1E, S10W, A29P, Q43R, A53P, S74P, V82I, M98T, N191P | +++ |
| D1E, S10Y, A29P, A53P, S74P, V82I, N191P | ++ |
| D1E, S10W, A29P, A53P, S74P, M98I, N191P | +++ |
| S10W, A29P, A53P, S74P, V82I, N191P | ++ |
| **S10W, A29P, Q43R, A53P, S74P, V82I, M98V, N191P | +++ |
| S10W, A29P, A53P, S74P, M98V, N191P | +++ |
| S10Y, A29P, Q43R, A53P, S74P, M98V, N191P | +++ |
| A29P, Q43R, A53P, S74P, M98V, N191P | +++ |
| S10W, A29P, A53P, S74P, M98V, L188F, N191P, | +++ |
| A29P, A53P, S74P, M98V, R118Q, N191P, P204L, Q206V | ++ |
| D1E, A29P, Q43R, A53P, S74P, M98I, N191P | +++ |
| A29P, Q43R, A53P, S74P, N191P | ++ |
| A29P, A53P, S74P, V82I, N191P | ++ |
| D1E, S10W, A29P, Q43R, A53P, S74P, M98I, N191P | +++ |
| A29P, Q43R, A53P, S74P, M98V, N191P, P204L, Q206E | +++ |
| S10Y, A29P, Q43R, A53P, S74P, N191P | ++ |
| S10W, A29P, Q43R, A53P, S74P, V82I, M98T, N191P | +++ |
| A29P, A53P, S74P, V82I, M98I, N191P | ++ |
| A29P, A53P, S74P, T81K, M98I, Q147S, N191P, T219Q | ++ |
| A29P, Q43E, A53P, S74P, M98I, N191P, T219D | ++ |
| A29P, Q43R, A53P, S74P, T81N, N191P | ++ |
| A29P, Q43E, A53P, S74P, M98V, S136D, Q147S, N191P | ++ |
| A29P, Q43L, A53P, S74P, M98I, N191P, T219E | ++ |
| A29P, A53P, S74P, T81K, M98I, A165S, N191P, T219E | ++ |
| A29P, Q43K, A53P, S74P, Y91F, M98V, N191P, N207D, T219Q | ++ |
| A29P, Q43R, A53P, S74P, M98T, N191P, T219E | ++ |
| A29P, Q43R, A53P, S74P, T81K, M98V, N191P | ++ |
| A29P, Q43K, A53P, S74P, M98I, Q147S, N191P, T219Q | ++ |
| A29P, Q43E, A53P, S74P, M98I, N191P | ++ |
| A29P, Q43K, A53P, S74P, T81N, Y91F, S136K, N191P | ++ |
| A29P, Q43L, A53P, S74P, T81N, M98I, N191P | ++ |
| A29P, Q43R, A53P, S74P, Y91F, N191P, T219D | ++ |
| A29P, Q43R, A53P, S74P, T81N, Q147R, N191P, T219D | ++ |
| A29P, A53P, S74P, M98I, S136H, N191P, T219Q | ++ |
| A29P, A53P, S74P, T81K, M98V, A165S, N191P | ++ |
| A29P, A53P, S74P, M98I, S136R, N191P | ++ |
| S10H, A29P, T33L, A53P, S74P, L79I, A141S, N191P | ++ |
| S10T, A29T, A53P, S74P, L79I, N191P, T219Q | ++ |
| S10H, A29P, T33I, A53P, S74P, S185E, N191P | ++ |
| S10H, A29T, A53P, S74P, N191Q | ++ |
| S10H, A29P, A53P, S74P, N191P | ++ |
| S10H, A29P, A53P, S74P, A141S, S185T, N191P | ++ |
| S10H, A29P, T33I, A53P, S74P, L79I, S185E, N191P | ++ |
| A29P, T33H, A53P, S74P, M98I, N191P, T222K | ++ |
| A29P, A53P, S74P, M98I, N191P | ++ |
| A29P, T33L, A53P, S74P, Q78K, S80K, V82I, N191P, P204L | ++ |
| A29P, T33V, A53P, S74P, V82I, T110K, R118K, N191P | ++ |
| A29P, T33I, A53P, S74P, Q78K, S80K, V82I, N191P, P204L, Q206E | ++ |
| A29P, T33V, A53P, S74P, S80K, V82I, N191P, Q206E | ++ |
| A29P, T33Q, Q43V, A53P, V60I, S74P, Q78K, N191P, Q206E | ++ |
| A29P, T33V, N51S, A53P, S74P, V82I, Q182V, N191P, P204L, Q206E | ++ |
| A29P, A53P, S74P, V82I, T110K, N191P, T219C | ++ |
| A29P, T33L, Q43V, A53P, S74P, Q78K, N191P, P204L, Q206V | ++ |
| A29P, T33I, A53P, S74P, V82I, N191P | ++ |
| A29P, A53P, S74P, V82I, N191P, P204L, T219C | ++ |
| A29P, T33Q, A53P, S74P, S80K, V82I, R118K, T142V, Q182V, N191P, P204L | +++ |
| A29P, A53P, S74P, Q78K, V82I, N191P, Q206V | ++ |
| A29P, T33L, Q43V, A53P, S74P, Q78K, V82I, Q182V, N191P | ++ |
| A29P, T33Q, A53P, S74P, S80K, V82I, T110K, N191P, P204L, Q206E | ++ |
| D1V, A29P, Q43V, A53P, S74P, S80K, V82I, N191P, P204L, Q206E | +++ |
| A29P, T33V, A53P, S74P, Q78K, S80K, V82I, N191P, P204L, Q206E | +++ |
| A29P, T33Q, Q43R, A53P, S74P, V82I, N191P, T219A | ++ |
| A29P, A53P, S74P, Q78K, V82I, N191P, Q206E, T219A | ++ |
| A29P, T33Q, A53P, S74P, Q78K, V82I, R118K, N191P, P204L | +++ |
| A29P, A53P, S74P, Q78K, S80K, V82I, N191P, Q206V | ++ |
| A29P, Q43V, A53P, S74P, Q78K, V82I, N191P, P204L | +++ |
| A29P, A53P, S74P, S80K, V82I, Q182V, N191P, P204L, T219C | ++ |
| S10F, A29P, A53P, S74P, V82I, N191P, P204L | ++ |
| A29P, T33I, A53P, S74P, Q78K, V82I, Q182V, N191P, P204L | ++ |
| A29P, Q43V, A53P, S74P, N191P, P204L, Q206E | ++ |
| A29P, T33V, Q43V, A53P, S74 P, Q78K, S80K, V82I, N191P, P204L, Q206V | +++ |
| A29P, T33V, Q43V, A53P, S74P, V82I, N191P, P204L, Q206E, T219A | +++ |
| A29P, T33I, Q43V, A53P, S74P, N191P, P204L | ++ |
| A29P, T33L, A53P, S74P, V82I, R118K, N191P | ++ |
| A29P, A53P, S74P, Q78K, V82I, T142W, Q182V, N191P | ++ |
| A29P, A53P, S74P, V82I, R118K, Q182V, N191P, P204L | ++ |
| A29P, A53P, S74P, M98I, T142S, N191P, N207G, T222K | ++ |
| Q14L, A29P, T33A, A53P, S74P, M98I, N191P | ++ |
| Q14L, A29P, T50L, A53P, S74L, M98I, N191P | ++ |
| Q14L, A29P, A53P, S74P, M98I, N191P, N207G | ++ |
| A29P, A53P, S74P, T142N, N191P, N207G | ++ |
| A29P, A53P, S74P, M98I, T142M, N191P | ++ |
| A29P, T50L, A53P, S74P, N191P | ++ |
| A29P, A53P, S74K, A77V, M98I, N191P | ++ |
| A29P, T33A, T50L, A53P, S74Q, A77V, S95H, M98I, T142M, N191P, N207G | ++ |
| A29P, A53P, S74P, M98I, T142N, N191P, N207G | ++ |
| Q14L, A29P, A53P, S74K, T142N, N191P | ++ |
| A29P, A53P, S74V, A77V, M98I, N191P, N207G | ++ |
| A29P, A53P, S74Q, A77V, M98I, N191P | ++ |
| D1G, A29P, A53P, S74K, A77V, M98I, N191P | ++ |
| A29P, A53P, S74L, S95H, M98I, T142M, N191P | ++ |
| A29P, T50L, A53P, S74P, M98I, N191P | +++ |
| A29P, T50L, A53P, S74P, T142M, N191P | ++ |
| A29P, A53P, S74L, M98I, A102S, N191P | ++ |
| A29P, A53P, S74T, M98I, N191P | ++ |
| A29P, V48K, A53P, N68V, S74P, N191P | ++ |
| T12I, A29P, A53P, N68K, S74P, S152M, N191P | +++ |
| A29P, V48K, A53P, N68K, S74P, S152M, N191P | ++ |
| A29P, V48K, A53P, N68I, S74P, N191P | ++ |
| A29P, V48K, A53P, N68K, S74P, N191P | ++ |
| T12V, A29P, V48K, A53P, S74P, S152M, N191P | ++ |
| T12I, A29P, A53P, N68V, S74P, N191P | ++ |
| T12V, A29P, V48K, A53P, S74P, N191P | ++ |
| A29P, I41V, A53P, S74P, N191P | ++ |
| T12V, A29P, A53P, S74P, N191P | ++ |
| T12I, A29P, V48K, A53P, N68K, S74P, S152M, N191P | ++ |
| T12V, A29P, A53P, S74P, S152M, N191P | ++ |
| A29P, A53P, N68K, S74P, S152M, N191P | ++ |
| A29P, V48K, A53P, S74P, S152M, N191P | ++ |
| A29P, V48K, A53P, N68I, S74P, N191P | ++ |
| T12V, A29P, A53P, S74P, N191P | ++ |
| A29P, A53P, N68V, S74P, S152M, N191P | ++ |

[1]Fold improvement is represented as follows:
++ = 1.1 to 1.5 fold improvement over control (A29P, A53P, S74P, N191P)
+++ = 1.6 to 2.8 fold improvement over control (A29P, A53P, S74P, N191P)

Table 4C shows improved endoglucanse variants derived from the "SavO native 4" EG catalytic domain, also referred to as "CDX-SavOcat" (SEQ ID NO: 2). The variants were not directly compared to the CDX-SavOcat in screening but were compared to the best variant, from Table 4B (S10W, A29P, Q43R, A53P, S74P, V82I, M98V, N191P) and this sequence was used as the control ("+control") to estimate fold improvement (FI) over the CDX-SavOcat activity. Both the CDX-SavOcat and the variants in Tables 4A-C contain the N-terminal "DTSM" spacer (SEQ ID NO:16). In Table 4C, the SavO EG catalytic domain without N-terminal spacer (corresponding to SEQ ID NO:1) was used as the reference sequence for the numbering of the changed amino acid residues.

TABLE 4C

| Amino Acid Changes | Fold improvement[1] |
|---|---|
| S10W, A29P, Q43R, A53P, S74P, V82I, M98V, N191P (SEQ ID NO: 7) | |
| S10W; T12V; A29P; Q43R; V48K; A53P; N68I; S74P; V82I; M98V; S152M; N191P | +++++ |
| S10W; T12V; A29P; Q43R; V48K; A53P; N68I; S74P; Q78K; T81K; V82I; M98V; S152M; N191P; | +++++ |
| S10W; T12V; A29P; Q43R; A53P; N68I; S74P; V82I; Y91C; M98V; S185Q; N191P | ++++ |
| S10W; T12V; A29P; Q43R; S74P; Q78K; L79I; V82I; M98V; S152M; S185K; N191P; Q206E; | ++++ |
| S10W; A29P; Q43R; V48K; A53P; S74P; V82I; M98V; N191P; | ++++ |
| S10W; T12I; A29P; Q43R; A53P; N68I; S74P; V82I; M98V; S152M; S185V; N191P; | +++++ |
| S10W; A29P; Q43R; A53P; S74P; V82I; M98V; S152M; N191P; Q206E; | ++++ |
| S10W; T12V; A29P; Q43R; V48K; A53P; S74P; V82I; M98V; S185V; N191P; | +++++ |
| S10W; T12I; A29P; Q43R; A53P; N68K; S74P; Q78K; V82I; M98V; S152M; N191P; | +++++ |
| S10W; T12V; A29P; Q43R; A53P; S74P; Q78K; T81K; V82I; M98V; S152M; S185Q; N191P | +++++ |
| S10W; T12V; A29P; Q43R; V48K; A53P; N68I; S74P; Q78K; L79I; V82I; M98V; N191P | +++++ |
| S10W; T12I; A29P; Q43R; A53P; N68I; S74P; Q78K; V82I; M98V; S152M; N191P; Q206E; | +++++ |
| S10W; T12V; A29P; Q43R; A53P; N68I; S74P; L79I; V82I; M98V; S152M; N191P; Q206E; | +++++ |
| S10W; T12I; A29P; Q43R; V48K; A53P; N68I; S74P; Q78K; L79I; V82I; M98V; S152M; N191P; Q206E; | +++++ |
| S10W; T12V; A29P; Q43R; V48K; A53P; N68I; S74P; Q78K; T81K; V82I; M98V; S152M; N191P; Q206E; | +++++ |
| S10W; T12V; A29P; Q43R; V48K; A53P; N68I; S74P; L79I; T81K; V82I; M98V; S152M; S185Q; N191P; Q206E; | +++++ |
| S10W; A29P; Q43R; V48K; A53P; N68I; S74P; Q78K; V82I; M98V; S152M; N191P; Q206E; | +++++ |
| S10W; T12V; A29P; Q43R; V48K; A53P; N68I; S74P; V82I; M98V; A141T; S152M; S185Q; N191P; Q206E; | +++++ |
| S10W; T12V; A29P; Q43R; V48K; A53P; N68I; S74P; L79I; V82I; M98V; S152M; N191P; | +++++ |
| S10W; T12I; A29P; Q43R; V48K; A53P; N68I; S74P; Q78K; V82I; M98V; S152M; N191P; | +++++ |
| S10W; T12V; A29P; Q43R; V48K; A53P; N68I; S74P; Q78K; L79I; T81K; V82I; M98V; S152M; S185V; N191P; Q206E; | +++++ |
| S10W; A29P; Q43R; V48K; A53P; N68I; S74P; L79I; T81K; V82I; M98V; S152M; S185V; N191P; Q206E | +++++ |
| S10W; T12V; A29P; Q43R; V48K; A53P; N68I; S74P; Q78K; L79I; T81K; V82I; M98V; S152M; S185G; N191P; Q206E; | +++++ |
| S10W; T12I; A29P; Q43R; V48K; A53P; N68I; S74P; T81K; V82I; M98V; S152M; N191P; | +++++ |
| S10W; A29P; Q43R; A53P; N68I; S74P; Q78K; L79I; V82I; M98V; S152M; S185V; N191P; Q206E; | +++++ |
| S10W; A29P; Q43R; V48K; A53P; N68I; S74P; Q78K; L79I; V82I; M98V; S152M; S185Q; N191P; Q206E; | +++++ |
| S10W; A29P; Q43R; V48K; A53P; N68I; S74P; L79I; T81K; V82I; M98V; S152M; S185Q; N191P; | +++++ |
| S10W; T12I; A29P; Q43R; V48K; A53P; N68I; S74P; Q78K; V82I; M98V; N191P; | +++++ |
| S10W; T12V; A29P; Q43R; V48K; A53P; N68I; S74P; Q78K; V82I; M98V; S152M; S185V; N191P; Q206E; | +++++ |

[1]Fold improvement is over Control Variant from Table 4B
(S10W, A29P, Q43R, A53P, S74P, V82I, M98V, N191P), SEQ ID NO: 7, represented as follows:
++++ = 1.1 to 1.5 fold improvement over control
(S10W, A29P, Q43R, A53P, S74P, V82I, M98V, N191P)
+++++ = 1.6 to 3.0 fold improvement over control
(S10W, A29P, Q43R, A53P, S74P, V82I, M98V, N191P)

Six SavO EG variants and CDX-SavOcat were characterized to determine their stabilities at high temperature (65-70° C.). The samples containing various SavO EG variant enzymes were pre-incubated at pH 4-5, 65-70° C. for 0-48 hrs. The residual enzyme activity after the thermal challenge was measured using pNPC as substrate at pH 5, 50° C. for 1 hr. Table 5 illustrates the half-lives of improved SavO EG variants at pH 5, 65° C. and pH 4, 70° C.

TABLE 5

Half-lives of improved SavO EG variants

| Variant Identification | Amino acid changes | Half-life at pH 5, 65° C. (minute) | Half-life at pH 4, 70° C. (minute) |
|---|---|---|---|
| SavO native 4 (SEQ ID NO: 2) | CDX-SavOcat (control) | 4 | 1 |
| SavO variant 1 SEQ ID NO: 6 | A29P; A53P; S74P; N191P; | 27 | 2 |
| SavO variant 3 SEQ ID NO: 7 | S10W; A29P; Q43R; A53P; S74P; V82I; M98V; N191P; | 990 | 21 |
| SavO variant 5 SEQ ID NO: 8 | S10W; T12V; A29P; Q43R; V48K; A53P; N68I; S74P; L79I; T81K; V82I; M98V; S152M; S185Q; N191P; Q206E; | 3071 | 748 |
| SavO variant 2 | S10W; T12I; A29P; Q43R; V48K; A53P; N68I; S74P; Q78K; V82I; M98V; S152M; N191P; | 2773 | 518 |
| SavO variant 7 | S10W; T12I; A29P; Q43R; V48K; A53P; N68I; S74P; Q78K; V82I; M98V; N191P; | 3257 | 287 |

TABLE 5-continued

Half-lives of improved SavO EG variants

| Variant Identification | Amino acid changes | Half-life at pH 5, 65° C. (minute) | Half-life at pH 4, 70° C. (minute) |
|---|---|---|---|
| SavO variant 6 | S10W; T12V; A29P; Q43R; V48K; A53P; N68I; S74P; Q78K; L79I; T81K; V82I; M98V; S152M; S185V; N191P; Q206E; | 2944 | 518 |

The improved SavO EG variants were validated under saccharification conditions. FIG. 4 shows production of cellobiose and glucose over 48 hours by various endoglucanases of the present invention (SavO native 4, SavO variant 3, SavO variant 5, and SavO variant 6) under the conditions of: 200 g/L Avicel, pH 4, 70° C. SavO variant 5 exhibited the highest stability under the conditions tested.

Example 9

Improved Glucogenic Activity of Engineered SavO EG Variant

The dose response of the CDX-SavOcat (SEQ ID NO: 2) or SavO variant 5 (SEQ ID NO: 8) was evaluated under the saccharification relevant condition pH 5, 65° C. Production of cellobiose and glucose from Avicel was measured over 48 hr periods with different SavO EG enzyme loading (0-2.5 g/L). Surprisingly, SavO EG variant 5 exhibited significant glucogenic activity. Under this condition, SavO variant 5 exhibited ~16×improved glucogenic activity compared with the CDX-SavOcat (SEQ ID NO: 2). See FIG. 5.

Example 10

Signal Peptide for SavO EG production in *Bacillus megaterium*

The signal peptide sequence MKRIVMVGFILLFPLNM-LAGPISSIAEAQ (SEQ ID NO: 9) from *B. megaterium* ORF_2879 was used for production of SavO EG in a *B. megaterium* host. The signal peptide and the SavO EG gene (SavO variant 5, SEQ ID NO: 8) were cloned into an *E. coli/B. megaterium* shuttle vector as described in Example 1. A SpeI site introduced to facilitate cloning introduced the tripeptide TSM between the signal peptide carboxy terminus and EG amino terminus (SEQ ID NO:10). The resulting plasmid was transformed into *B. megaterium* protoplasts as described in Example 1. The construct was grown in HTP, and activities of clear media supernatant and cell lysate were determined by pNPC and Avicel assays as described in Example 5. Assay conditions were 5 mM pNPC, pH 5, 45° C. for 1 hr. The activity data suggested that ~97% of SavO EG was secreted from *B. megaterium*.

SavO EG variant 5 was also produced using this signal peptide at shake flask and fermentation scales by following procedures described in Examples 2, 3 and 4. FIG. 6 shows that two independently isolated clones comprising SEQ ID NO:10 (S0544 and S0704) increased the amount of EG production by about 1.5-fold compared to a positive control (*B. megaterium* optimized signal peptide, described above, linked to the SavO sequence).

Example 11

Reduction of yield stress of pretreated bagasse by SavOEG

Pretreated bagasse containing 60% glucan was milled using an IKA A11 analytical mill (Wilmington, U.S.A) and sieved using a 35 mesh sieve. The fractions less than 35 mesh were collected and a solution of bagasse was prepared in 250 mM sodium acetate buffer of the desired pH (3.5-5.5). Experiments were conducted in a total volume of 10 ml in 20 ml scintillation vials. SavO EG Variant 5 was added to a final concentration of 3.7% (w/w with regard to glucan weight) and final substrate load of 200 g/l. Controls containing no SavO were incubated under identical conditions. Soluble sugars and yield stress were measured at the end of 46 hrs of reaction time. Oscillatory stress sweeps were used to determine the yield stress, generally as described in Knutson and Liberatore, 2009, *J. Rheol.* 53:877-92. Yield stress and phase angle of samples and controls were measured using a Malvern Bohlin Gemini rheometer (Westborough, Mass., USA) in oscillation mode at a frequency of 1 Hz. Two geometries were used for this purpose. For thick and viscous samples (primarily, the controls), parallel plate geometry (20 mm) was used to determine the yield stress. Treatment with SavO, rendered bagasse samples "fluid like" with reduction in particle size and complete homogenization. Hence vane-in-cup geometry (10 mm vane in a 14 mm cup) was used to measure yield stress of these samples. All measurements were conducted at 25° C. with temperature controlled by Peltier heat exchanger. Yield stress is defined as the stress at which the phase angle becomes greater than 45°.

For measurement of soluble sugars, an aliquot of 1 ml was withdrawn into a microfuge tube and centrifuged. The supernatant was collected and quenched with the addition of 10 mM sulfuric acid (1:1) and then filtered. Cellobiose and glucose were measured using an Agilent HPLC 1200 equipped with HPX-87H ion exclusion column with 5 mM $H_2SO_4$ at a flow rate of 0.6 ml/min at 65° C. The retention times of cellobiose and glucose was 7.5 and 9.1 minutes respectively.

Results

SavO EG can be effectively used in lowering the yield stress of bagasse as shown in Table 6. Controls with no added enzyme had a yield stress of 3000 Pa. Addition of 3.7% SavO EG Variant 5 (SEQ ID NO:8) for 46 hours led to significant reduction (90 to 99.7% reduction) of yield stress of pretreated bagasse. This suggests that evolved SavO EG is capable of reducing the yield stress of the bagasse under a range of pH and temperature conditions.

TABLE 6

| SavO | pH | Temp (° C.) | Yield Stress (Pa) |
|---|---|---|---|
| Control, no enzyme | 3.5 | 65 | 3000 |
| 3.7% | 3.5 | 65 | 295 |
| 3.7% | 4.5 | 50 | 8 |
| 3.7% | 4.5 | 75 | 33 |
| 3.7% | 5.0 | 75 | 9 |
| 3.7% | 5.0 | 60 | 18 |

Example 12

Combination of Enzymes (SavO+Accellerase™ 1000)

Saccharification reactions were conducted using Accellerase™ 1000 supplemented with SavO Variant 6. The reaction was conducted in 2 stages. In the first stage, 0.25% SavO EG was added to the reactor and the reactor was incubated at pH 5.0, 75° C. for 24 hrs. After this time, additional Accellerase™ 1000 was added so that the final enzyme load was 2% w/w with respect to glucan in bagasse. The reaction was then incubated 50° C. for 24 hrs. Soluble sugars were measured at the end of 48 hrs of reaction time as described in Example 1. The results are outlined in Table 7.

TABLE 7

| Expt | Reactor 1: 75° C. | Reactor 2: 50° C. | Total enzyme (%) | Total Glucose (g/l) |
|---|---|---|---|---|
| 1 | SavO Variant 6, 0.25%, 24 hrs | Accellerase ™ 1000: 1.75%, 24 hr | 2 | 40.7 |
| 2 | | Accellerase ™ 1000, 2%, 48 hrs | 2 | 25.3 |

As seen in Table 7, when the 2% Accellerase™ 1000 was used alone with 200 g/l bagasse, a glucose yield of 25 g/l was obtained (Expt 2). However when a combination of 0.25% SavO+1.75% Accellerase™ 1000 was used, a yield of 40 g/l was obtained (Expt 1). Hence the addition of SavO resulted in a 60% increase in yields.

Example 13

Analytical Method to Determine CBH2 Activity

A sample can be tested for CBH2 activity using a cellulose assay, in which microcrystalline cellulase (e.g., Avicel; from Sigma) is used as substrate. In a total volume of 150 μL, 60 μL clear sample solution (which may contain a CBH2 enzyme) is added to 200 g/L Avicel in 100-250 mM sodium acetate buffer (pH 3-6). The reaction is incubated at 50-70° C. for 24 hours. Biotransformations are quenched with 50% acetonitrile. The reaction mixture is centrifuged, and the supernatant (150 μl) is collected and filtered through a 0.45 μm filter. Conversion of Avicel to soluble sugar oligomers is measured by HPLC. For example, using an Agilent HPLC 1200 equipped with HPX-87H Ion exclusion column (300 mm×7.8 mm) with 5 mM H2SO4 at a flow rate of 0.6 ml/min at 65° C. typical retention times of the cellobiose and glucose are 7.5 and 9.1 minute respectively.

Example 14

Measuring Beta-Glucosidase Activity

Assays for beta-glucosidase activity are well known and include pNPG and cellobiose assays. In an exemplary pNPG assay, in a total volume of 100 μL, 20 μL clear media supernatant containing β-glucosidase enzyme is added to 4 mM pNPG (Sigma-Aldrich, Inc. St. Louis, Mo.) solution in 50 mM sodium phosphate buffer at pH 6.5. The reactions are incubated at pH 6.5, 45° C. for 1 hour. The reaction mixture is quenched with 100 μL of 1M sodium carbonate pH 11 solution. The absorbance of the solution is measured at 405 nm to determine the conversion of pNPG to p-nitrophenol. The release of p-nitrophenol ($\epsilon$=17,700 M−1 cm−1) is measured at 405 nm to calculate β-glucosidase activity. Detectable β-glucosidase activity is observed under high throughput screening conditions (pH 7, 50° C.). See Breves et al., 1997, Appl. Environmental Microbiol. 63:3902, incorporated herein by reference.

Alternatively, β-glucosidase activity may be determined using an assay, which uses cellobiose as substrate. In a total volume of 100 μL, 25 μL clear media supernatant containing β-glucosidase enzyme is added to 10 g/L cellobiose (Fluka Cat. No. 22150, Sigma-Aldrich, Inc., St. Louis, Mo.) in 100 mM sodium phosphate buffer (pH 6-7) or sodium acetate buffer (pH 5-5.5). The reaction is incubated at 45-70° C. for an appropriate time (25 minutes to overnight depending on the enzyme concentration) while shaking. Glucose production is determined using an enzymatic glucose assay (K-GLUC, Megazyme, Ireland). 10 μl of each reaction is added to 190 μl GOPOD reagent (supplied as part of the K-GLUC assay kit). The reaction is incubated at 45° C. for 20 minutes and the absorbance of the solution was measured at 510 nm. The GOPOD reagent contains 50 mM Potassium phosphate buffer pH7.4, 0.011M p-hydroxybenzoic acid, 0.008% w/v sodium azide, glucose oxidase (>12,000 U/L), peroxidase (>650 U/L) and 80 mg/L 4-aminoantipyrine. The glucose oxidase enzyme in the reagent reacts with any glucose present in the sample and produces hydrogen peroxide which then reacts with the 4-aminoantipyrine to produce a quinoneimine dye in quantities proportionate with the amount of glucose present and can be measured spectrophotometrically at 510 nm.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A variant endoglucanase polypeptide having catalytic activity comprising a catalytic domain comprising at least 70% sequence identity to the *Streptomyces* avermitilis endoglucanase catalytic domain (SEQ ID NO:1), wherein the amino acid at position 53, numbered with reference to SEQ ID NO:1, is not A.

2. The variant endoglucanase polypeptide of claim 1, wherein the amino acid at position 53 is G or P.

3. The variant endoglucanase polypeptide of claim 1, wherein as numbered with reference to SEQ ID NO:1, the polypeptide further comprises at least one of the following: the amino acid at position 29 is not A, the amino acid at position 74 is not S, or the amino acid at position 191 is not N.

4. The variant endoglucanase polypeptide of claim 3, wherein the amino acid at position 29 is H, K, L, P, R, or T; the amino acid at position 74 is A, E, H, K, L, N, P, Q, R, T or V; or the amino acid at position 191 is P, Q, or Y.

5. A variant endoglucanase polypeptide of claim 1, wherein as numbered with reference to SEQ ID NO:1, the polypeptide further comprises at least one of the following: the amino acid at position 10 is not S; the amino acid at position 12 is not T; the amino acid at position 29 is not A, the amino acid at position 43 is not Q, the amino acid at position 48 is not V, the amino acid at position 68 is not N, the amino acid at position 74 is not S, the amino acid at position 78 is not Q, the amino acid at position 79 is not L, the amino acid at position 81 is not T, the amino acid at position 82 is not V, the amino acid at position 98 is not M, the amino acid at position 152 is not S, the amino acid at position 185 is not S, the amino acid at position 191 is not N, or the amino acid at position 206 is not Q.

6. The variant endoglucanase polypeptide of claim 5, wherein the amino acid at position 53 is G or P; and the amino acid at position 10 is F, H, L, T, W, or Y; the amino acid at position 12 is a V or I; the amino acid at position 29 is H, K, L, P, R, or T; the amino acid at position 43 is R; the amino acid at position 48 is K; the amino acid at position 68 is I; the amino acid at position 74 is A, E, H, K, L, N, P, Q, R, T, or V; the amino acid at position 78 is K; the amino acid at position 79 is I; the amino acid at position 81 is K; the amino acid at position 82 is I; the amino acid at position 98 is V; the amino acid at position 152 is M; the amino acid at position 185 is Q or V, the amino acid at position 191 is P, Q, or Y; or the amino acid at position 206 is E.

7. The variant endoglucanase polypeptide of claim 1 that is derived from, and has improved catalytic activity relative to, a catalytic domain homolog of SEQ ID NO:1, wherein the homolog is from a *Streptomyces* species, a Micromonospora species, an Actinosynnema species, a Salinispora species, or a *Mycobacterium* species.

8. The variant endoglucanase polypeptide of claim 1 that comprises a cellulose binding domain.

9. The variant endoglucanase polypeptide of claim 4 wherein the endoglucanase catalytic domain and the cellulose binding domain are from the same parent endoglucanase.

10. The variant endoglucanase of claim 1, that has increased catalytic activity at pH 4.0 and 70° C. in comparison to an enzyme having a sequence set forth as SEQ ID NO:1.

11. An enzyme composition comprising a variant endoglucanase of claim 1.

12. A recombinant polynucleotide encoding a variant endoglucanase polypeptide of claim 1.

13. An expression vector comprising the polynucleotide of claim 12.

14. A host cell comprising the polynucleotide of claim 12.

15. A recombinant host cell that expresses a heterologous endoglucanase polypeptide according to claim 1.

16. The host cell of claim 15 that is a filamentous fungus or a *Bacillus* species.

17. A method of converting a biomass substrate to fermentable sugars comprising contacting the variant endoglucanase of claim 1 with said biomass under suitable conditions for the production of fermentable sugars.

18. The method of claim 17, comprising
  a) maintaining a slurry comprising
    i) a pretreated cellulosic feedstock and
    ii) an the variant endoglucanse
  under first saccharification conditions for a time sufficient to reduce the yield stress of the slurry; and then,
  b) combining the slurry with beta-glucosidase and cellobiohydrolase enzymes and maintaining the slurry under second saccharification conditions for a time sufficient to increase the amount of soluble sugars in the slurry.

19. The method of claim 18 wherein the slurry in step (a) is substantially free of cellobiohydrolase and beta-glucosidase activities.

20. The method of claim 18 wherein the first saccharification conditions comprise a temperature in the range 60° C.-80° C. and an acid pH, and the time sufficient to reduce the yield stress is in the range of 5 minutes to 24 hours.

21. The method of claim 18 wherein the beta-glucosidase and/or the cellobiohydrolase enzymes are inactive or are rapidly inactivated under the first saccharification conditions.

22. The method of claim 18 wherein the yield stress is decreased by at least 80% relative the initial yield stress of the slurry.

* * * * *